(12) United States Patent
Meir et al.

(10) Patent No.: US 8,399,026 B2
(45) Date of Patent: Mar. 19, 2013

(54) PEPTIDES ISOLATED FROM SPIDER VENOM, AND USES THEREOF

(75) Inventors: Alon Meir, Jerusalem (IL); Ronit Simcha Cherki, Jerusalem (IL); Ela Kolb, Jerusalem (IL); Yael Langut, Jerusalem (IL); Nissim Bajayo, Jerusalem (IL)

(73) Assignee: Alomone Preclinical Ltd., Jerusalem (IL)

( * ) Notice: Subject to any disclaimer, the term of this patent is extended or adjusted under 35 U.S.C. 154(b) by 38 days.

(21) Appl. No.: 12/881,269

(22) Filed: Sep. 14, 2010

(65) Prior Publication Data
US 2011/0065647 A1 Mar. 17, 2011

Related U.S. Application Data

(60) Provisional application No. 61/272,336, filed on Sep. 15, 2009.

(51) Int. Cl.
*A61K 35/64* (2006.01)
*A61P 25/04* (2006.01)

(52) U.S. Cl. ...... 424/538; 514/18.3; 514/21.3; 530/324; 530/858

(58) Field of Classification Search .......... None
See application file for complete search history.

(56) References Cited

U.S. PATENT DOCUMENTS

| | | | |
|---|---|---|---|
| 4,450,150 A | 5/1984 | Sidman | |
| 4,675,381 A | 6/1987 | Bichon | |
| 5,417,986 A | 5/1995 | Reid | |
| 5,877,026 A | 3/1999 | Lampe | |
| 6,670,329 B2 * | 12/2003 | Song-Ping | 514/17.4 |
| 2004/0192886 A1 | 9/2004 | Olivera | |
| 2006/0270832 A1 | 11/2006 | Lewis | |

OTHER PUBLICATIONS

Bulaj, Grzegorz et al., "Synthetic muO-conotoxin MrVIB blocks TTX-resistant sodium channel NaV1.8 and has a long-lasting analgesic activity", Biochemistry, 45(23):7404-7414 (2006).
Cabrele, Chiara et al., "Redox-active cyclic bis(cysteinyl)peptides as catalysts for in vitro oxidative protein folding", Chem Biol, 9(6):731-740 (2002).
Cummins, Theodore R., et al., "Nav1.3 sodium channels: rapid repriming and slow closed-state inactivation display quantitative differences after expression in a mammalian cell line and in spinal sensory neurons", J Neurosci, 21(16):5952-5961 (2001).
Cummins, Theodore R. and Rush, Anthony M., "Voltage-gated sodium channel blockers for the treatment of neuropathic pain", Expert Rev Neurother, 7(11):1597-1612 (2007).
Dascal, Nathan and Cohen, Sasson, "Further characterization of the slow muscarinic responses in Xenopus oocytes", Pflugers Arch, 409(4-5):512-520 (1987).
Devor, Marshall, "Sodium channels and mechanisms of neuropathic pain", J Pain, 7(1 Supp 1):S3-S12 (2006).
Escoubas, Pierre and Rash, Lachlan, "Tarantulas: eight-legged pharmacists and combinatorial chemists", Toxicon, 43(5):555-574 (2004).
Hamill, O. P. et al., "Improved patch-clamp techniques for high-resolution current recording from cells and cell-free membrane patches", Pflugers Arch, 391(2):85-100 (1981).
Hays, Ron D. and Stewart, Anita L., "Construct validity of MOS health meausures. Published in: Measuring functioning and well-being: The Medical Outcomes Study approach". Stewart, Anita L. & Ware, John E. Jr. (eds.) pp. 325-342 Durham, NC: Duke University Press (1992).
Jarvis, Michael F. et al., "A-803467, a potent and selective Nav1.8 sodium channel blocker, attenuates neuropathic and inflammatory pain in the rat", Proc Natl Acad Sci USA, 104(20):8520-8525 (2007).
John, Victoria H. et al., "Heterologous expression and functional analysis of rat Nav1.8 (SNS) voltage-gated sodium channels in the dorsal root ganglion neuroblastoma cell line ND7-23", Neuropharmacology, 46(3):425-438 (2004).
Mazzuca, Michel et al., "A tarantula peptide against pain via ASIC1a channels and opioid mechanisms", Nat Neurosci, 10(8):943-945 (2007).
Ostrow, Kimberly Laskie et al., "cDNA sequence and in vitro folding of GsMTx4, a specific peptide inhibitor of mechanosensitive channels", Toxicon, 42(3):263-274 (2003).
Reeck, Gerald R. et al., "Homology in proteins and nucleic acids: a terminology muddle and a way out of it", Cell, 50(8):667 (1987).
Redfern, W. S. et al., "Relationships between preclinical cardiac electrophysiology, clinical QT interval prolongation and torsade de pointes for a broad range of drugs: evidence for a provisional safety margin in drug development", Cardiovasc Res, 58(1):32-45 (2003).
Shcherbatko, A. et al., "Voltage-dependent sodium channel function is regulated through membrane mechanics", Biophys J, 77(4):1945-1959 (1999).
Schnolzer, Martina et al., "In situ neutralization in BOC-chemistry solid phase peptide synthesis", Int J Pept Protein Res, 40(3-4):180-193 (1992).
Zhou, Zhenfeng et al., "Properties of HERG channels stably expressed in HEK 293 cells studied at physiological temperature", Biophys J, 74(1):230-241 (1998).
Zhou, Xiaoping et al., "Vinpocetine is a potent blocker of rat NaV1.8 tetrodotoxin-resistant sodium channels", J Pharmacol Exp Ther, 306(2):498-504 (2003).
Zimmermann, Katharina et al., "Sensory neuron sodium channel Nav1.8 is essential for pain at low temperatures", Nature, 447(7146):855-858 (2007).
Swiss-Prot_P60975. Mu-theraphotoxin-Hhn1a. Jun. 16, 2009 [retrieved from the internet Apr. 12, 2011:,<URL:http://www.ncbi.nim.nih.gov/protein/46577307?sat=OLD07&satkey=3957391>].
P0c2P5, Swiss-Prot: ID VSTX3_GRARO. Jun. 16, 2009. [retrieved from the internet Feb. 3, 2011:,URL:http://www.uniprot.org/uniprot/P0C2P5.txt?version=11>].
ISR of PCT/IB10/02275 mailed May 10, 2011.

*Primary Examiner* — John Ulm
(74) *Attorney, Agent, or Firm* — Rodney J. Fuller; Booth Udall Fuller, PLC

(57) ABSTRACT

The presently described subject matter relates to isolated spider venom peptides, which are used as potent and selective ion channel blockers, and to a composition and methods for treatment of pain.

12 Claims, 34 Drawing Sheets

Separation on gel filtration, S-30 column

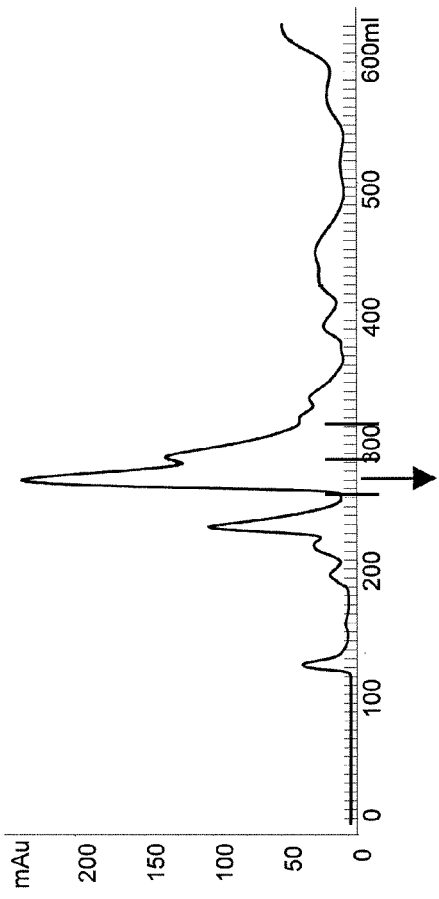
Fig. 2A
Separation on gel filtration, S-30 column
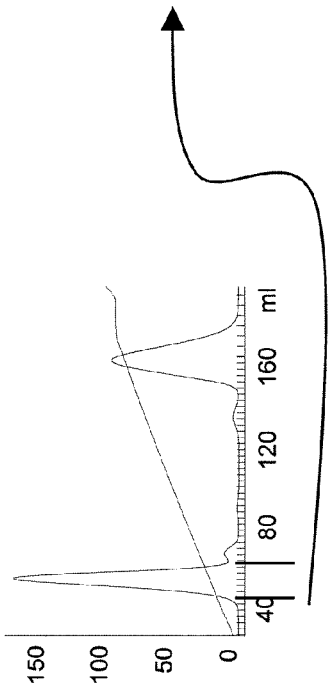
Fig. 2B
Separation on SP CEx (5mL)
Fig. 2C
Separation on HPLC - (50%X2)
MS verification of peptide B 3637 Da / 1.17mg

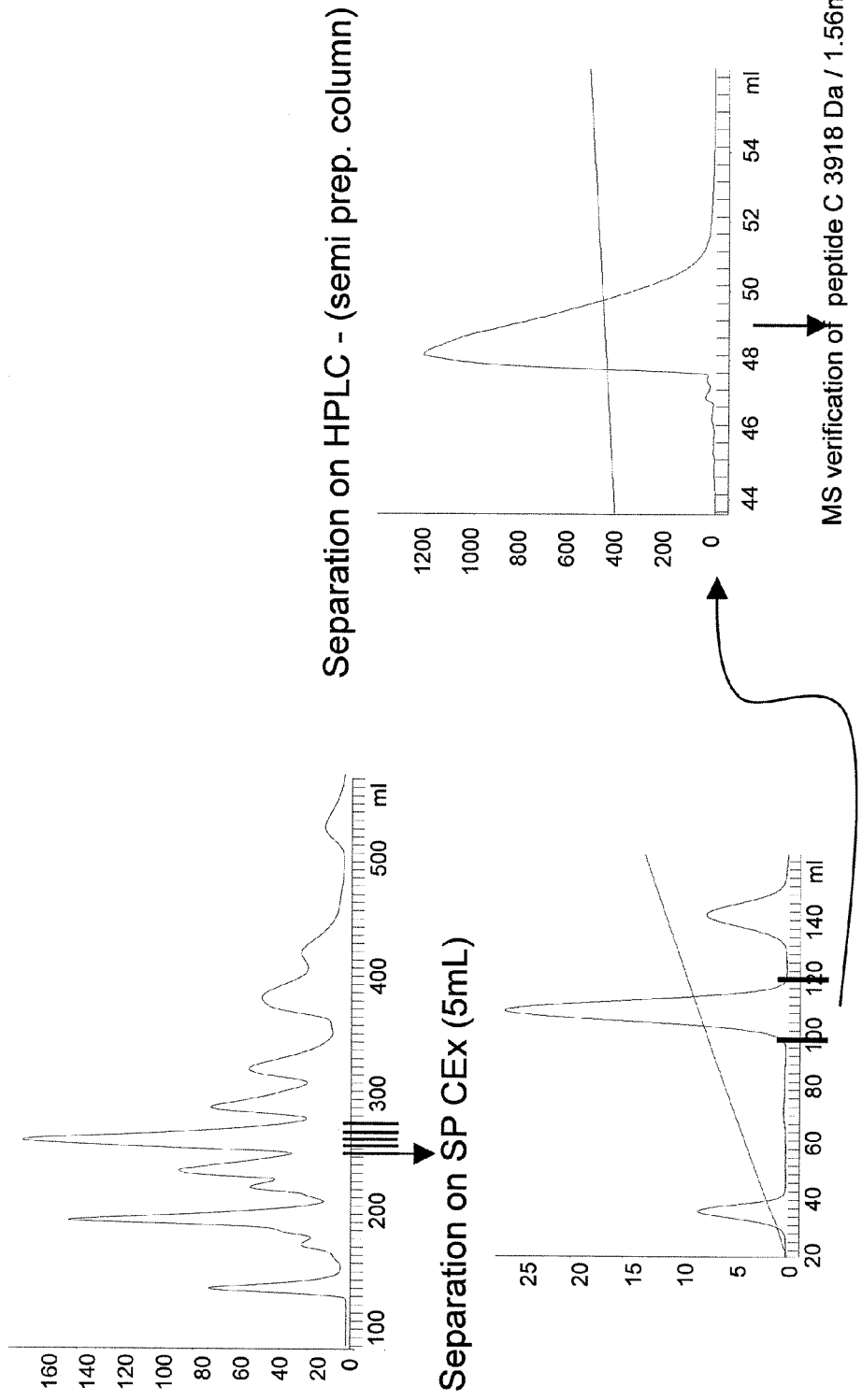

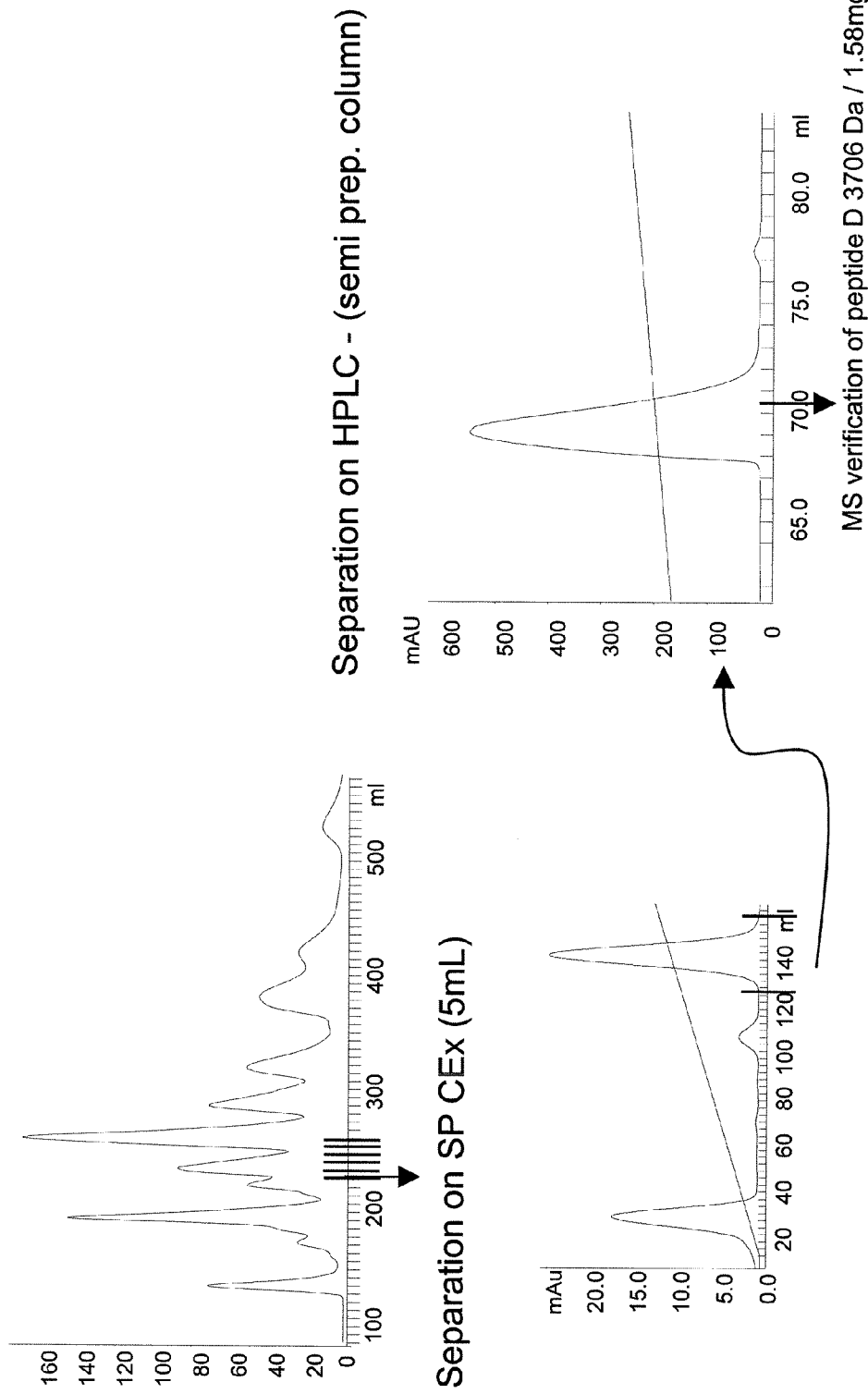

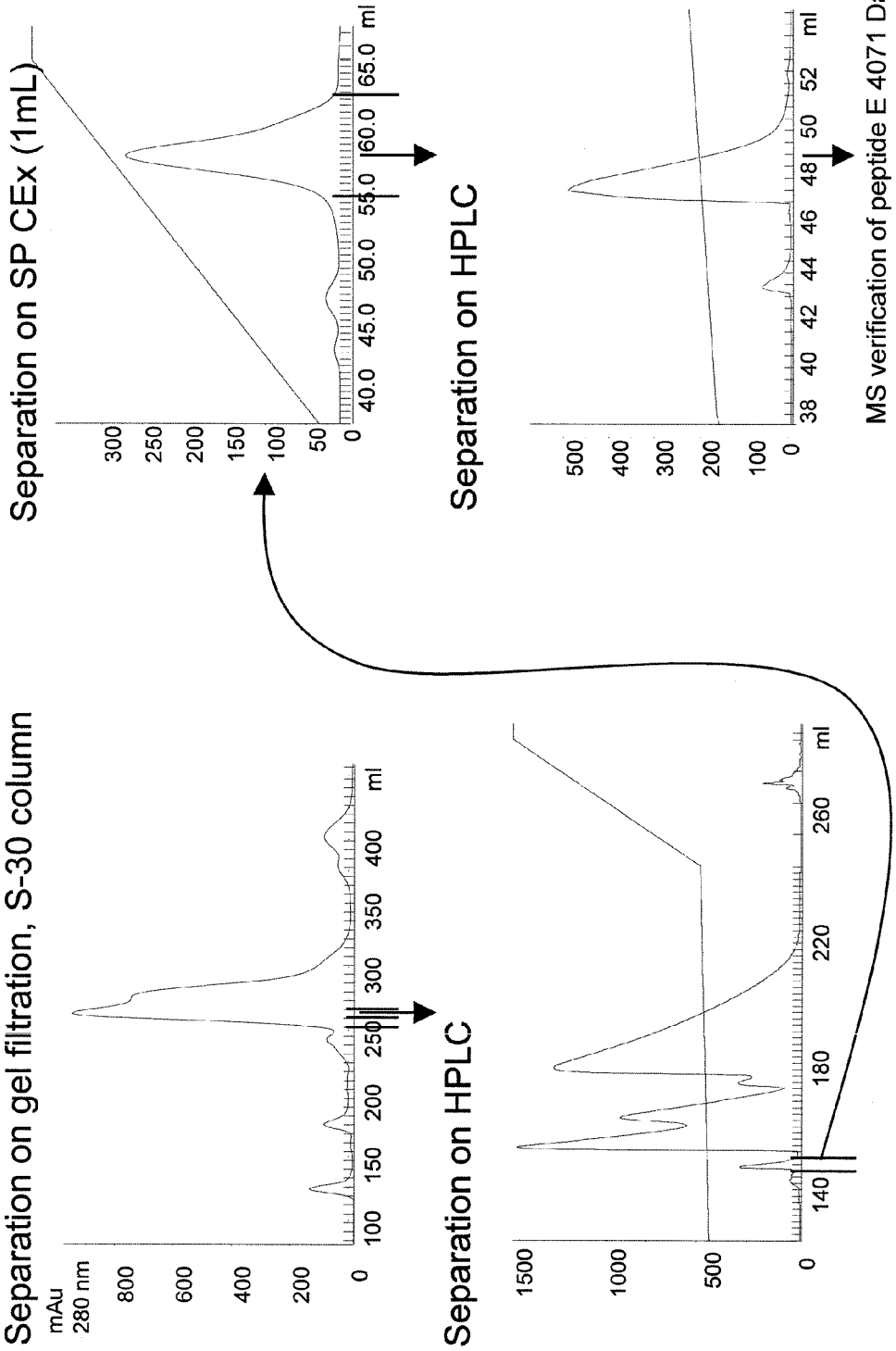
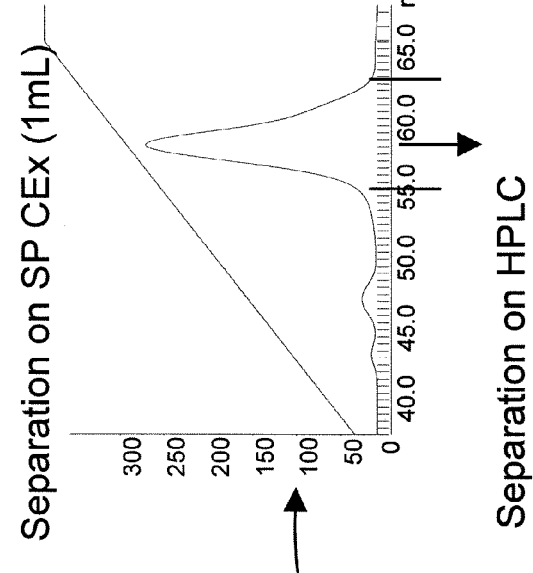
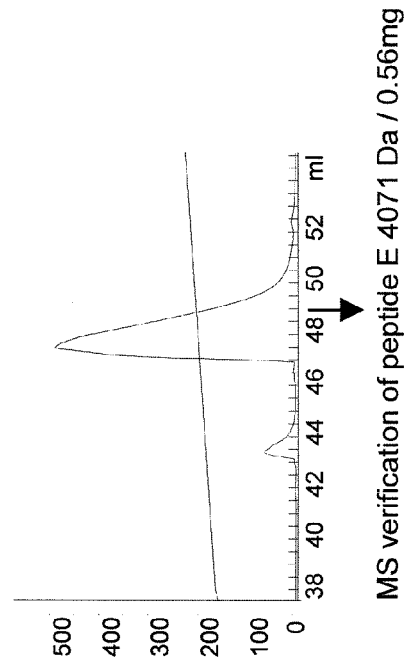
Fig. 5A Separation on gel filtration, S-30 column
Fig. 5B Separation on HPLC
Fig. 5C Separation on SP CEx (1mL)
Fig. 5D MS verification of peptide E 4071 Da / 0.56mg

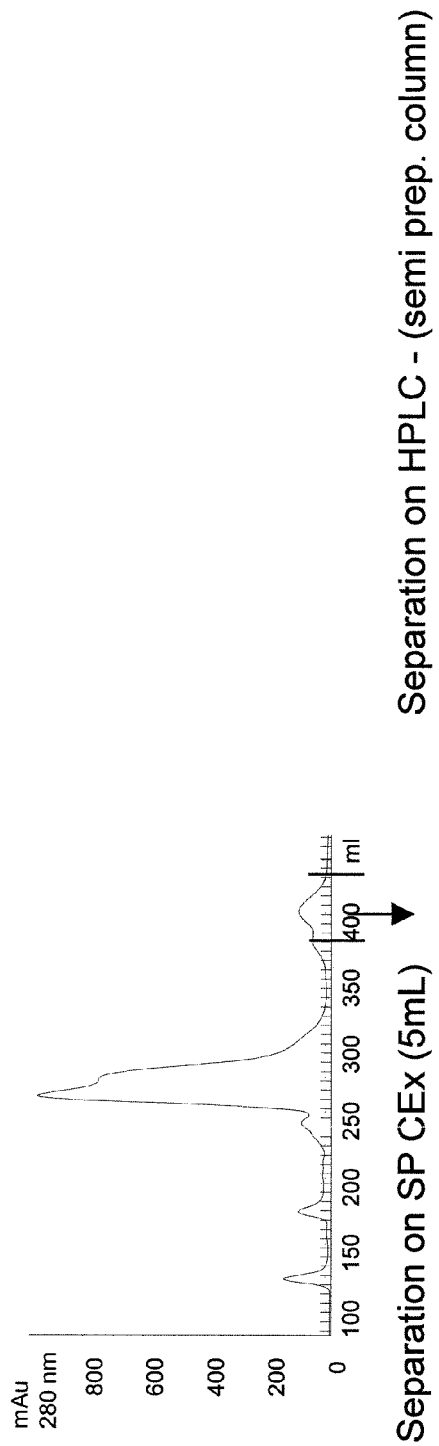
Fig. 6A
Separation on gel filtration, S-30 column
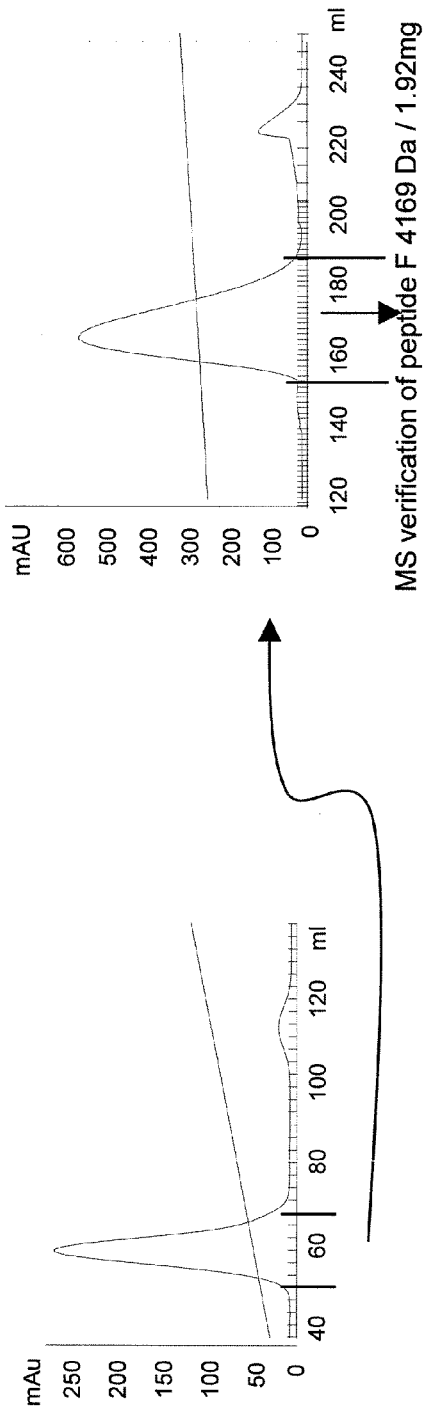
Fig. 6B
Separation on SP CEx (5mL)
Fig. 6C
Separation on HPLC - (semi prep. column)
MS verification of peptide F 4169 Da / 1.92mg

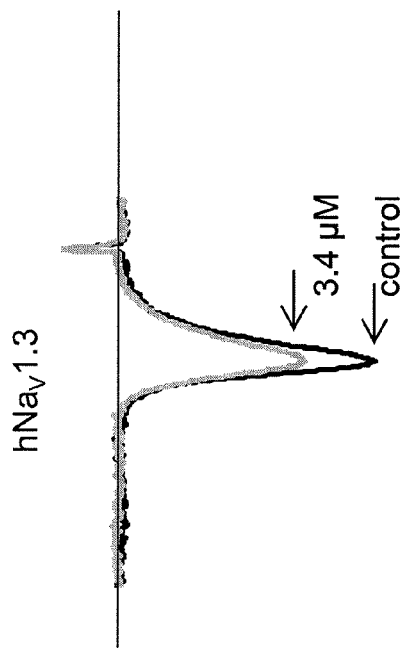
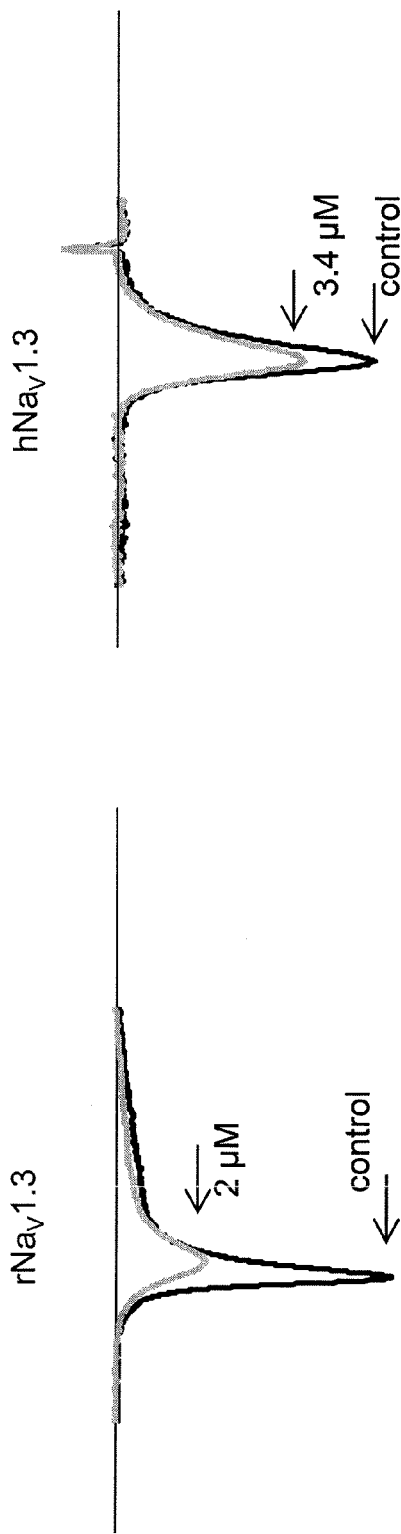
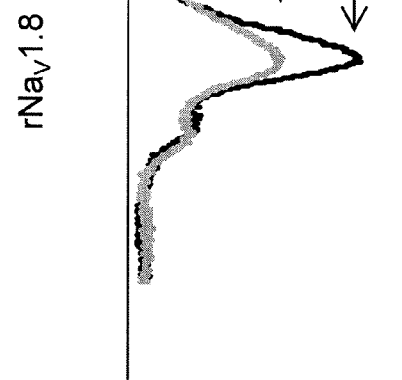

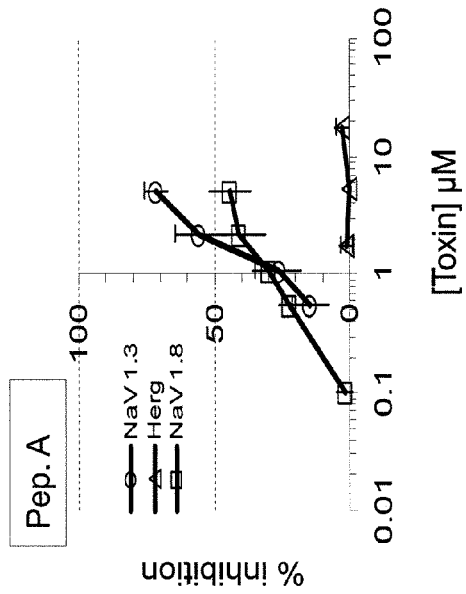
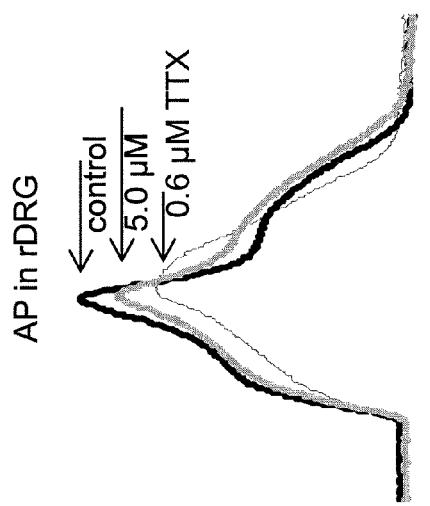
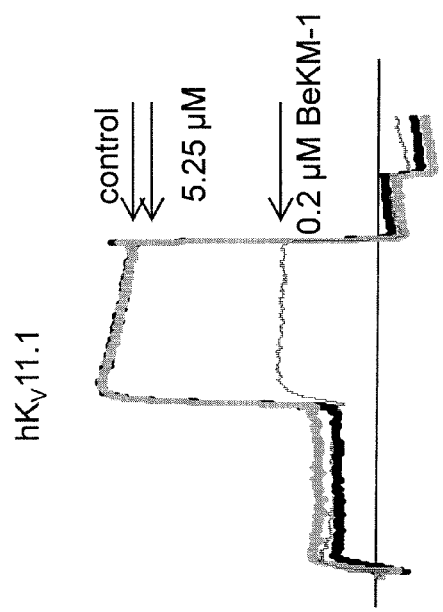

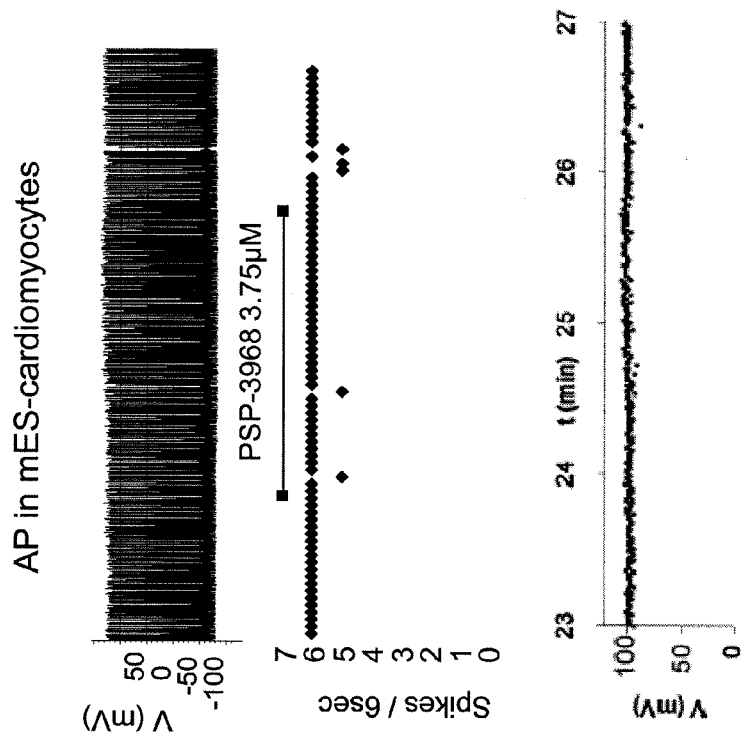
Fig. 7H
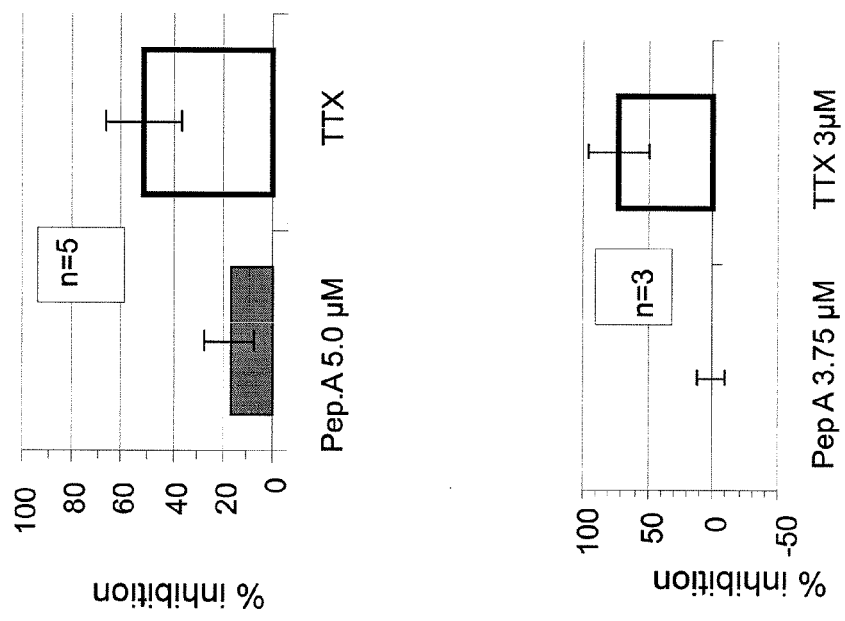
Fig. 7G
Fig. 7I hNa$_v$1.3 rNa$_v$1.8 rNa$_v$1.3

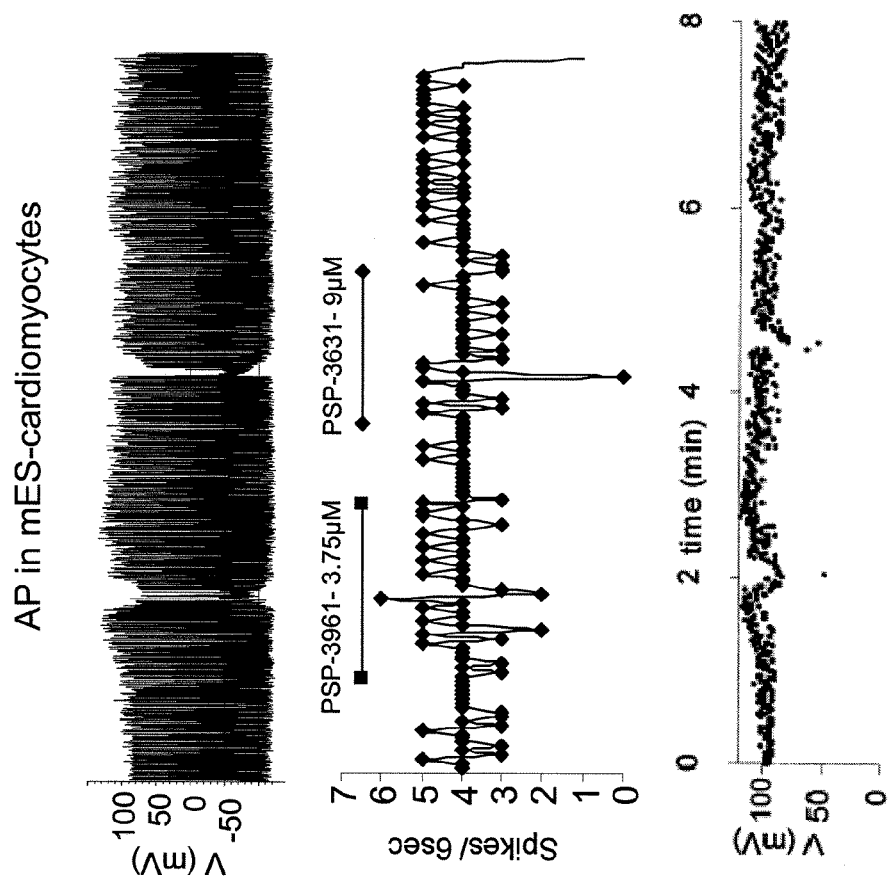
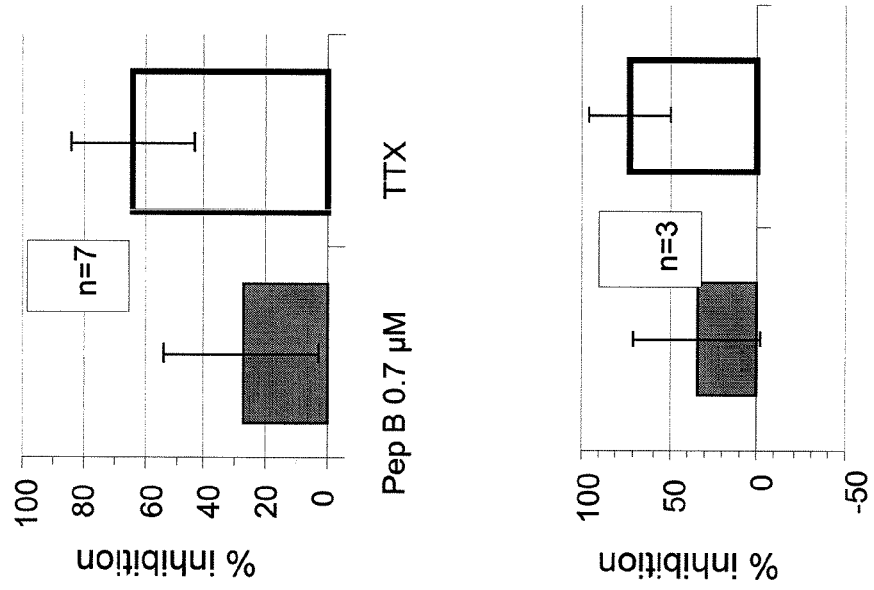

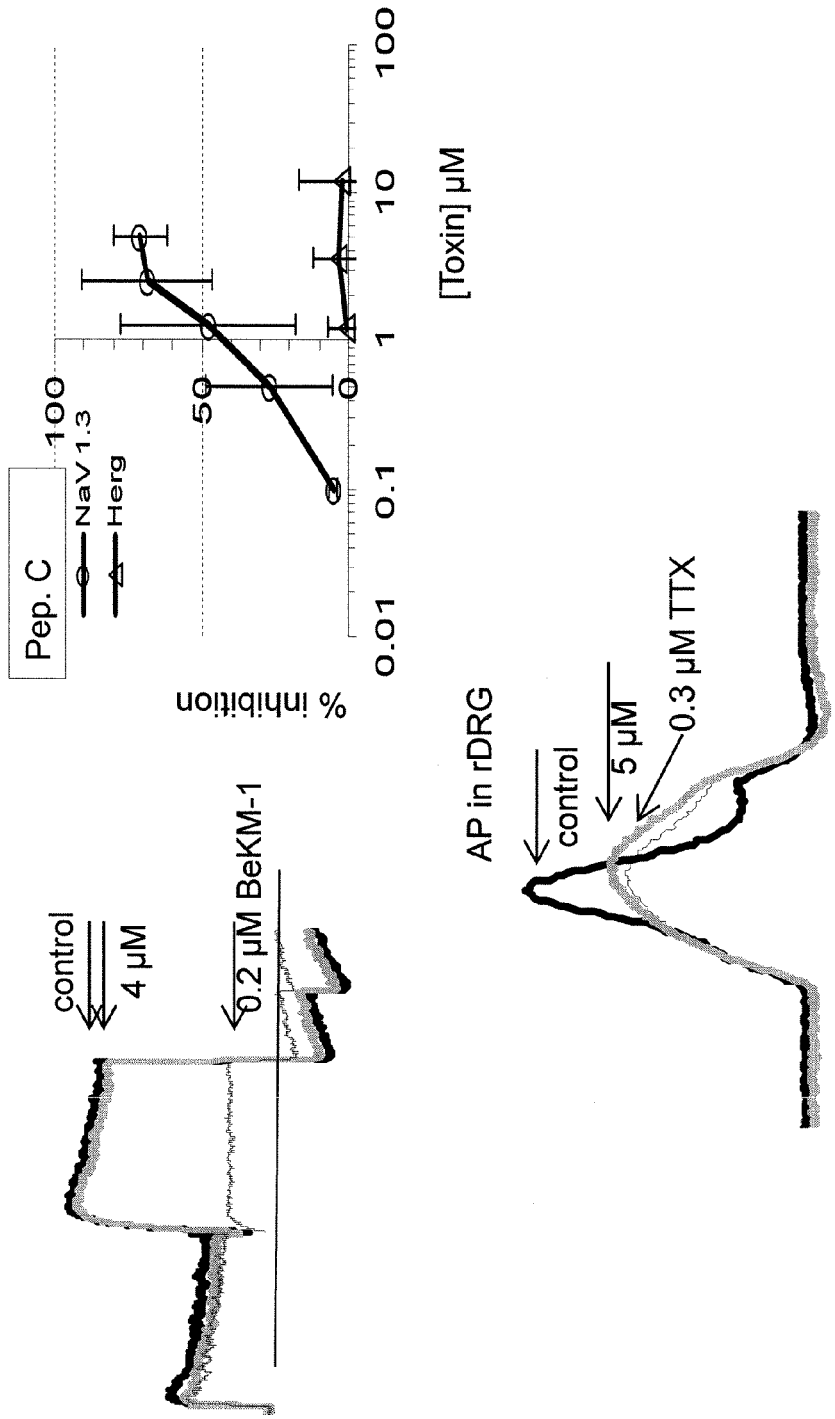
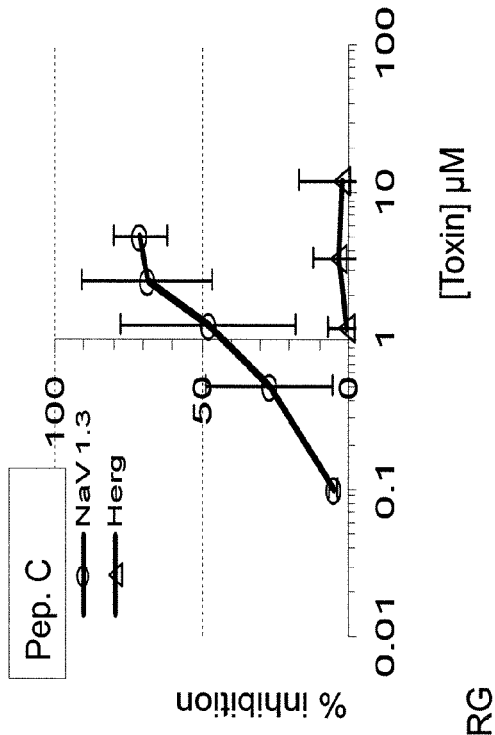
Fig. 9E Dose response
Fig. 9D hK$_V$11.1
Fig. 9F

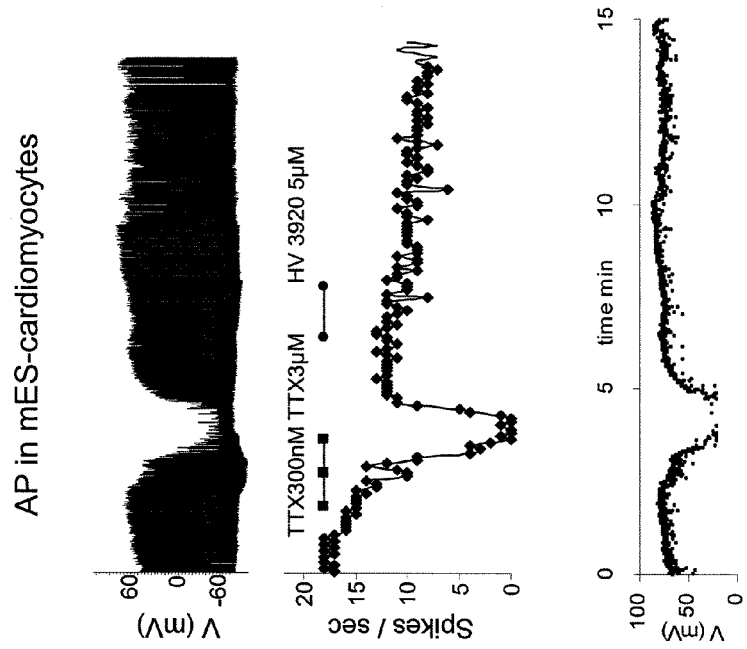
Fig. 9H
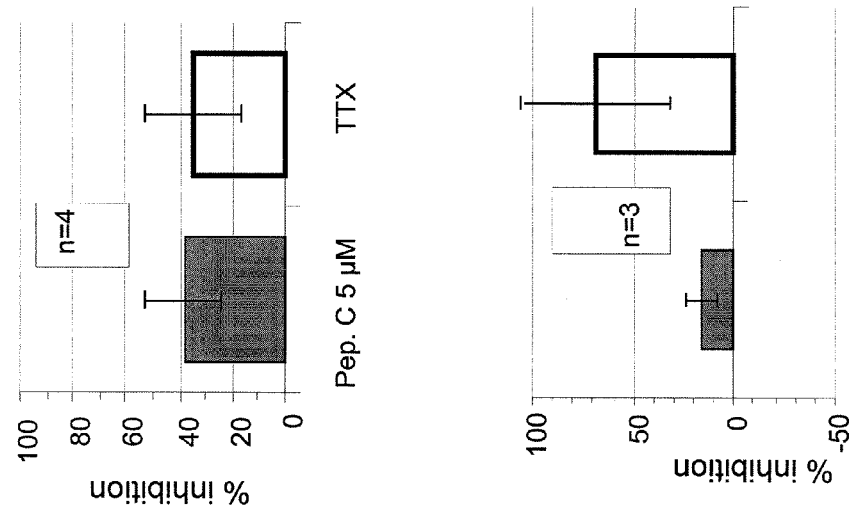
Fig. 9G
Fig. 9I

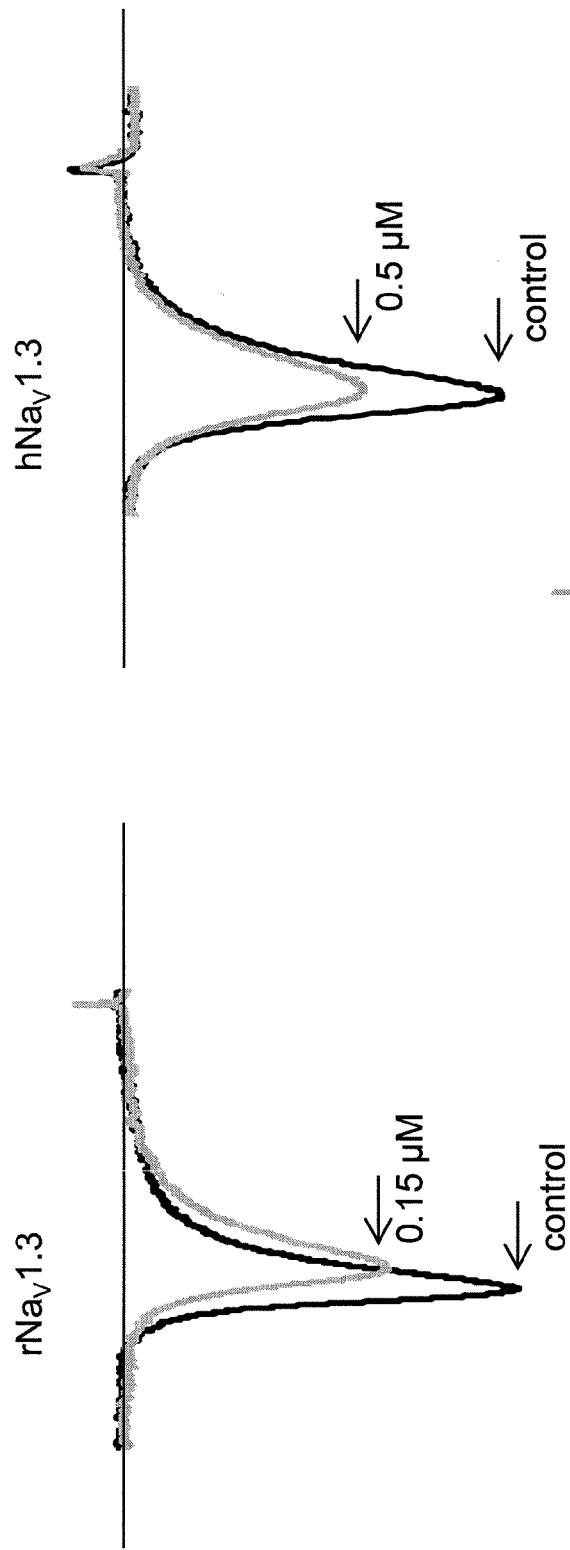
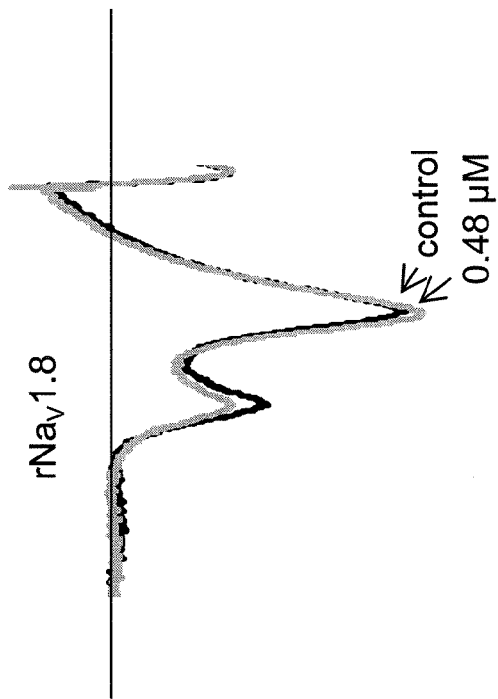
Fig. 10A rNa_v1.3
Fig. 10B hNa_v1.3
Fig. 10C rNa_v1.8

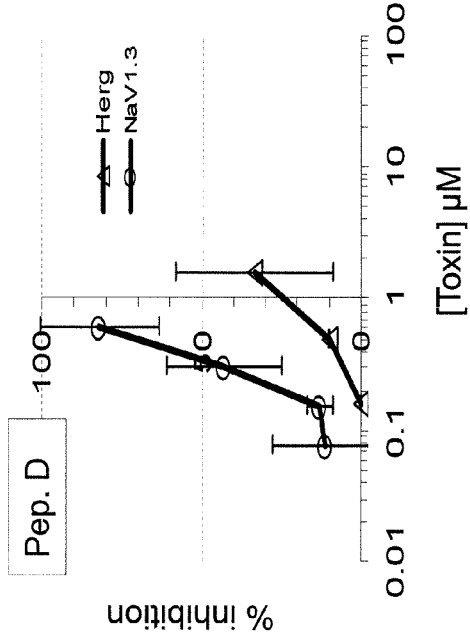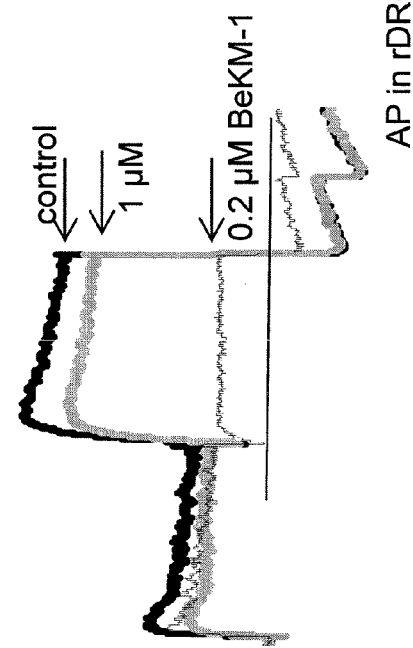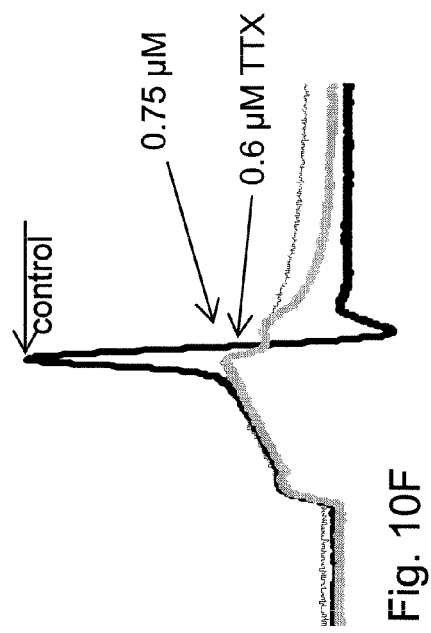

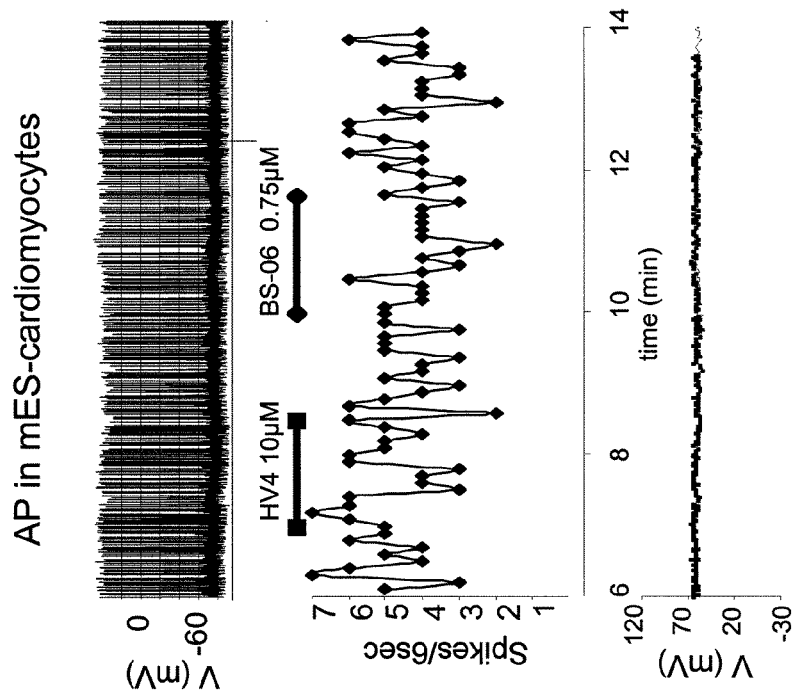
Fig. 10H
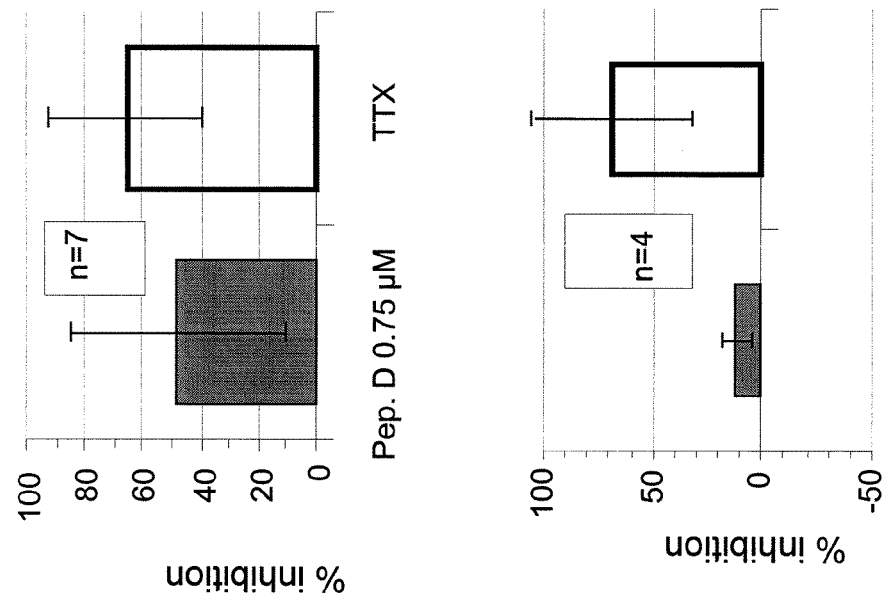
Fig. 10G
Fig. 10I

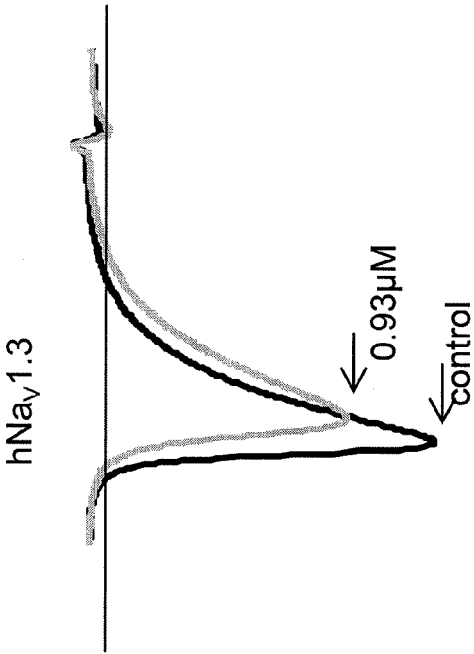
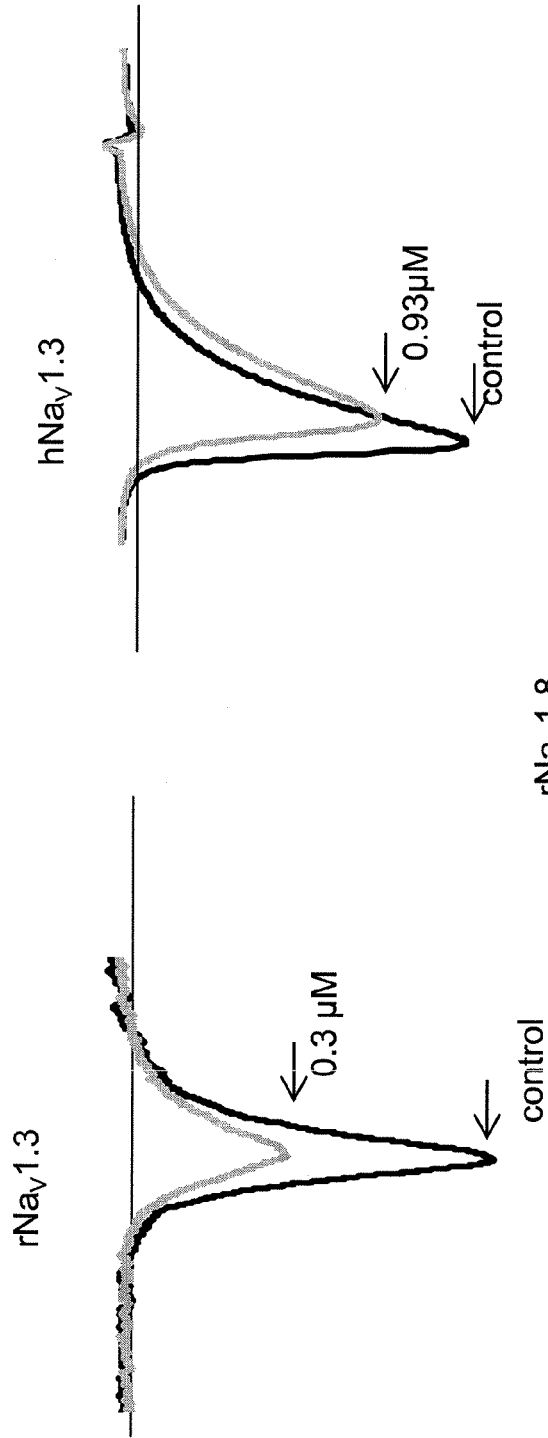
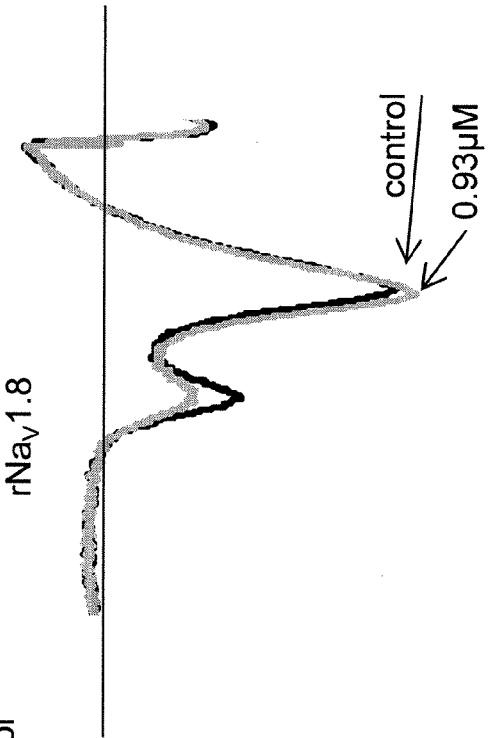
Fig. 11A
Fig. 11B
Fig. 11C

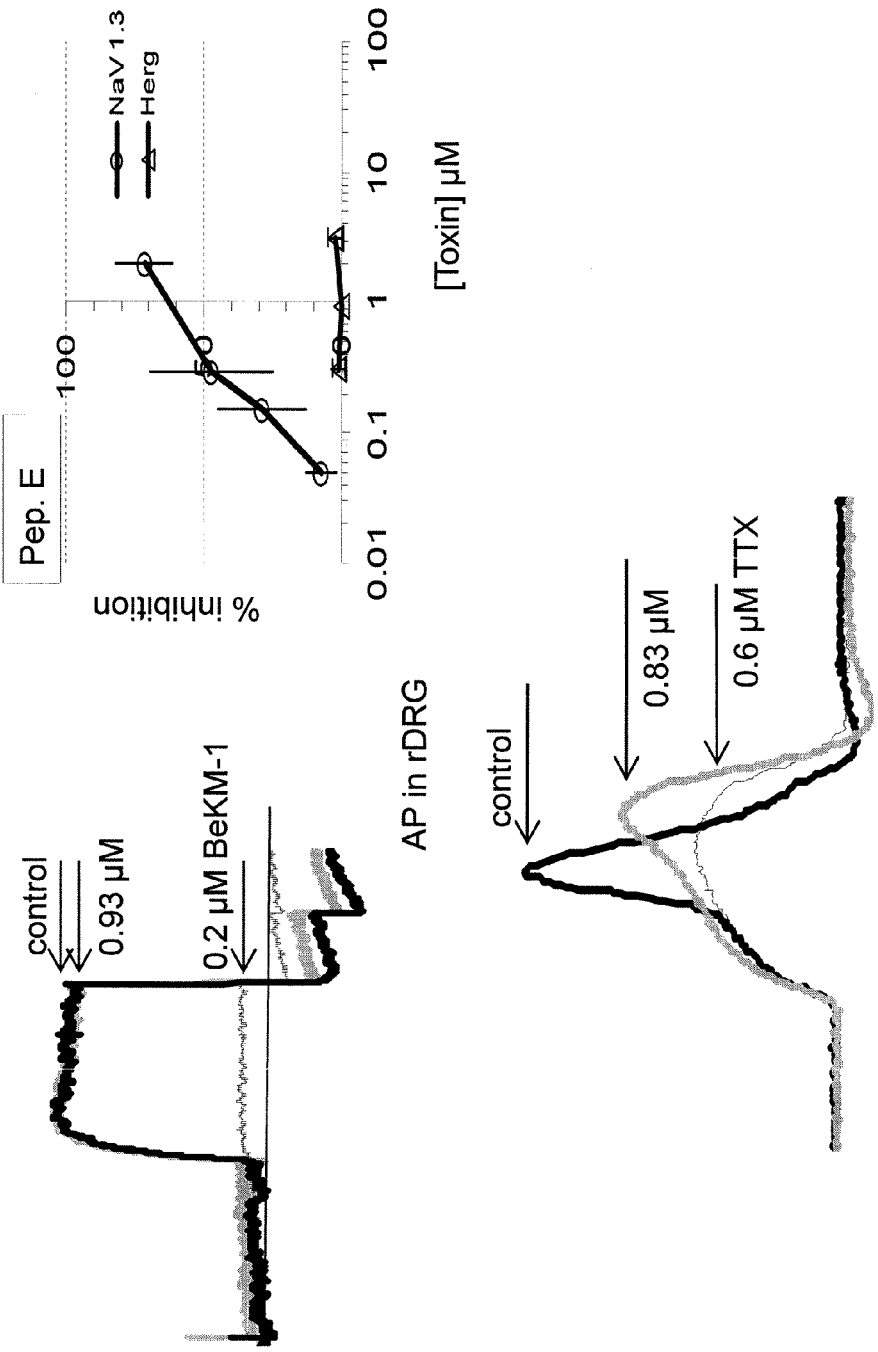

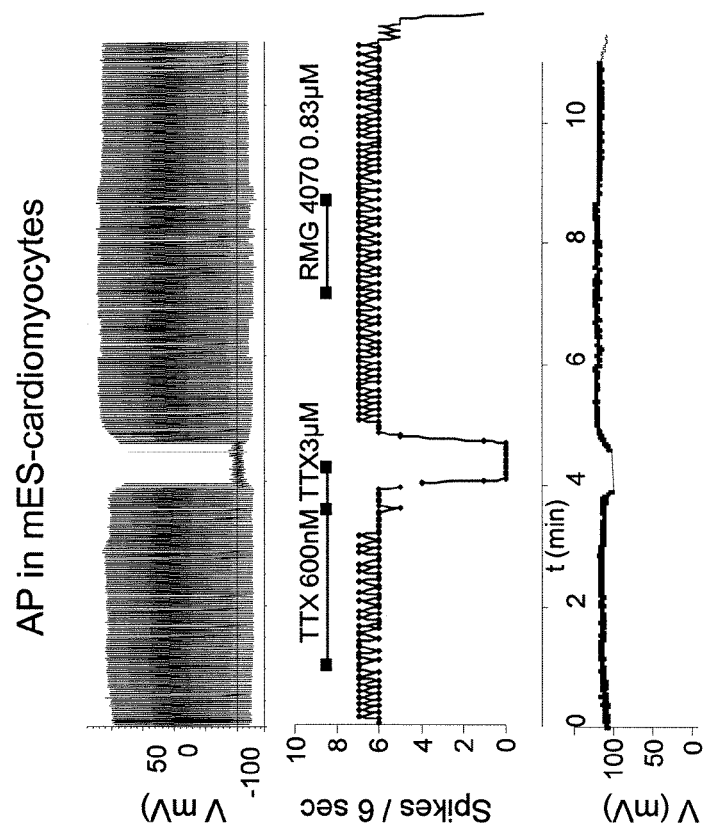
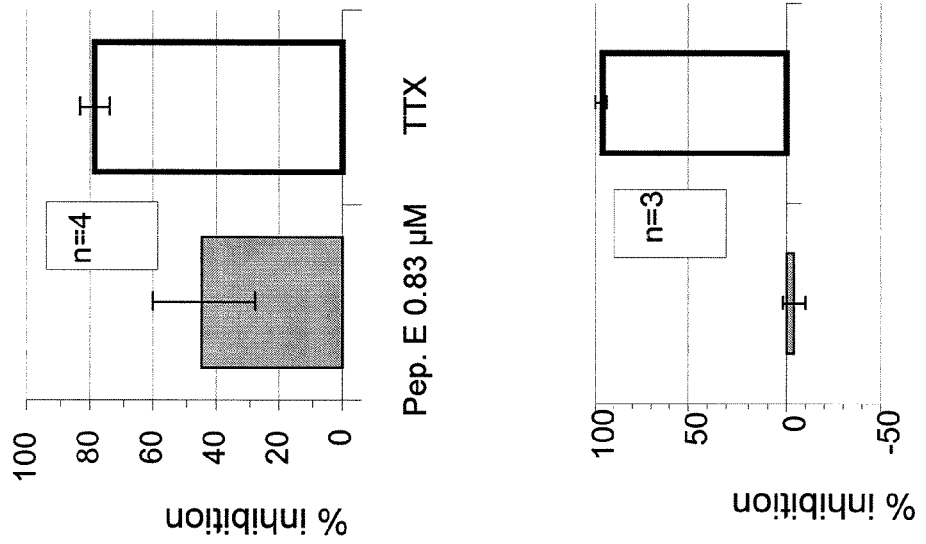

rNa$_v$1.3 hNa$_v$1.3 rNa$_v$1.8

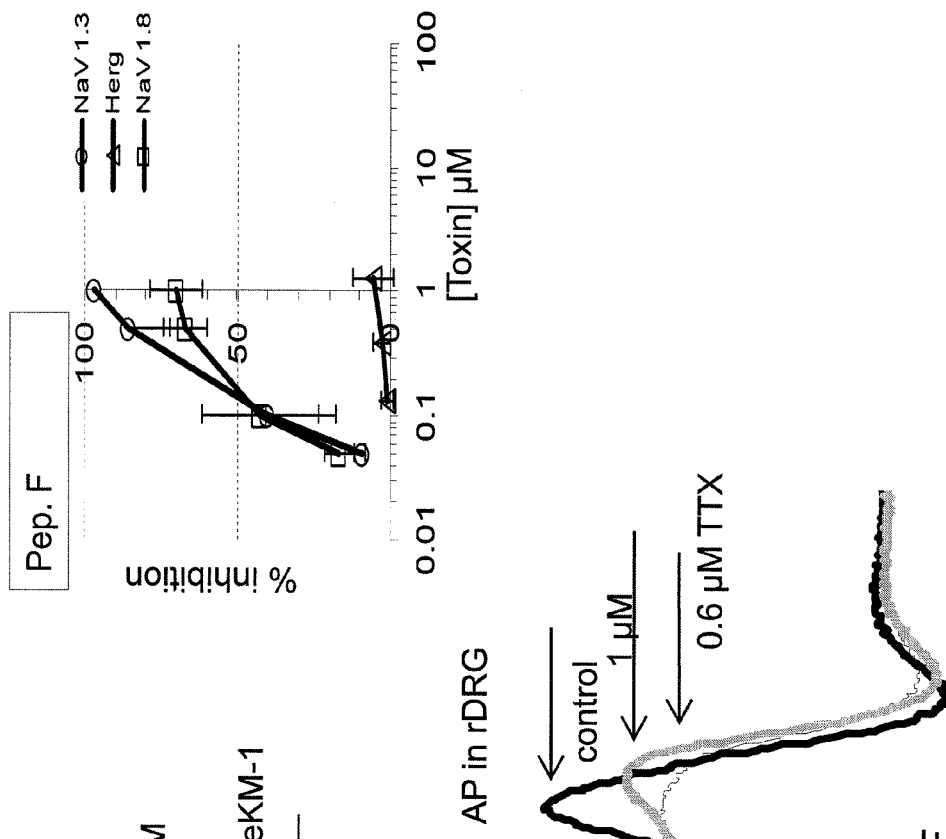
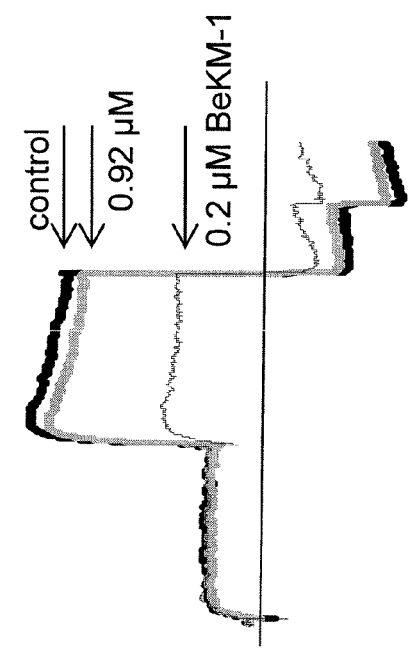
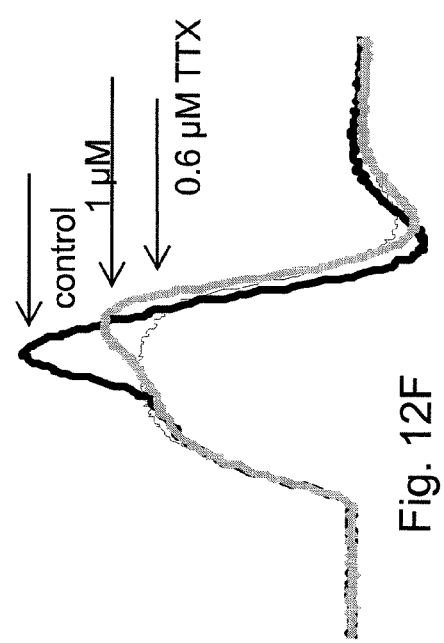

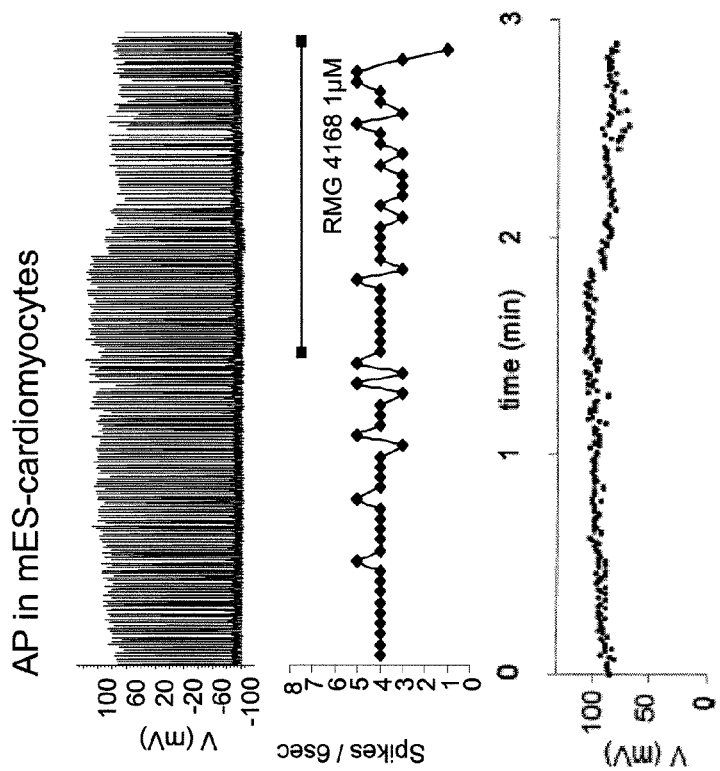
Fig. 12H
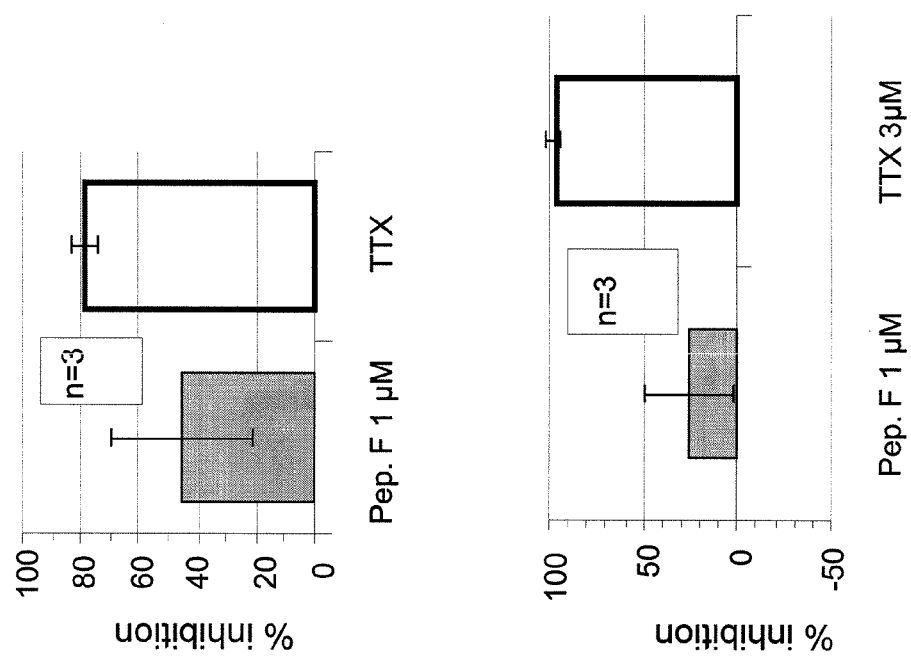
Fig. 12G
Fig. 12I

```
                         SEQUENCE LISTING

<160> NUMBER OF SEQ ID NOS: 9

<210> SEQ ID NO 1
<211> LENGTH: 34
<212> TYPE: PRT
<213> ORGANISM: Pterinochilus spp. Usambara (Psp)
<220> FEATURE:
<221> NAME/KEY: MISC_FEATURE
<222> LOCATION: (34)..(34)
<223> OTHER INFORMATION: amidation may or may not occur at this location

<400> SEQUENCE: 1

Asp Asp Cys Leu Gly Met Phe Ser Ser Cys Asp Pro Asp Asn Asp Lys
1               5                   10                  15

Cys Cys Glu Gly Arg Lys Cys Asn Arg Lys Asp Lys Trp Cys Lys Tyr
            20                  25                  30

Val Leu

<210> SEQ ID NO 2
<211> LENGTH: 29
<212> TYPE: PRT
<213> ORGANISM: Pterinochilus spp. Usambara (Psp)
<220> FEATURE:
<221> NAME/KEY: MISC_FEATURE
<222> LOCATION: (29)..(29)
<223> OTHER INFORMATION: amidation may or may not occur at this location

<400> SEQUENCE: 2

Tyr Cys Gln Glu Phe Leu Trp Thr Cys Asp Glu Glu Arg Lys Cys Cys
1               5                   10                  15

Gly Asp Met Val Cys Arg Leu Trp Cys Lys Lys Arg Leu
            20                  25

<210> SEQ ID NO 3
```

-continued

```
<211> LENGTH: 35
<212> TYPE: PRT
<213> ORGANISM: Haplopelma Lividum (Hv)
<220> FEATURE:
<221> NAME/KEY: MISC_FEATURE
<222> LOCATION: (35)..(35)
<223> OTHER INFORMATION: amidation may or may not occur at this location

<400> SEQUENCE: 3

Ala Cys Leu Gly Phe Gly Glu Lys Cys Asn Pro Ser Asn Asp Lys Cys
1               5                   10                  15

Cys Lys Ser Ser Ser Leu Val Cys Ser Gln Lys His Lys Trp Cys Lys
            20                  25                  30

Tyr Gly Trp
        35

<210> SEQ ID NO 4
<211> LENGTH: 33
<212> TYPE: PRT
<213> ORGANISM: Haplopelma Lividum (Hv)
<220> FEATURE:
<221> NAME/KEY: MISC_FEATURE
<222> LOCATION: (33)..(33)
<223> OTHER INFORMATION: amidation may or may not occur at this location

<400> SEQUENCE: 4

Ala Cys Lys Gly Leu Phe Val Thr Cys Thr Pro Gly Lys Asp Glu Cys
1               5                   10                  15

Cys Pro Asn His Val Cys Ser Ser Lys His Lys Trp Cys Lys Tyr Lys
            20                  25                  30

Thr

<210> SEQ ID NO 5
<211> LENGTH: 34
<212> TYPE: PRT
<213> ORGANISM: Red Morph Grammostola (RMG)
<220> FEATURE:
<221> NAME/KEY: MISC_FEATURE
<222> LOCATION: (34)..(34)
<223> OTHER INFORMATION: amidation may or may not occur at this location

<400> SEQUENCE: 5

Asp Cys Leu Gly Phe Met Arg Lys Cys Ile Pro Asp Asn Asp Lys Cys
1               5                   10                  15

Cys Arg Pro Asn Leu Val Cys Ser Arg Thr His Lys Trp Cys Lys Tyr
            20                  25                  30

Val Phe

<210> SEQ ID NO 6
<211> LENGTH: 34
<212> TYPE: PRT
<213> ORGANISM: Red Morph Grammostola (RMG)

<400> SEQUENCE: 6

Asp Cys Leu Gly Trp Phe Lys Gly Cys Asp Pro Asp Asn Asp Lys Cys
1               5                   10                  15

Cys Glu Gly Tyr Lys Cys Asn Arg Arg Asp Lys Trp Cys Lys Tyr Lys
            20                  25                  30

Leu Trp

<210> SEQ ID NO 7
<211> LENGTH: 17
<212> TYPE: PRT
<213> ORGANISM: Artificial Sequence
```

```
<220> FEATURE:
<223> OTHER INFORMATION: synthetic construct of spider venom obtainable,
      for example, by solid phase synthetic procedures by chemical
      synthesis using BOC (t-Butyloxycarbonyl), Fmoc (9-
      Fluorenylmethyloxycarbonyl) solid-phase peptide synthesis or any
      other known method
<220> FEATURE:
<221> NAME/KEY: MISC_FEATURE
<222> LOCATION: (5)..(5)
<223> OTHER INFORMATION: Xaa is amino acid M or F
<220> FEATURE:
<221> NAME/KEY: MISC_FEATURE
<222> LOCATION: (6)..(6)
<223> OTHER INFORMATION: Xaa is amino acid M or F
<220> FEATURE:
<221> NAME/KEY: MISC_FEATURE
<222> LOCATION: (7)..(7)
<223> OTHER INFORMATION: Xaa is amino acid R or S
<220> FEATURE:
<221> NAME/KEY: MISC_FEATURE
<222> LOCATION: (8)..(8)
<223> OTHER INFORMATION: Xaa is amino acid K or S
<220> FEATURE:
<221> NAME/KEY: MISC_FEATURE
<222> LOCATION: (10)..(10)
<223> OTHER INFORMATION: Xaa is amino acid D or I
<220> FEATURE:
<221> NAME/KEY: MISC_FEATURE
<222> LOCATION: (16)..(16)
<223> OTHER INFORMATION: amidation may or may not occur at this location

<400> SEQUENCE: 7

Asp Cys Leu Gly Xaa Xaa Xaa Xaa Cys Xaa Pro Asp Asn Asp Lys Cys
1               5                   10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: synthetic construct of spider venom obtainable,
      for example, by solid phase synthetic procedures by chemical
      synthesis using BOC (t-Butyloxycarbonyl), Fmoc (9-
      Fluorenylmethyloxycarbonyl) solid-phase peptide synthesis or any
      other known method
<220> FEATURE:
<221> NAME/KEY: MISC_FEATURE
<222> LOCATION: (3)..(3)
<223> OTHER INFORMATION: Xaa is amino acid K or L
<220> FEATURE:
<221> NAME/KEY: MISC_FEATURE
<222> LOCATION: (5)..(5)
<223> OTHER INFORMATION: Xaa is amino acid L or F
<220> FEATURE:
<221> NAME/KEY: MISC_FEATURE
<222> LOCATION: (6)..(6)
<223> OTHER INFORMATION: Xaa is amino acid G or F
<220> FEATURE:
<221> NAME/KEY: MISC_FEATURE
<222> LOCATION: (7)..(7)
<223> OTHER INFORMATION: Xaa is amino acid E or V
<220> FEATURE:
<221> NAME/KEY: MISC_FEATURE
<222> LOCATION: (8)..(8)
<223> OTHER INFORMATION: Xaa is amino acid K or T
<220> FEATURE:
<221> NAME/KEY: MISC_FEATURE
<222> LOCATION: (10)..(10)
<223> OTHER INFORMATION: Xaa is amino acid N or T
<220> FEATURE:
<221> NAME/KEY: MISC_FEATURE
<222> LOCATION: (12)..(12)
<223> OTHER INFORMATION: Xaa is amino acid S or G
<220> FEATURE:
<221> NAME/KEY: MISC_FEATURE
<222> LOCATION: (13)..(13)
```

```
<223> OTHER INFORMATION: Xaa is amino acid N or K
<220> FEATURE:
<221> NAME/KEY: MISC_FEATURE
<222> LOCATION: (15)..(15)
<223> OTHER INFORMATION: Xaa is amino acid K or E
<220> FEATURE:
<221> NAME/KEY: MISC_FEATURE
<222> LOCATION: (17)..(17)
<223> OTHER INFORMATION: amidation may or may not occur at this location

<400> SEQUENCE: 8

Ala Cys Xaa Gly Xaa Xaa Xaa Xaa Cys Xaa Pro Xaa Xaa Asp Xaa Cys
 1               5                  10                  15

Cys

<210> SEQ ID NO 9
<211> LENGTH: 12
<212> TYPE: PRT
<213> ORGANISM: Artificial Sequence
<220> FEATURE:
<223> OTHER INFORMATION: synthetic construct of spider venom obtainable,
      for example, by solid phase synthetic procedures by chemical
      synthesis using BOC (t-Butyloxycarbonyl), Fmoc (9-
      Fluorenylmethyloxycarbonyl) solid-phase peptide synthesis or any
      other known method
<220> FEATURE:
<221> NAME/KEY: MISC_FEATURE
<222> LOCATION: (1)..(1)
<223> OTHER INFORMATION: Xaa is amino acid L or H
<220> FEATURE:
<221> NAME/KEY: MISC_FEATURE
<222> LOCATION: (5)..(5)
<223> OTHER INFORMATION: Xaa is amino acid Q, S, or R
<220> FEATURE:
<221> NAME/KEY: MISC_FEATURE
<222> LOCATION: (6)..(6)
<223> OTHER INFORMATION: Xaa is amino acid K or T
<220> FEATURE:
<221> NAME/KEY: MISC_FEATURE
<222> LOCATION: (12)..(12)
<223> OTHER INFORMATION: amidation may or may not occur at this location

<400> SEQUENCE: 9

Xaa Val Cys Ser Xaa Xaa His Lys Trp Cys Lys Tyr
 1               5                  10
```

PEPTIDES ISOLATED FROM SPIDER VENOM, AND USES THEREOF

This is a Non-Provisional Application, filed Sep. 14, 2010, an application claiming the benefit under 35 U.S.C. 119(e) U.S. Provisional Application No. 61/272,336, filed Sep. 15, 2009, the content of which is hereby incorporated by reference in its entirety.

FIELD

The presently described subject matter relates to isolated spider venom peptides, which are used as a potent and selective ion channel blockers and to a composition and methods for treatment of neuropathic pain.

"The Sequence Listing submitted in text format (.txt) on Sep. 14, 2010, named "30346_ST25.txt, (created on Monday, Sep. 13, 2010, 6.16 KB), is incorporated herein by reference."

BACKGROUND

Voltage dependent sodium ($Na_V1$) and in some cases low voltage activated calcium ($Ca_V3$) channels are membrane proteins that in all excitable cells including neurons, lay in the basis of action potential generation and propagation Inhibition of $Na_V1$ channels causes a neuron to be incapable of firing action potentials and therefore incapable of encoding and transmitting information.

Neuropathic pain is a compound neuronal process involving both peripheral hyperexcitability and central sensitization. Peripheral hyperexcitability could be due to ectopic spontaneous firing of damaged dorsal root ganglion (DRG) neurons which is transmitted to the central nervous system (CNS) and sensed as pain. Tackling this phenomenon by specifically inhibiting $Na_V1$ (or $Ca_V3$) channels in damaged sensory nociceptive neurons in the periphery may be effective in reducing or eliminating neuropathic pain. This could be achieved by either local application of non-specific $Na_V$ blockers (such as local anesthetics) or by systemic application of $Na_V1$ blockers, which specifically recognize $Na_V1$ channels in DRG neuron membranes. One generic approach to increase this specificity is by avoiding the CNS (in which most $Na_V1$ isoforms are crucial for neuronal activity). The other approach is to find selective blockers to $Na_V1$ isoforms, which expression is restricted to hyperexcitable DRG neurons (Devor, 2006; Cummins et al. 2007). One of the main issues regarding $Na_V1$ blockers specificity is avoidance of cardiac blockade activity.

The Tetrodotoxin (TTX)-sensitive, $Na_V1.3$, channel is normally expressed in the CNS and the peripheral nervous system (PNS) during the embryonic stage and its expression is heavily down regulated with maturation. However, up-regulation of the channel expression is reported following neuronal injury. These observations, suggest that specifically targeting $Na_V1.3$ isoforms, could block exclusively damaged-hyperexcitable DRG neurons (Devor, 2006; Cummins et al. 2007).

The TTX-resistant, $Na_V1.8$ channel is expressed almost exclusively in the PNS and has been shown to mediate most of the well documented TTX resistant component of DRG neurons action potentials. Recently, a paper has been published, emphasizing the importance of $Na_V1.8$ channels as a target in pain control (Jarvis, M. F., et al. 2007; Zimmermann, K., et al. 2007).

The importance of treating pain, by targeting a protein which is expressed specifically in the periphery is highlighted by the case of ASIC1 channels which are expressed in the spinal cord and their inhibition induces analgesia in a rat model of neuropathic pain. However, administration of the peptide modulator, should be direct as in systemic administration the peptides do not cross the blood brain barrier to reach their target protein (Mazzuca, M., et al. 2007, Nat. Neurosci. 10, 943).

Throughout this specification, various scientific publications and patents or published patent applications are referenced. The disclosure of all these publications in their entireties is hereby incorporated by reference into this specification in order to more fully describe the state of the art to which this invention pertains. Citation or identification of any reference in this section or any other part of this application shall not be construed as an admission that such reference is available as prior art to the invention.

SUMMARY

Provided is peptide isolated from spider venom. Also provided is an isolated synthetic spider venom peptide. Suitable spiders can include tarantula species.

In an embodiment, the purified or isolated peptide according to the presently described subject matter can comprise or consist of an amino acid sequence having from 2 to 50 consecutive amino acids, from 10 to 50 consecutive amino acids, from 20 to 50 consecutive amino acids, from 25 to 45 consecutive amino acids, from 29 to 40 consecutive amino acids, from 29 to 35 consecutive amino acids, at least 29 and at most 35 consecutive amino acids.

In a further embodiment, the purified or isolated peptide according to the presently described subject matter has a molecular weight in the range of from 3000 to 5000 daltons, from 3250 to 4750 daltons, from 3500 to 4500 daltons, from 3550 to 4300 daltons, or from 3600 to 4250 daltons.

In an embodiment, the presently described peptide can exhibit ion channel inhibiting activity. The ion channel can be a sodium ion channel or a calcium ion channel.

In still a further embodiment, the presently described subject matter provides a purified or isolated peptide comprising a sequence comprising, consisting of, or found within, the sequence of any one of SEQ ID NO: 1, SEQ ID NO: 2, SEQ ID NO: 3, SEQ ID NO: 4, SEQ ID NO: 5, or SEQ ID NO: 6; or a sequence obtained by (i) replacement of one or more of the amino acid residues of any one of SEQ ID NO: 1, SEQ ID NO: 2, SEQ ID NO: 3, SEQ ID NO: 4, SEQ ID NO: 5, or SEQ ID NO: 6 by different amino acid residues, (ii) deletion of one or more amino acid residues from any one of SEQ ID NO: 1, SEQ ID NO: 2, SEQ ID NO: 3, SEQ ID NO: 4, SEQ ID NO: 5, or SEQ ID NO: 6, and/or (iii) addition of one or more amino acid residues to any one of SEQ ID NO: 1, SEQ ID NO: 2, SEQ ID NO: 3, SEQ ID NO: 4, SEQ ID NO: 5, or SEQ ID NO: 6, or a salt or a chemical derivative of the peptide. One or more with regard to deletion, replacement or addition, can refer to from 1 to 10, from 1 to 8, from 1 to 6, from 1 to 4, from 1 to 2, or 1. In an embodiment, ion channel blocking activity is maintained.

The purified or isolated peptide according to the presently described subject matter can comprise or consist of one or more amino acid sequences including, for example, DDCLG-MFSSCDPDNDKCCEGRKCNKDKWCKYVL (SEQ ID NO: 1), YCQEFLWTCDEERKCCGDMVCRLWCKKRL (SEQ ID NO: 2), ACLGFGEKCNPSNDKCCKSSSLVC-SQKHKWCKYGW (SEQ ID NO: 3), ACKGLFVTCTPGK-DECCPNHVCSSKHKWCKYKI (SEQ ID NO: 4), DCLG-FMRKCIPDNDKCCRPNLVCSRTHKWCKYVF (SEQ ID NO: 5) and DCLGWFKGCDPDNDKCCEGYKCNRRDK-WCKYKLW (SEQ ID NO: 6). Alternatively, the peptide can comprise or consist of a C-terminally amidated form of an amino acid sequence represented by SEQ ID NO: 1, SEQ ID NO: 2, SEQ ID NO: 3, SEQ ID NO: 4, SEQ ID NO: 5 or SEQ ID NO: 6. In particular, the peptide can comprise or consist of a C-terminally amidated form of an amino acid sequence represented by SEQ ID NO: 1, SEQ ID NO: 2, SEQ ID NO: 4 or SEQ ID NO: 5. When the peptide comprises or consists of an amino acid sequence represented by SEQ ID NO: 6, the spider venom can be Red Morph *Grammostola* (RMG) venom and not Brown Morph *Grammostola* (BMG).

In another embodiment, the presently described subject matter provides a purified or isolated peptide having from 20 to 40 consecutive amino acids comprising the sequence DCLGX$_1$X$_2$X$_3$X$_4$CX$_5$PDNDKCC (SEQ ID NO: 7); wherein X$_1$ is M or F; X$_2$ is M or F; X$_3$ is R or S; X$_4$ is K or S; and X$_5$ is D or 1, and the peptide exhibits ion channel inhibiting activity. The ion channel can be a sodium ion channel or a calcium ion channel. The peptide can be purified from spider venom or can be an isolated synthetic spider venom peptide.

In an embodiment, the presently described subject matter provides a purified or isolated peptide having from 20 to 40 consecutive amino acids comprising the sequence ACX$_6$GX$_7$X$_8$X$_9$X$_{10}$CX$_{11}$PX$_{12}$X$_{13}$DX$_{14}$CC (SEQ ID NO: 8); wherein X$_6$ is K or L; X$_7$ is L or F; X$_8$ is G or F; X$_9$ is E, or V; X$_{10}$ is K or T; X$_{11}$ is N or T; X$_{12}$ is S or G; X$_{13}$ is N or K; and X$_{14}$ is K or E, and the peptide exhibits ion channel inhibiting activity. The ion channel can be a sodium ion channel or a calcium ion channel. The peptide can be purified from spider venom or can be an isolated synthetic spider venom peptide.

In a further embodiment, the presently described subject matter provides a purified or isolated peptide having from 20 to 40 consecutive amino acids comprising the sequence X$_{15}$VCSX$_{16}$X$_{17}$HKWCKY (SEQ ID NO: 9); wherein X$_{15}$ is L or H; X$_{16}$ is Q, S, or R; and X$_{17}$ is K or T, and the peptide exhibits ion channel inhibiting activity. The ion channel can be a sodium ion channel or a calcium ion channel. The peptide can be purified from spider venom or can be an isolated synthetic spider venom peptide.

In still a further embodiment, according to the presently described subject matter, an ion channel inhibitor is provided that can comprise or consist of any one or more of the presently described peptides or a salt thereof. The ion channel can be a sodium ion channel or a calcium ion channel.

Accordingly to the presently described subject matter, a pharmaceutical composition is provided that can comprise or consist of a peptide comprising, consisting of, or found within, one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9; and a pharmaceutically acceptable carrier or diluent. In an embodiment, the carrier can be an aqueous carrier. In an embodiment the peptide can comprise or consist of one or more amino acid sequences represented by a C-terminally amidated form of an amino acid sequence represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In one embodiment, the peptide can comprise or consist of one or more amino acid sequences represented by a C-terminally amidated form of an amino acid sequence represented by SEQ ID NO: 1, SEQ ID NO: 2, SEQ ID NO: 4 or SEQ ID NO: 5. When the peptide comprises or consists of an amino acid sequence represented by SEQ ID NO: 6, the spider venom can be Red Morph *Grammostola* (RMG) venom and not Brown Morph *Grammostola* (BMG).

In an embodiment, accordingly to the presently described subject matter, a method of treating pain in a subject is provided that can comprise or consist of administering to a subject in need thereof, a therapeutically effective amount of a peptide comprising, consisting of, or found within, one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and/or a pharmaceutically acceptable salt thereof. In an embodiment the peptide can comprise or consist of one or more amino acid sequences represented by a C-terminally amidated form of an amino acid sequence represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In another embodiment, the peptide can comprise or consist of one or more amino acid sequences represented by a C-terminally amidated form of an amino acid sequence represented by SEQ ID NO: 1, SEQ ID NO: 2, SEQ ID NO: 4 or SEQ ID NO: 5. In a further embodiment, the therapeutically effective amount can comprise an analgesic or anti-inflammatory effective amount. When the peptide comprises or consists of an amino acid sequence represented by SEQ ID NO: 6, the spider venom can be Red Morph *Grammostola* (RMG) venom and not Brown Morph *Grammostola* (BMG).

In another embodiment, accordingly to the presently described subject matter, a method of treating pain in a subject is provided that can comprise or consist of administering to a subject in need thereof, a therapeutically effective amount of a pharmaceutical composition comprising or consisting of a peptide comprising, consisting of, or found within, one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and/or a pharmaceutically acceptable salt thereof; and a pharmaceutically acceptable carrier or diluent. In an embodiment the peptide can comprise or consist of one or more amino acid sequences represented by a C-terminally amidated form of an amino acid sequence represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In another embodiment, the peptide can comprise or consist of one or more amino acid sequences represented by a C-terminally amidated form of an amino acid sequence represented by SEQ ID NO: 1, SEQ ID NO: 2, SEQ ID NO: 4 or SEQ ID NO: 5. In a further embodiment, the therapeutically effective amount can comprise an analgesic or anti-inflammatory effective amount. When the peptide comprises or consists of an amino acid sequence represented by SEQ ID NO: 6, the spider venom can be Red Morph *Grammostola* (RMG) venom and not Brown Morph *Grammostola* (BMG).

In a further embodiment, the presently described subject matter provides a method for inhibiting ion channel activity in a subject, comprising administering to the subject an effective amount of the presently described pharmaceutical composition, wherein the ion channel activity is inhibited without impairing cardiac function.

Also provided is a method of blocking an Na$_V$ channel in a subject. The method can comprise or consist of administering to a subject in need thereof a therapeutically effective amount of a peptide or a pharmaceutical composition comprising or consisting of a peptide comprising, consisting of, or found within, one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and/or a pharmaceutically acceptable salt thereof; and a pharmaceutically acceptable carrier or diluent. In an embodiment the peptide can comprise or consist of one or more amino acid sequences represented by a C-terminally amidated form of an amino acid sequence represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In another embodiment, the peptide can comprise or consist of one or more amino acid sequences represented by a C-terminally amidated form of an amino acid sequence represented by SEQ ID NO: 1, SEQ ID NO: 2, SEQ ID NO: 4 or SEQ ID NO: 5. In a further embodiment, the therapeutically effective amount can comprise an analgesic or anti-inflammatory effective amount. When the peptide comprises or consists of an amino acid sequence represented by SEQ ID NO: 6, the spider venom can be Red Morph *Grammostola* (RMG) venom and not Brown Morph *Grammostola* (BMG).

According to the presently described subject matter, provided is a pharmaceutical composition for topical, injectable, rectal, intranasal, pulmonary, oral, parenteral or enteral administration to a subject. The pharmaceutical composition can be administered by inhalation or infusion. The pharmaceutical composition can comprise a dosage formulation including, but not limited to, an injectable formulation, an aqueous solution, a liquid, an emulsion, a gel, a lotion, a cream, an ointment, a tablet, a capsule, a gel-capsule, and a suppository.

In yet another embodiment the pharmaceutical composition can comprise a liquid formulation for oral, parenteral, or enteral administration. The liquid formulation can comprise an aqueous formulation.

The pain treated by any method described herein can be any known type of pain, including peripheral pain. For example, the pain to be treated can be one or more pain described as neurogenic pain, neuropathic pain, cancer pain, post-surgical pain, oral or dental pain, pain from referred trigeminal neuralgia, pain from post-herpetic neuralgia, or pain due to reflex sympathetic dystrophy and/or pain associated with an inflammatory condition.

The pain can be characterized as, for example, nociceptive pain, non-nociceptive pain, somatic pain, visceral pain, nerve pain. The pain can be the result of stimulation of receptors that respond to heat, cold, vibration, stretch, as well as chemical stimuli released from damaged cells. In addition the pain can be the result of pain generated by nerve cell dysfunction. According to the present subject matter the pain can be pain associated with tissues such as skin, muscle, joints, bones, and ligaments—often known as musculo-skeletal pain. The pain can also be pain associated with the internal organs of the main body cavities. In this regard, the pain can be associated with the thorax (heart and lungs), the abdomen (liver, kidneys, spleen and bowels), and/or the pelvis (bladder, womb, and ovaries). Additionally, the pain according to the present subject matter can be pain associated with the nervous system itself, e.g., pain associated with a pinched nerve or a trapped nerve. The pain can originate from the peripheral nervous system, i.e., the nerves between the tissues and the spinal cord, or from the central nervous system, i.e., the nerves between the spinal cord and the brain. The pain can be associated with, for example nerve degeneration due to multiple sclerosis, stroke, brain haemorrhage and/or oxygen starvation, nerve pressure, a trapped nerve, nerve inflammation, a torn or slipped disc and/or a nerve infection, such a shingles or other viral infections.

According to the presently described subject matter, the inflammatory condition can be associated with one or more conditions selected from the group consisting of acute pain, migraine, headache pain, migraine headache, traumatic nerve injury, nerve compression, nerve entrapment, postherpetic neuralgia, trigeminal neuralgia, diabetic neuropathy, chronic lower back pain, phantom limb pain, chronic pelvic pain, neuroma pain, complex regional pain syndrome, chronic arthritic pain, and pain associated with cancer, chemotherapy, HIV and HIV treatment-induced neuropathy, irritable bowel syndrome and related disorders and Crohns disease.

Further, provided is a method for isolating a peptide from spider venom, comprising or consisting of one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, that can comprise centrifuging lyophilized crude spider venom to obtain centrifuged venom, filtering the centrifuged venom to obtain filtered venom, loading the filtered venom on a gel filtration column, and eluting the column to obtain a fraction containing the isolated peptide, which can be further purified using cation exchange and/or HPLC chromatography. When the peptide comprises or consists of an amino acid sequence represented by SEQ ID NO: 6, the spider venom can be Red Morph *Grammostola* (RMG) venom and not Brown Morph *Grammostola* (BMG).

Additionally, a method for isolating a peptide from spider venom comprises or consists of one or more amino acid sequences represented by any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, is provided. When the peptide comprises or consists of an amino acid sequence represented by SEQ ID NO: 6, the spider venom can be Red Morph *Grammostola* (RMG) venom and not Brown Morph *Grammostola* (BMG). The method that can comprise centrifuging lyophilized crude spider venom to obtain centrifuged venom, filtering the centrifuged venom to obtain filtered venom, loading the filtered venom on a gel filtration column, and eluting the column to obtain a fraction containing the isolated peptide, to be further purified using cation exchange and/or HPLC chromatography.

In yet another embodiment, a method for refolding a peptide is provided, where the method comprises or consists of collecting crude peptides at concentrations of 1.1 mM to 24 mM; solubilizing the crude peptide, for example, in 0.1M Tris buffer or in 2M NH$_4$OAC buffer; reducing the peptide, for example, with 20 mM DTT; folding the peptide, for example, in a redox mixture containing a reduced and/or oxidized cysteine or glutathione system in buffered aqueous solution at a pH in the range of from 7 to 9.5 and at a final peptide concentration of 10-27.5 µM; and purifying the folded peptide, for example, on a semi-preparative C18 column. Suitable buffers can include, for example, ammonium acetate buffer, ammonium bicarbonate buffer, and 0.1 M Tris-HCl buffer.

BRIEF DESCRIPTION OF THE FIGURES

FIG. 2A is a graphical representation of a chromatographic purification of peptide B from Psp venom.

FIG. 2B is an additional graphical representation of a chromatographic purification of peptide B from Psp venom.

FIG. 2C is another graphical representation of a chromatographic purification of peptide B from Psp venom.

FIG. 3A is a graphical representation of a chromatographic purification of peptide C from *Haplopelma lividum* venom (Hv).

FIG. 3B is an additional graphical representation of a chromatographic purification of peptide C from *Haplopelma lividum* venom (Hv).

FIG. 3C is another graphical representation of a chromatographic purification of peptide C from *Haplopelma lividum* venom (Hv).

FIG. 4A is a graphical representation of a chromatographic purification of peptide D from Hv.

FIG. 4B is an additional graphical representation of a chromatographic purification of peptide D from Hv.

FIG. 4C is another graphical representation of a chromatographic purification of peptide D from Hv.

FIG. 5A is a graphical representation of a chromatographic purification of peptide E from Red Morph *Grammostola* (RMG) venom.

FIG. 5B is an additional graphical representation of a chromatographic purification of peptide E from Red Morph *Grammostola* (RMG) venom.

FIG. 5C is another graphical representation of a chromatographic purification of peptide E from Red Morph *Grammostola* (RMG) venom.

FIG. 5D is a further graphical representation of a chromatographic purification of peptide E from Red Morph *Grammostola* (RMG) venom.

FIG. 6A is a graphical representation of a chromatographic purification of peptide F from RMG venom.

FIG. 6B is an additional graphical representation of a chromatographic purification of peptide F from RMG venom.

FIG. 6C is another graphical representation of a chromatographic purification of peptide F from RMG venom.

FIG. 7A is a representation of $rNa_V1.3$ channels response to voltage ramp stimulation, before and during bath perfusion of 2 µM pure peptide A.

FIG. 7B is a representation of $hNa_V1.3$ channels response to voltage ramp stimulation, before and during (bath perfusion of 3.4 µM pure peptide A.

FIG. 7C is a representation of $rNa_V1.8$ channels response to voltage ramp stimulation, before and during bath perfusion of 2 µM pure peptide A.

FIG. 7D is a representation of $hK_V11.1$ (hERG) channels response to voltage steps stimulation, before and during bath perfusion of 5.25 µM pure peptide A, and during bath perfusion of an established hERG blocker.

FIG. 7E is a representation of a dose response curve, summarizing at least 3 experiments for each channel represented in FIGS. 7A-7D.

FIG. 7F is a representation of voltage responses to current stimulation in acutely dissociated rat DRG neurons.

FIG. 7G is a bar chart summarizing several experiments conducted in the conditions described in FIG. 7F.

FIG. 7H is a representation of a continuous trace of membrane voltage recorded in a mouse embryonic stem cells derived cardiomyocytes (mES-CM). Action potentials are spontaneously and regularly fired and their frequency and amplitude are plotted in the following charts.

FIG. 7I is a representation of a bar chart summarizing several experiments in which the effect of 3.75 µM peptide A and 3 µM TTX affected AP frequency.

FIG. 8G is a bar chart summarizing several experiments as in the conditions described in FIG. 8F.

FIG. 8H is a representation of a continuous trace of membrane voltage recorded in a mouse embryonic stem cells derived cardiomyocytes (mES-CM).

FIG. 8I is a bar chart summarizing several experiments in which the effect of 9 µM peptide B and 3 µM TTX affected AP frequency.

FIG. 9D is a representation of $hK_V11.1$ (hERG) channels response to voltage steps stimulation, before and during bath perfusion of 4 M pure peptide C, and during bath perfusion of an established hERG blocker.

FIG. 9E is a representation of a dose response curve, summarizing at least 3 experiments for each channel represented in FIGS. 9A-9D. Apparent $IC_{50}$s are given in Table 3.

FIG. 9F a representation superimposed traces of voltage responses to current stimulation in acutely dissociated rat DRG neurons.

FIG. 9G a bar chart summarizing several experiments as in the conditions described in FIG. 9F.

FIG. 9H is representation of a continuous trace of membrane voltage recorded in a mouse embryonic stem cells derived cardiomyocytes (mES-CM).

FIG. 9I represents a bar chart summarizing several experiments in which the effect of 5 µM peptide C and 3 µM TTX affected AP frequency.

FIG. 10A is a representation of $rNa_V1.3$ channels response to voltage ramp stimulation, before and during bath perfusion of 0.15 µM pure peptide D.

FIG. 10B is a representation of $hNa_V1.3$ channels response to voltage ramp stimulation, before and during bath perfusion of 0.5 µM pure peptide D.

FIG. 10C is a representation of $rNa_V1.8$ channels response to voltage ramp stimulation, before and during bath perfusion of 0.48 µM pure peptide D.

FIG. 10D is a representation of $hK_V11.1$ (hERG) channels response to voltage steps stimulation, before and during bath perfusion of 1 µM pure peptide D, and bath perfusion of an established hERG blocker.

FIG. 10E is a representation of a dose response curve, summarizing at least 3 experiments for each channel represented in FIGS. 10A-10D.

FIG. 10F is a representation of superimposed traces of voltage responses to current stimulation in acutely dissociated rat DRG neurons.

FIG. 10G is a bar chart summarizing several experiments as in the conditions described in FIG. 10F.

FIG. 10H is a representation of a continuous trace of membrane voltage recorded in a mouse embryonic stem cells derived cardiomyocytes (mES-CM).

FIG. 10I is a bar chart summarizing several experiments in which the effect of 0.75 µM peptide D and 3 µM TTX affected AP frequency.

FIG. 11A is a representation of $rNa_V1.3$ channels response to voltage ramp stimulation, before and during bath perfusion of 0.3 µM pure peptide E.

FIG. 11B is a representation of $hNa_V1.3$ channels response to voltage ramp stimulation, before and during bath perfusion of 0.93 µM pure peptide E.

FIG. 11C is a representation of $rNa_V1.8$ channels response to voltage ramp stimulation, before and during bath perfusion of 0.93 µM pure peptide E.

FIG. 11D is a representation of $hK_V11.1$ (hERG) channels response to voltage steps stimulation, before and during bath perfusion of 0.93 µM pure peptide E, and during bath perfusion of an established hERG blocker.

FIG. 11E is a representation of a dose response curve, summarizing at least 3 experiments for each channel described in FIGS. 11A-11D.

FIG. 11F is a representation of superimposed traces of voltage responses to current stimulation in acutely dissociated rat DRG neurons.

FIG. 11G is a bar chart summarizing several experiments as in the conditions described in FIG. 11F.

FIG. 11H is a representation of a continuous trace of membrane voltage recorded in a mouse embryonic stem cells derived cardiomyocytes (mES-CM).

FIG. 11I is a bar chart summarizing several experiments in which the effect of 0.83 µM peptide E and 3 µM TTX affected AP frequency.

FIG. 12D is a representation of $hK_V11.1$ (hERG) channels response to voltage steps stimulation, before and during bath perfusion of 0.92 µM pure peptide F, and during bath perfusion of an established hERG blocker.

FIG. 12E is a dose response curve, summarizing at least 3 experiments for each channel represented in FIGS. 12A-12D.

FIG. 12F is a representation of superimposed traces of voltage responses to current stimulation in acutely dissociated rat DRG neurons.

FIG. 12G is a bar chart summarizing several experiments as in the conditions described in FIG. 12F.

FIG. 12H is a representation of a continuous trace of membrane voltage recorded in a mouse embryonic stem cells derived cardiomyocytes (mES-CM).

FIG. 12I is a bar chart summarizing several experiments in which the effect of 1 µM peptide F and 3 µM TTX affected AP frequency.

DETAILED DESCRIPTION

I. Definitions

Figure 1A:
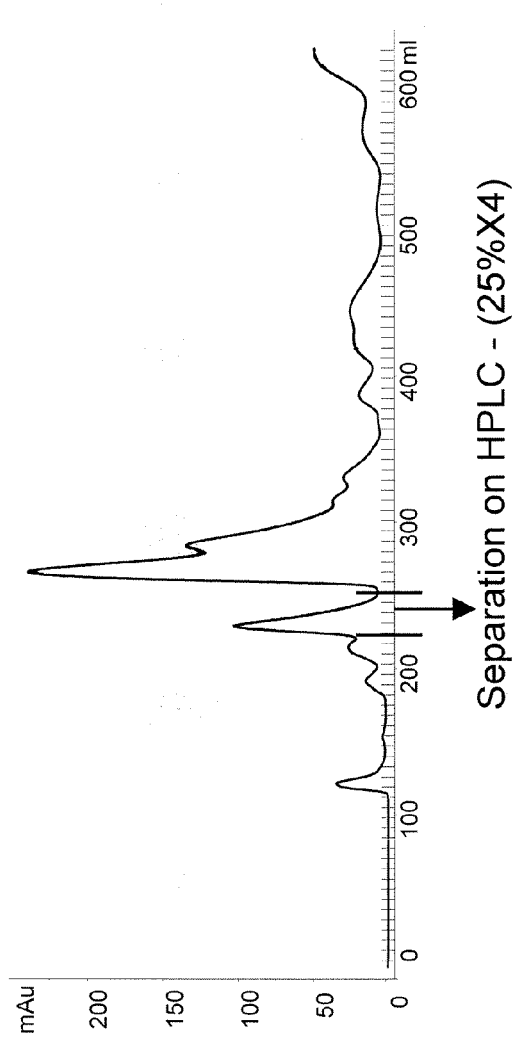
FIG. 1A is a graphical representation of a chromatographic purification of peptide A from *Pterinochilus* spp. *Usambara* venom (Psp).

The below definitions serve to provide a clear and consistent understanding of the specification and claims, including the scope to be given such terms.

As used herein, the terms "administering," "administration," and like terms refer to any method which, in sound medical practice, delivers the composition to a subject in such a manner as to provide a therapeutic effect. One aspect of the present subject matter provides for oral administration of a therapeutically effective amount of a composition of the present subject matter to a patient in need thereof.

The presently described spider venom peptides are useful for the treatment of pain or the induction of analgesia. As used herein the term "treating" also includes prophylaxis of pain in a patient or a subject having a tendency to develop such pain, and the amelioration or elimination or the developed pain once it has been established or alleviation of the characteristic symptoms of such pain.

As used herein the term "pain" refers to all types of pain. Particularly, the term refers to chronic pain, such as neuropathic pain, and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. In addition, neuropathic pain can arise from a number of separate etiologies. Neuropathic pain can occur as a consequence of ophthalmic surgery, dental repair (root canal), burn injury, reflex sympathetic dystrophy, post-herpetic neuralgia, diabetic neuropathy, arthritis and the like. The term also refers to pain due to reflex sympathetic dystrophy and nociceptive pain or nociception. In addition, the term "pain" refers to pain associated with an inflammatory condition, including but not limited to, pain associated with arthritis; autoimmune diseases including for example systemic lupus erythematosus (SLE) or lupus; chronic prostatis; chronic inflammation; hypersensitivitie; inflammatory bowel diseases; reperfusion injury; vasculitis; transplant rejection; pelvic inflammatory disease; glomerulonephritis; asthma, inflammatory myopathy; systemic sclerosis; dermatomyositis; polymyositis; inclusion body myositis; Chediak-Higashi syndrome; and chronic granulomatous disease.

Pharmaceutical compositions containing a compound of the present invention or its pharmaceutically acceptable salts or solvates as the active ingredient can be prepared according to conventional pharmaceutical compounding techniques. See, for example, Remington's Pharmaceutical Sciences, 18th Ed. (1990, Mack Publishing Co., Easton, Pa.).

As used herein, the term "excipient" or "adjuvant" refers to any component of a pharmaceutical composition that is not the drug substance.

As used herein, the phrases "drug product," "pharmaceutical dosage form," "final dosage form," and the like, refer to the combination of one or more drug substances and one or more excipients (i.e., pharmaceutical composition) that is administered to a patient in need of treatment, and can be in the form of a solution, an aqueous solution, an emulsion, a suspension, tablets, capsules, patches, suppositories, a cream, a gel, a lotion, and the like.

As used herein, the terms "subject" or "individual" or "animal" or "patient" or "mammal," refers to any subject, particularly a mammalian subject, for whom diagnosis, prognosis, or therapy is desired, for example, a human.

As used herein, the terms "treatment" or "treating" of a disease, disorder, or condition encompasses alleviation of at least one symptom thereof, a reduction in the severity thereof, or the delay, prevention, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, provide improvement to a patient or subject's quality of life, or delay, prevent, or inhibit the onset of a disease, disorder, or condition.

As used herein, the term "pharmaceutically acceptable" carrier refers to a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

The active agent is preferably administered in a therapeutically effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. The phrase "therapeutically effective amount" as used herein refers to an amount of the presently described active agent effective to yield a desired therapeutic response. For example, a "therapeutically effective amount," can be a sufficient amount of the active agent to treat or alleviate pain or to induce analgesia at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

As used herein the term "peptide" means a compound that is made up of two or more amino acids joined by covalent bonds which are formed by the elimination of a molecule of H2O from the amino group of one amino acid and the carboxyl group of the next amino acid.

The term "isolated" for the purposes of the present invention designates a biological material (nucleic acid or protein) that has been removed from its original environment (the environment in which it is naturally present). For example, a peptide present in the natural state in a plant or an animal is not isolated, however the same peptide separated from the adjacent amino acids in which it is naturally present, is considered "isolated."

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, preferably 2 or 3 and preferably 4 or 5 orders of magnitude.

As used herein, the term "substantially pure" describes a peptide or other material which has been separated from its native contaminants. Typically, a monomeric peptide is substantially pure when at least about 60 to 75% of a sample exhibits a single peptide backbone. Minor variants or chemical modifications typically share the same peptide sequence. Usually a substantially pure peptide will comprise over about 85 to 90% of a peptide sample, and particularly will be over 95% pure, over 97% pure, or will be over about 99% pure. Normally, purity is measured on a polyacrylamide gel, with homogeneity determined by staining Alternatively, for certain purposes high resolution will be necessary and HPLC or a similar means for purification will be used. For most purposes, a simple chromatography column or polyacrylamide gel will be used to determine purity.

The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

The term "homology" refers to the percent of identity between two polynucleotide or two peptide moieties. The correspondence between the sequence from one moiety to another can be determined by techniques known to the art. For example, homology can be determined by a direct comparison of the sequence information between two peptide molecules by aligning the sequence information and using readily available computer programs.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667). Such proteins (and their encoding genes) have sequence homology, as reflected by their high degree of sequence similarity. However, in common usage and in the instant application, the term "homologous," when modified with an adverb such as "highly," can refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two amino acid sequences are "substantially homologous" or "substantially similar" when at least about 50% (preferably at least about 75%, and most preferably at least about 90 or 95%) of the amino acids match over the defined length of the sequences. Sequences that are substantially homologous can be identified by comparing the sequences using known techniques.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "spider" refers to any tarantula of the family Theraphosidae, The family Theraphosidae is divided up into several subfamilies, containing over 100 genera and about 900 species between them. The subfamilies of Theraphosidae include:

Acanthopelminae, a subfamily of small, terrestrial new-world tarantulas. This subfamily has only one genus, *Acanthopelma*, and two species, *A. beccarri* and *A. Rufescens*;

Aviculariinae, is a subfamily of tropical, tree-dwelling new-world tarantulas. The genera include *Avicularia*, *Ephebopus*, *Iridopelma*, *Pachistopelma* and *Tapinauchenius*;

Eumenophorinae is a subfamily of old-world tarantulas. The genera include *Anoploscelus, Batesiella, Citharischius, Encyocrates, Eumenophorus, Hysterocrates, Loxomphalia, Loxoptygus, Mascaraneus, Monocentopus, Myostola*, and *Phoneyusa*. *Proshapalopus* is sometimes placed in this sub-family;

Harpactirinae is a subfamily of old-world tarantulas from Africa. The genera include *Augacephalus, Brachionopus, Ceratogyrus, Eucratoscelus, Harpactira, Idiothele, Pterinochilus*, and *Trichognathella*;

The subfamily Ischnocolinae contains spiders from around the world. The genera include *Catumiri, Chaetopelma, Cratorrhagus, Guyruita, Hemiercus, Heterothele, Holothele, Ischnocolus, Nesiergus, Oligoxystre, Plesiophrictus*, and *Sickius*;

The earth tigers of subfamily Ornithoctoninae form a group of old-world tarantulas. The genera include *Citharognathus, Cyriopagopus, Haplopelma, Lampropelma, Ornithoctonus*, and *Phormingochilus*;

Poecilotheriinae are tree spiders from India and Sri Lanka. This subfamily contains only a single genus *Poecilotheria*;

Selenocosmiinae is a subfamily which consists mainly of tarantulas from East Asia and Australia. The genera include *Baccallbrapo, Chilobrachys, Chilocosmia, Coremiocnemis, Haplocosmia, Lyrognathus, Orphnaecus, Phlogiellus, Phlogius, Psalmopoeus, Selenobrachys, Selenocosmia, Selenopelma, Selenotholus, Selenotypus, Tapinauchenius*, and *Yamia;*

Selenogyrinae is a subfamuly of tarantulas from India and Africa. The genera include *Annandaliella, Euphrictus*, and *Selenogyrus;*

Stromatopelminae are tree-dwelling tarantulas from western Africa. The genera include *Encyocratella, Heteroscodra*, and *Stromatopelma;*

Theraphosinae are new-world terrestrial tarantulas. The genera include *Acanthoscurria, Aenigmarachne, Ami, Aphonopelma, bonnetina, brachypelma, Chromatopelma, Citharacanthus, Clavopelma, Crassicrus, Cubanana, Cyclosternum, Cyriocosmus, Cyrtopholis, Euathlus, Eupalaestrus, Grammostola, Hapalopus, Hapalotremus, Hemirrhagus, Homoeomma, Kochiana, Lasiodora, Lasiodorides, Magulla, Maraca, Megaphobema, Melloleitaoina, Metriopelma, Neostenotarsus, Nesipelma, Nhandu, Ozopactus, Pamphobeteus, Paraphysa, Phormictopus, Plesiopelma, Proshapalopus, Pseudhapalopus, Reversopelma, Schismatothele, Schizopelma, Sericopelma, Sphaerobothria, Stichoplastoris, Theraphosa, Thrixopelma, Tmesiphantes, Vitalius*, and *Xenesthis;*

Thrigmopoeinae are Indian tarantulas. The genera include *Haploclastus* and *Thrigmopoeus;*

Suitable species include, but are not limited to, tarantulas of the subfamily Harpactirinae, genus *Pterinochilus*, including *Pterinochilus alluaudi, Pterinochilus chordates, Pterinochilus leetzi, Pterinochilus lugardi, Pterinochilus murinus* (i.e., *Pterinochilus* spp. *Usambara* (Psp)), *Pterinochilus simoni*, and *Pterinochilus vorax*. Still other suitable species include, but are not limited to tarantulas of the subfamily Ornithoctoninae, genus *Haplopelma*, including *Haplopelma albostriatum, Haplopelma doriae, Haplopelma hainanum, Haplopelma lividum, Haplopelma longipes, Haplopelma minax, Haplopelma robustum, Haplopelma salangense, Haplopelma schmidti*, and *Haplopelma vonwirthi*. Yet other suitable species include, but are not limited to tarantulas of the subfamily Theraphosinae, genus *grammostola*, including *Grammastola actaeon, Grammastola alticeps, Grammastola andreleetzi, Grammastola pulchripes, Grammastola burzaquensis, Grammastola chalcothrix, Grammastola doeringi, Grammastola fossor, Grammastola gossei, Grammastola grossa, Grammastola iheringi, Grammastola inermis, Grammastola mendozae, Grammastola mollicoma, Grammastola monticola, Grammastola porteri Grammastola pulchra, Grammastola rosea, Grammastola schulzei, Grammastola spatulata*, and *Grammastola vachoni*.

With regard to the classification of *Grammostola rosea*, it is to be understood that *Grammostola* rosea may be classified, for example as a brown morph or a red morph. The red morph of *Grammostola rosea* is also known as *Phrixotrichus auratus* and *Paraphysa scrofa*, and may be referred to as Red Morph *Grammostola* (RMG). The brown morph of *Grammostola rosea* is also known as *Grammostola poteri* is and *Grammostola spatulata*, and may be referred to as Brown Morph *Grammostola* (RMG). Also, at least two additional species or morphs of *Grammostola*, one is one from Concepion and one form Northern Chile.

Particularly suitable tarantula species include, but are not limited to, *Pterinochilus* spp. *Usambara* (Psp), *Haplopelma Lividum* (Hv) and Red Morph *Grammostola* (RMG).

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Other terms as used herein are meant to be defined by their well-known meanings in the art.

II. Methods of Isolating Spider Venom Peptides

The presently described isolated spider venom peptides can be isolated from crude spider venom. Particularly, a method for purifying crude venom to obtain the presently described isolated peptides can comprise or consist of centrifuging crude spider venom to obtain centrifuged venom; filtering the centrifuged venom to obtain filtered venom; loading the filtered venom on a gel filtration column; and eluting the column to obtain a fraction containing the isolated peptide, which can be further purified using cation exchange and/or HPLC chromatography.

The crude venom can be one or more of fresh venom, cryopreserved venom, or lyophilized crude venom. The crude venom, for example, lyophilized venom, can be dissolved in buffer, for example 100 mM AmAc at a pH of about 6.0 (buffer A), at for example, about 10,000 to about 16,000 rpm or about 13,000 rpm, for example, for from about 2 to about 15 minutes, or for about 7 minutes. The supernatant can optionally be further filtered, for example, through a membrane filter, for example a 0.22 µm filter. Thereafter, the supernatant or filtrate can be loaded onto a pre-washed gel filtration column, for example, Superdex-30. The column can be prewashed with about 2 column volumes (cv) of buffer A, then injecting the sample. Running parameters can include, for example, running the sample with 2 cv of buffer A at 0.8 ml/min, 7 ml/fraction. Fractions can then be pulled and optionally again filtered through a membrane filter, for example a 0.22 µm filter. Thereafter, the resultant sample can optionally be further purified using reverse phase HPLC and eluting by a step gradient including a solvent, for example, 5% ACN in 0.1% TFA (A), and a mobile phase, for example, 60% ACN in 0.1 TFA (B). The steps can be 0-30% B for 3 cv, 30-55% B for 10 cv, 0.5 ml/fraction and 55-100% B for 2 cv. The presently described peptides elute at the second step. The running parameters can be buffer 5%-60% CAN in 0.1% TFA. Three-segment gradient: 0%-30%-55%-100%, 0.5 ml/fraction, 1 ml/min. III.

Methods of Synthesizing Spider Venom Peptides

The presently described peptides can be prepared by chemical synthesis, or may be manufactured using recombinant DNA technology. To prepare the peptides of the present invention by chemical synthesis, the publicly known methods may be used, for example, the peptide of the present invention can be obtained by methods using azide, acid chloride, acid anhydride, compound acid anhydride, DCC, activated ester, Woodward's reagent K, carbonylimidazole, deoxidization, DCC/HONB, BOP reagent (see for example Bozanszky, M and M. A. Ondetti, *Peptide Synthesis*, Interscience Publishers, New York (1966); Schroeder and Luebke, *The Peptide*, Academic Press, New York (1965); F. M. Finn and K. Hofmann, *The Proteins* Vol. 2, H. Nenrath, R. L. Hill ed., Academic Press Inc., New York (1976); Nobuo Izumiya et al., Peptide Gosei no Kiso to Jikken (*Basics and experiments of peptide synthesis*), Maruzen Co. (1985); Haruaki Yajima and Shunpei Sakakibara et al., Seikagaku Jikken Koza (*Biochemical Experiment*) 1, Japanese Biochemical Society ed., Tokyo Kagaku Dojin Co. (1977); Toshiya Kimura, Zoku Seikagaku Jikken Koza (*Sequel to Biochemical Experiment*) 2, Japanese Biochemical Society ed., Tokyo Kagaku Dojin Co. (1987)). Furthermore, the presently described peptide can be prepared by chemical synthesis using an automated peptide synthesizer (e.g. PE Applied Bio Systems Co.). Methods, such as those described in Bulaj G., et al. (2006) Biochemistry 45, 7404, can also be used for synthesis of the presently described peptides and refolding procedures.

Further, following the completion of reaction, the presently described peptides can be purified and separated by publicly known purification methods. For example, the peptide of the present invention can be purified and separated by a combination of solvent extraction, distillation, column chromatography, liquid chromatography, recrystallization and the like. Where the presently described obtained by the above methods is in a free form, publicly known methods can be used to convert it into a salt form, and on the other hand, where the peptide is obtained in a salt form, publicly known methods can be used to convert it into a free form.

In addition, recombinant expression systems in *E. Coli* may be used to express the presently described peptides as a fusion proteins (TRX or GST), with a specific enzymatic cleavage site, for example, enterokinase or TEV. Next, the bacteria are broken and centrifuged and the resulting soup contains the fusion protein. The fusion protein can then be loaded on a specific affinity column, for example, a Ni2+ or glutathione column, to be eluted. After elution, the purified fusion protein is subjected to a specific enzymatic cleavage reaction. Then, the peptide is purified from the resultant mixture by HPLC or ion exchange chromatography.

IV. Other Biological Methods

Methods involving conventional and analytical chemistry, molecular biological and cell biological techniques are described herein. Such techniques are generally known in the art and are described in detail in methodology treatises such as *Classics in Total Synthesis, Targets, Strategies, Methods*, K. C. Nicolaou and E. J. Sorensen, VCH, New York, 1996;

*The Logic of Chemical Synthesis,* E. J. Coney and Xue-Min Cheng, Wiley & Sons, NY, 1989; and *NMR of Proteins and Nucleic Acids,* Wuthrich, K., Wiley & Sons, New York, 1986. Molecular biological and cell biological methods are described in treatises such as *Molecular Cloning: A Laboratory Manual,* 3rd ed., vol. 1-3, ed. Sambrook et al., Cold Spring Harbor Laboratory Press, Cold Spring Harbor, N.Y., 2001; and *Current Protocols in Molecular Biology,* ed. Ausubel et al., Greene Publishing and Wiley-Interscience, New York, 1992 (with periodic updates).

V. Pharmaceutical Compositions Including Spider Venom Peptides

Formulation

The presently described pharmaceutical compositions can be administered parenterally, topically, or rectally. They are of course given by forms suitable for each administration route. For example, they are administered by injection, inhalation, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Details of general formulation procedures and information on additional excipients may be found in Remington: *The Science and Practice of Pharmacy,* 20$^{th}$ Edition.

A composition containing an effective amount of the peptides described herein can be administered to a subject requiring treatment. The composition can be administered parenterally, intravenously, topically, orally, buccally, nasally, rectally, subcutaneously, intramuscularly, or intraperitoneally. In one implementation, the composition can be injected, e.g., into the cerebro-spinal fluid.

The composition of the treatment may formulated to be compatible with the route of administration. The composition can be formulated as a tablet, capsule, solution, powder, inhalant, lotion, tincture, troche, suppository, or transdermal patch. See, e.g., *Journal of Pharmaceutical Sciences,* (1963), 52:918 et seq.

A solution for parenteral, intradermal, or subcutaneous administration may comprise, for example: a sterile diluent such as water, saline, glycerin, fixed oils, polyethylene glycols, propylene glycol, or other synthetic solvents; an antibacterial agents such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Oral compositions include, for example: tablets; capsules; troches; suspensions; and solutions. The compositions may be fashioned with an inert diluent or an edible carrier. Capsules can be formulated by combining an appropriate diluent with a peptide or formulation thereof and filling the capsule with the mixture. Common diluents are starches such as powdered cellulose, or sugars such as sucrose, fructose, or mannitol. Tablets may be made by wet or dry granulation, by compression or by other known methods. In addition to the desired peptide/compound, compositions for tablets can include, for example: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition (see e.g., U.S. Pat. Nos. 5,417,986, 4,675, 381, and 4,450,150).

For administration by inhalation, the compounds may be delivered, for example, in the form of an aerosol spray from pressured container dispenser, which contains a suitable propellant, e.g., a gas, or by other known methods. For example, administration can also be transmucosal, e.g., with a nasal spray or suppository, or by transdermal means, e.g., as a salve, ointment, gel, or cream. Such modes of administration can use formulations comprising, for example, bile salts, and fusidic acid derivatives.

Modes of Administration

The peptides described herein can be administered, for example, by bolus injection, by continuous infusion, for example, so as to prolog contact with the epidural region or by other known methods. The peptide can be infused for any amount of time. Dosage and timing of administration can be modified according to the needs of the particular subject, e.g., within the framework of standard clinical protocols for treating pain. The peptide can also be delivered by intrathecal routes, and into the bloodstream. In addition, implantable or body-mountable pumps can be used to deliver the peptide described herein at a controlled rate. Alternatively, prolonged administration can be achieved by art-known depot or sustained release formulations.

Dosage

An appropriate dosage for treatment must be determined. An effective amount of an inhibitor is the amount or dose which is required to ameliorate a spinal muscular atrophy symptom in a subject. Determination of the amount or dose required to treat an individual subject is routine to one skilled in the art, e.g., a physician, pharmacist, or researcher.

The toxicity and therapeutic efficacy of the peptide and/or peptide formulations may also be determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios include, for example, rations greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, if means are available to deliver the compound to the affected tissue, while minimizing damage to unaffected tissue, e.g., endothelial tissue.

In formulating a dosage range for use in humans, the effective dose of a peptide preparation can be estimated from studies with laboratory animals, e.g., as described below. For example, therapeutically effective dosages in cell culture assays include, for example, about 0.1 nM, 1 nM, 10 nM, 100 nM, 1 µM, or 10 µM of the peptide, and ranges between. A dose can be formulated in an animal in order to achieve a circulating plasma concentration of inhibitor that falls in this range. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample using an antibody based specific ELISA assay or with high performance liquid chromatography or mass spectroscopy.

Alternatively, the dose can be estimated from tests in an animal model, as described below. Alleviation of symptoms is observed when rats receive a peptide or pharmaceutical composition at a dose of at least about from 1 µg/kg to 10 mg/kg, or more. For example, the dose may be 10 µg/kg, 20 µg/kg, 40 µg/kg, 80 µg/kg, 120 µg/kg, 180 µg/kg, 240 µg/kg, 300 µg/kg, or 360 µg/kg, 1 mg/kg, 3 mg/kg, 5 mg/kg, 7 mg/kg or 10 mg/Kg. The interrelationship of dosages for animals and humans (based on milligrams per meter squared of body surface) is described by, for example, Freireich et al., *Cancer Chemother. Rep.* 1966, 50, 219. Body surface area may be approximately determined from height and weight of the patient. See, e.g., Scientific Tables, Geigy Pharmaceuticals, Ardley, N.Y., 1970, 537. An effective dose for treating human patients is estimated to be approximately at least 3 µg/kg, 30 µg/kg, 120 µg/kg, 180 µg/kg, 240 µg/kg, 300 µg/kg, or 500 µg/kg. The peptide can be administered with a frequency or continuously in order to maintain a local concentration effective to reduce pain in the subject.

Depending on the method of administration, the appropriate dose can vary, e.g., from about 1 µg $kg^{-1}$ $day^{-1}$ to about 10 mg $kg^{-1}$ $day^{-1}$. The dose for a patient can be optimized while the patient is under care of a physician, pharmacist, or researcher. For example, a relatively low dose of the peptides described can be administered initially. The patient can be monitored for symptoms and sensation of pain as described below. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

EXAMPLES

Methods
Gel Filtration of Crude Venoms

*Pterinochilus* spp. *Usambara, Haplopelma Lividum* and Red Morph *Grammostola* spiders venoms were purchased from Spiderpharm, Ariz., USA. 100 mg of lyophilized crude venom from SpiderPharm (each batch was also measured for protein content by Nanodrop) were dissolved in 2.5 ml of buffer A (100 mM AmAc pH 6.0), centrifuged at 13000 rpm for 7 min, filtered through 0.22 µm cellulose acetate membrane filter and then loaded on Superdex-30 preparative gel filtration media (GE HealthCare) packed into XK column 26/70 (Code No: 56876900; GE HealthCare) using AKTA prime system (GE HealthCare, Amersham). The column was pre-washed with 2 column volumes (cv) of buffer A and sample was injected using sample loop. Running parameters: The sample was run at buffer A=100 mM AmAc pH 6.0 for 2 cv at 0.8 ml/min, 7 ml/fraction.

Other Chromatographic Procedures

Cation exchange and HPLC procedures are described in detail in FIGS. 1-6, legends.

Mass-Spectrum Analysis

MALDI-TOF M.S. (Applied Biosystems, Voyager Bio-spectrometry—DE, Sequenom) prepared by manufacturer protocol using sinapinic acid matrix.

Peptide Sequencing

Purified peptides were then submitted to sequencing which included:

Edman sequencing of native peptide, performed by Proteome Factory, Germany and/or Atheris, Switzerland.

MS-MS analysis of native peptide, performed by Proteome Factory, Germany and/or Atheris, Switzerland.

Enzymatic cleavage of native peptide and HPLC separation of fragments.

Edman sequencing of fragments, performed by Proteome Factory, Germany and/or Atheris, Switzerland.

Amino acid analysis of native peptide, performed at University of California, Davis, Calif., USA.

Monoisotopic LC-MS analysis performed by Proteome Factory, Germany and/or Atheris, Switzerland.

Cell Culture

Rat DRG neurons: Primary cultures of neurons from dorsal root ganglia (DRG) were collected from a 3 week old Charles River rat. The DRGs were prepared by enzymatic digestion in collagenas/dispas, dissociated in trypsin and triturated through a polished Pasteur pipette to a single-cell suspension. The cells were purified using percole gradient to enrich the cultures for neurons. They were then plated in a 24-well tissue culture plate on a Matrigel® coated coverslip and cultured in F-12 medium, 10% fetal calf serum (FCS) in the presence of 50 ng/ml NGF and 10 mM AraC at 37° C. The cultured DRGs can then be used for electrophysiology 24 h-4 days after preparation.

Mouse ES cells derived cardiomyocytes: Cor.At® ready-to-use cardiomyocytes derived from a genetically modified mouse embryonic stem cells that represent primary-like cells, and exhibit typical characteristics and features of primary cardiomyocytes, were used according to manufacturer's instruction. Briefly cell were thawing and separately attached ($1 \times 10^4$ cells) on 0.1% gelatin or 0.1% gelatin/fibronectin coated coverslip in Cor.At® medium containing Puromycin for 48 h and then the medium was changed to Cor.At® medium. The cells were used for ectrophysiology after 4 days within 1 week.

$rNa_v1.3$ channels were expressed in HEK-293 cells as described (Cummins, T. R., et al. 2001)

rNa$_v$1.8 in channels were expressed in ND7-23 cells by using conventional transient or stable transfections as described (Zhou, X., et al. 2003; John, V. H., et al. 2004; Jarvis, M. F., et al. 2007; Zimmermann, K., et al. 2007).

hNa$_v$1.3 in *Xenopus* oocytes. RNA was synthesized and injected into *Xenopus* oocytes (~10 ng per oocyte) and three days later inward currents were recorded using the Two-Electrode voltage clamp method (Dascal 1987).

hK$_v$11.1 (hERG) were expressed in HEK-293 cells as described (Zhou et al. 1998).

Electrophysiology Protocols:

The patch clamp method (Hamil et al. 1981) was used to trace and record, ionic currents or membrane voltage from a few cell types. These included heterologous expression systems over-expressing a recombinant channel as well as native or model cells. The solutions and voltage protocols used to trace activity are given in Table 1. In all the patch clamp recordings the Sampling rate was 10-50 kHz (interval 20-100 μs). The patch clamp set up included amplifier and digitizer (Axopatch 200B, DIGDATA 1322A—Axon instruments), microscope (Nikon ECLIPSE 100), and micromanipulator (MP-225—SUTTER INSTRUMENT Co.). Pipettes were pulled from Borosilicate glass tubes (SUTTER INSTRUMENT Co.). Cell were always perused with control extracellular solutions and changing to reagents containing solutions was performed using—ValveLink 16 (Automate Scientific Inc.) and a peristaltic pump (Iismatec) perfusion system. All chemicals were from Sigma apart from TTX, rBeKM-1 which were from Alomone (Israel).

Currents in *Xenopus* oocytes were recorded using bath ND 96 solution, Geneclamp and Digidata 1320 (Axon instruments) and a manual (gravitation based) perfusion system.

The fractions (#32-36) were pooled, filtered through 0.22 μm cellulose acetate filter and then ¼ of the sample was loaded onto a Phenomenex Jupiter reversed-phase HPLC column (5 u, C18, 300 A, 250×4.6 mm, 00G-4053-EO, S/No 397274-10), previously equilibrated with solvent A (5% ACN in 0.1% TFA), using HPLC system (AKTA purifier, GE HealthCare—Amersham). The proteins were eluted by a step gradient using solvent A (=5% ACN in 0.1% TFA) and 60% ACN in 0.1% TFA as a mobile phase (=buffer B), run at constant flow of 1 ml/min. The steps are: 0-30% B for 3 cv (1 cv~4.125 ml)), 30-55% B for 10 cv, 0.5 ml/fraction and 55-100% B for 2 cv. The relevant peptide elutes at the $2^{nd}$ step. The same procedure was performed to the rest of the sample (=4 sequential runs). Running parameters: Buffer: 5%-60% ACN in 0.1% TFA. 3-segment gradient: 0%-30%-55%-100%, 0.5 ml/fraction, 1 ml/min.

Chromatographic Purification of Peptide B from Psp Venom.

100 mg of lyophilized crude venom (110 mg by Nanodrop) were loaded on a gel filtration column in accordance with the procedure as described in the Methods.

Fractions #37-40 were pooled and #41-43 were pooled, and further each of the pooled fractions was filtered through a 0.22 μm filter and loaded onto a HiTrap SP Sepharose Fast Flow 5 ml Cation Exchanger column (GE-Amersham; Lot: 10005383-3) using AKTAprime system (GE HealthCare—Amersham). The column was previously activated with Buffer B (25 mM Ammonium acetate and 1M NaCl, pH=6.0) and washed with Buffer A (25 mM Ammonium Acetate pH=6.0 and 10 mM NaCl). Separation was performed by a step gradient at flow rate of 1 ml/min, 3 ml/fraction. The steps are: 0% A-50% B for 30 cv (A=25 mM Ammonium acetate and 1M NaCl, pH=6.0, B=25 mM Ammonium acetate and 1M NaCl, pH=6.0, 1 cv=5 ml), 50-50% B for 10 cv, 50-100% B for 4 cv. The relevant peptide elutes at $1^{st}$ step. Running parameters: 25 mM AmAc pH 6.0 and 10 mM to 1M NaCl gradient for 30 cv 0-50% B, 1 ml/min, 3 ml/fraction.

Relevant peaks from SP-Sepharose column were filtered through a 0.22 μm filter and then subjected to further purification by HPLC in 2 sequential runs each (on the AKTApurifier, GE HealthCare—Amersham), using a Phenomenex Jupiter reversed-phase HPLC column (5 u, C18, 300 A, 250× 4.6 mm, 00G-4053-EO, S/No 397274-10), previously equili-

TABLE 1

| Channel and/or Cell type | Intracellular solution (in mM) All included 10 HEPES (pH = 7.2 titrated with KOH) | Extracellular solution (in mM) All included 1 MgCl$_2$, 2 CaCl$_2$, 5 glucose, 10 HEPES (pH = 7.4 titrated with NaOH) | Voltage protocol |
|---|---|---|---|
| rNa$_v$1.3-HEK | 120 CsF, 10 NaCl, | 115 NaCl, 20 TEA-OH | Voltage-CLAMP: Holding level –100 mV, ramp from –100 to +60 mV (50 msec), minimum time between sweeps 10 seconds |
| rNa$_v$1.8-ND7 | 10 TEA-OH, 1 MgCl$_2$, 1 CaCl$_2$, 11 EGTA, | 115 NaCl, 20 TEA-OH, 600 nM TTX | |
| hK$_v$11.1 (hERG)-293T | 135 KCl 2 CaCl$_2$, 5 EGTA, 4 Mg-ATP | 135 NaCl, 5.4 KCl 600 nM TTX | Voltage-CLAMP: Holding level –100 mV, Step to 80 mV (250 msec), Step to –40 mV (250 msec) and Step to –90 mV (100 msec), minimum time between sweeps 10 seconds. |
| Spontaneous AP in Mouse ES derived Cardiomyocytes | 130 K-gluconate, 4 NaCl, 10 Na-Phosphocreatine, 10 Na-gluconate, | 135 NaCl, 5.4 KCl | Current-CLAMP: No stimulus |
| Evoked AP in Rat DRG | 4 Mg-ATP, 0.3 GTP, | | Current-CLAMP: Step 0.8-2.6 nA (2 msec), minimum time between sweeps 10 seconds. |

Example 1

Peptide Purification from Crude Venom and Chemical Characterization

Peptides A, B, C, D, E and F were isolated from *Pterinochilus* spp. *Usambara* (Psp), *Haplopelma Lividum* (Hv) and Red Morph *Grammostola* (RMG) spiders venoms, using a few different chromatographic steps (see FIGS. 1-6):

Chromatographic Purification of Peptide A from Psp Venom.

100 mg of lyophilized crude venom (110 mg by Nanodrop) were loaded on a gel filtration column in accordance with the procedure described in the Methods section.

brated with solvent A (5% ACN in 0.1% TFA). The peptide was eluted by a step gradient using solvent A (=5% ACN in 0.1% TFA) and 60% ACN in 0.1% TFA as a mobile phase (=buffer B), run at constant flow of 1 ml/min. The steps are: 0-30% B for 3 cv (1 cv~4.125 ml)), 30-55% B for 10 cv, 0.5 ml/fraction and 55-100% B for 2 cv. The relevant peptide elutes at $2^{nd}$ step. Running parameters: Buffer: 5%-60% ACN in 0.1% TFA. 3-segment gradient: 0%-30%-55%-100%, 0.5 ml/fraction, 1 ml/min.

Chromatographic Purification of Peptide C from Hv Venom.

100 mg of lyophilized crude venom (55 mg by Nanodrop) were loaded on a gel filtration column in accordance with the procedure as described in the Methods (see above).

Lyophilized peaks after gel filtration were dissolved in double distilled water (DDW), filtered through a 0.22 µm filter and loaded onto a HiTrap SP Sepharose Fast Flow 5 ml Cation Exchanger column (GE-Amersham; Lot: 10005383-3) using AKT Aprime system (GE HealthCare—Amersham). The column was previously activated with Buffer B (=25 mM Ammonium acetate and 1M NaCl, pH=6.0) and washed with Buffer A (=25 mM Ammonium Acetate pH=6.0 and 10 mM NaCl). Separation was performed by a step gradient at flow rate of 1 ml/min, 3 ml/fraction. The steps are: 0% A-50% B for 30 cv (A=25 mM Ammonium acetate and 1 M NaCl, pH=6.0, B=25 mM Ammonium acetate and 1 M NaCl, pH=6.0, 1 cv=5 ml), 50-50% B for 10 cv, 50-100% B for 4 cv. Running parameters: 25 mM AmAc pH 6.0 and 10 mM to 1M NaCl gradient for 30 cv 0-50% B, 1 ml/min, 3 ml/fraction.

The active peak from the SP-Sepharose column was subjected to further purification by HPLC (on the AKTApurifier, GE HealthCare—Amersham), using a Phenomenex Jupiter reversed-phase HPLC column (5 u, C18, 300 A, 250×4.6 mm, 00G-4053-EO, S/No 397274-10), previously equilibrated with solvent A (5% ACN in 0.1% TFA). The peptide was eluted by a step gradient using solvent A (=5% ACN in 0.1% TFA) and 60% ACN in 0.1% TFA as a mobile phase (=B), run at constant flow of 1 ml/min. The steps are: 0-28% B for 2 cv (1 cv~20 ml)), 28-47% B for 8 cv, 0.5 ml/fraction and 47-100% B for 2 cv. The relevant peptide elutes at $2^{nd}$ step. Running parameters: Buffer: 5%-60% ACN in 0.1% TFA, 3-segment gradient: 0%-28%-47%-100%, 0.5 ml/fraction, 1 ml/min Chromatographic Purification of Peptide D from Hv Venom.

100 mg of lyophilized crude venom (55 mg by Nanodrop) were loaded onto a gel filtration column and processed according to the procedure as described in the Methods.

Lyophilized peaks after gel filtration were dissolved in DDW, filtrated through a 0.22 µm filter and loaded onto a HiTrap SP Sepharose Fast Flow 5 ml Cation Exchanger column (GE-Amersham; Lot: 10005383-3) using AKTAprime system (GE HealthCare—Amersham). The column was previously activated with Buffer B (=25 mM Ammonium acetate and 1M NaCl, pH=6.0) and washed with Buffer A (=25 mM Ammonium Acetate pH=6.0 and 10 mM NaCl). Separation was performed by a step gradient at flow rate of 1 ml/min, 3 ml/fraction. The steps are: 0% A-50% B for 30 cv (A=25 mM Ammonium acetate and 1 M NaCl, pH=6.0, B=25 mM Ammonium acetate and 1 M NaCl, pH=6.0, 1 cv=5 ml), 50-50% B for 10 cv, 50-100% B for 4 cv. Running parameters: 25 mM AmAc pH 6.0 and 10 mM to 1M NaCl gradient for 30 cv 0-50% B, 1 ml/min, 3 ml/fraction.

The active peak from the SP-Sepharose column was subjected to further purification by HPLC (on the AKTApurifier, GE HealthCare—Amersham), using a Phenomenex Jupiter reversed-phase HPLC column (5 u, C18, 300 A, 250×4.6 mm, 00G-4053-EO, S/No 397274-10), previously equilibrated with solvent A (5% ACN in 0.1% TFA). The peptide was eluted by a step gradient using solvent A (=5% ACN in 0.1% TFA) and 60% ACN in 0.1% TFA as a mobile phase (=B), run at constant flow of 1 ml/min. The steps are: 0-28% B for 2 cv (1 cv~20 ml)), 28-47% B for 8 cv, 0.5 ml/fraction and 47-100% B for 2 cv. The relevant peptide elutes at $2^{nd}$ step. Running parameters: Buffer: 5%-60% ACN in 0.1% TFA, 3-segment gradient: 0%-28%-47%-100%, 0.5 ml/fraction, 1 ml/min Chromatographic Purification of Peptide E from RMG Venom.

100 mg of lyophilized crude venom (150 mg by Nanodrop) were loaded onto a gel filtration column and processed according to the procedure as described in the Methods.

Fractions #37-38 were loaded onto a Phenomenex Jupiter reversed-phase HPLC column (C18 10 u 300 A, 250×10 mm, 00G-4055-NO, S/No. 378159-1), previously equilibrated with solvent A (5% ACN in 0.1% TFA), using HPLC system (AKTApurifier, GE HealthCare—Amersham). The proteins were eluted by a step gradient using solvent A (=5% ACN in 0.1% TFA) and 60% ACN in 0.1% TFA as a mobile phase (=buffer B), run at constant flow of 2.5 ml/min. The steps are: 0-35% B for 3 cv (1 cv~20 ml)), 35-38% B for 6 cv and 38-100% B for 2 cv. The relevant peptide elutes at $2^{nd}$ step. Finally, related peaks from fractions #37+38 were pooled and lyophilized for further separation. Running parameters: Buffer: 5%-60% ACN in 0.1% TFA, 3-segment gradient: 0%-35%-38%-100%, 2 ml/fraction, 2.5 ml/min.

The lyophilized peak was dissolved in DDW, filtrated through a 0.22 µm filter and loaded onto a HiTrap SP Sepharose Fast Flow 1 ml Cation Exchanger column (GE-Healthcare, Lot 10012762) using AKTApurifuer system (GE HealthCare—Amersham). The column was previously activated with Buffer B (25 mM Ammonium acetate and 1M NaCl, pH=6.0) and washed with Buffer A (25 mM Ammonium Acetate pH=6.0 and 10 mM NaCl). Separation was performed by a step gradient at flow rate of 1 ml/min, 0.5 ml/fraction. The steps are: 0% A-50% B for 30 cv (A=25 mM Ammonium acetate and 1M NaCl, pH=6.0, B=25 mM Ammonium acetate and 1 M NaCl, pH=6.0, 1 cv=1 ml), 50-50% B for 10 cv, 50-100% B for 4 cv. The relevant peptide elutes at $1^{st}$ step. Running parameters: 25 mM AmAc pH 6.0 and 10 mM to 1 M NaCl gradient for 30 cv 0-50% B, 1 ml/min, 3 ml/fraction.

The active peak from the SP-Sepharose column was subjected to further purification by HPLC (on the AKTApurifier, GE HealthCare—Amersham), using a Phenomenex Jupiter reversed-phase HPLC column (C18 10 u 300 A, 250×10 mm, 00G-4055-NO, S/No. 378159-1) previously equilibrated with solvent A (5% ACN in 0.1% TFA). The peptide was eluted by a step gradient using solvent A (=5% ACN in 0.1% TFA) and 60% ACN in 0.1% TFA as a mobile phase, run at constant flow of 1 ml/min. The steps are: 0-30% B for 3 cv (1 cv~20 ml)), 30-55% B for 6 cv, 0.5 ml/fraction and 55-100% B for 2 cv. The relevant peptide elutes at $2^{nd}$ step. Running parameters: Buffer: 5%-60% ACN in 0.1% TFA. 3-segment gradient: 0%-30%-55%-100%, 0.5 ml/fraction, 1 ml/min.

Chromatographic Purification of Peptide F from RMG Venom.

100 mg of lyophilized crude venom (150 mg by Nanodrop) were loaded onto a gel filtration column and processed according to the procedure as described in the Methods.

The lyophilized peak was dissolved in DDW, filtrated through a 0.22 µm filter and loaded onto a HiTrap SP Sepharose Fast Flow 5 ml Cation Exchanger column (GE—Amersham; Lot: 10005383-3) using AKTApurifuer system (GE HealthCare—Amersham). The column was previously activated with Buffer B (25 mM Ammonium acetate and 1M NaCl, pH=6.0) and washed with Buffer A (25 mM Ammonium Acetate pH=6.0 and 10 mM NaCl). Separation was performed by a step gradient at flow rate of 1 ml/min, 0.5 ml/fraction. The steps are: 0% A-50% B for 30 cv (A=25 mM Ammonium acetate and 1 M NaCl, pH=6.0, B=25 mM Ammonium acetate and 1 M NaCl, pH=6.0, 1 cv=1 ml), 50-50% B for 10 cv, 50-100% B for 4 cv. The relevant peptide elutes at $1^{st}$ step. Running parameters: 25 mM AmAc pH 6.0 and 10 mM to 1M NaCl gradient for 30 cv 0-50% B, 1 ml/min, 3 ml/fraction.

The active peak from the SP-Sepharose column was subjected to further purification by HPLC (on the AKTApurifier, GE HealthCare—Amersham), using a Phenomenex Jupiter reversed-phase HPLC column (C18 10 u 300 A, 250×10 mm, 00G-4055-NO, S/No. 378159-1) previously equilibrated with solvent A (5% ACN in 0.1% TFA). The peptide was eluted by a step gradient using solvent A (=5% ACN in 0.1% TFA) and 60% ACN in 0.1% TFA as a mobile phase (=buffer B), run at constant flow of 2.5 ml/min. The steps are: 0-35% B for 3 cv (1 cv~20 ml)), 35-55% B for 15 cv, 1.5 ml/fraction and 55-100% B for 2 cv. The relevant peptide elutes at $2^{nd}$ step. Running parameters: Buffer: 5%-60% ACN in 0.1% TFA. 3-segment gradient: 0%-35%-55%-100%, 1.5 ml/fraction, 2.5 ml/min.

The resulting peptide masses and sequences are summarized in Table 2.

TABLE 2

| Peptide | M.W. | AA | SEQ ID NO: | Sequence |
|---|---|---|---|---|
| A | 3966.7 | 34 | 1 | DDCLGMFSSCDPDNDKCCEGRKCNR KDKWCKYVL* |
| B | 3636.6 | 29 | 2 | YCQEFLWTCDEERKCCGDMVCRLWC KKRL* |
| C | 3917.8 | 35 | 3 | ACLGFGEKCNPSNDKCCKSSSLVCS QKHKWCKYGW |
| D | 3705.6 | 33 | 4 | ACKGLFVTCTPGKDECCPNHVCSSK HKWCKYKT* |
| E | 4070.8 | 34 | 5 | DCLGFMRKCIPDNDKCCRPNLVCSR THKWCKYVF* |
| F& | 4168.8 | 34 | 6 | DCLGWFKGCDPDNDKCCEGYKCNRR DKWCKYKLW |

*-C-term amidation.
F& = VSTx-3 (Ruta and Mackinnon, 2004, Acc #P0C2P5).

All six peptides contain six Cysteines in their sequences which are noted according to their order of appearance from the N-terminal side. The existence of three disulphide bridges between Cysteine pairs was confirmed by MS analysis of native and reduced samples for all peptides. The order of pair Cysteine bonding is deduced from similarity to many other Tarantula toxins and is probably in the following order: C1-C4, C2-C5 and C3-C6 (for review see, Escoubas, F. and Rash, L., 2004). In addition, peptides A, B, D and E are amidated at their C-terminal.

Example 2

Refolding of the Synthetic Peptides

Peptides A, B, C, D, E and F were produced synthetically by solid phase synthetic procedures by chemical synthesis using BOC (t-Butyloxycarbonyl) or Fmoc (9-Fluorenylmethyloxycarbonyl) solid-phase peptide synthesis according to Schnolzer, M., et al., (1992) *In situ neutralization in BOC-chemistry solid phase peptide synthesis*, Int. J. Pept. Protein Res. 40, 180-193, and Atherton, E., et al., (1989) *Solid Phase Peptide Synthesis* (IRL, Oxford, U.K.), and were supplied as lyophilized powder at a purity of 70-95%. Each peptide was then subjected to a different refolding procedure as described below to achieve correct folding and biological activity identical to the venom purified native peptide.

Refolding of Peptide A

The crude synthetic peptide was dissolved at a protein concentration of 5 mM in 0.1M Tris buffer pH 8.5 and then reduced with 20 mM DTT at room temperature (RT) for 1 hr. The reduced peptide was added to the folding solution containing 0.1M Tris buffer pH 8.5 and a mixture of 0.5 mM Cysteine and 0.5 mM Cystine at a final concentration of 25 μM. Refolding and formation of the correct disulphide bridging pattern was achieved using a Cysteine/Cystine buffer system for 8 days at 4° C.

The refolded synthetic toxin was purified by reversed-phase HPLC on a semi-preparative C18 column (Phenomenex Jupiter, 250×10 mm, 10 micron, 300 A) using a 31.5 min gradient from 26% to 53% of 60% CH3CN in 0.1% TFA (5 mL/min). Refolding of peptide A was confirmed by MALDI-TOF mass spectrometry and bioassay.

Figure 13:
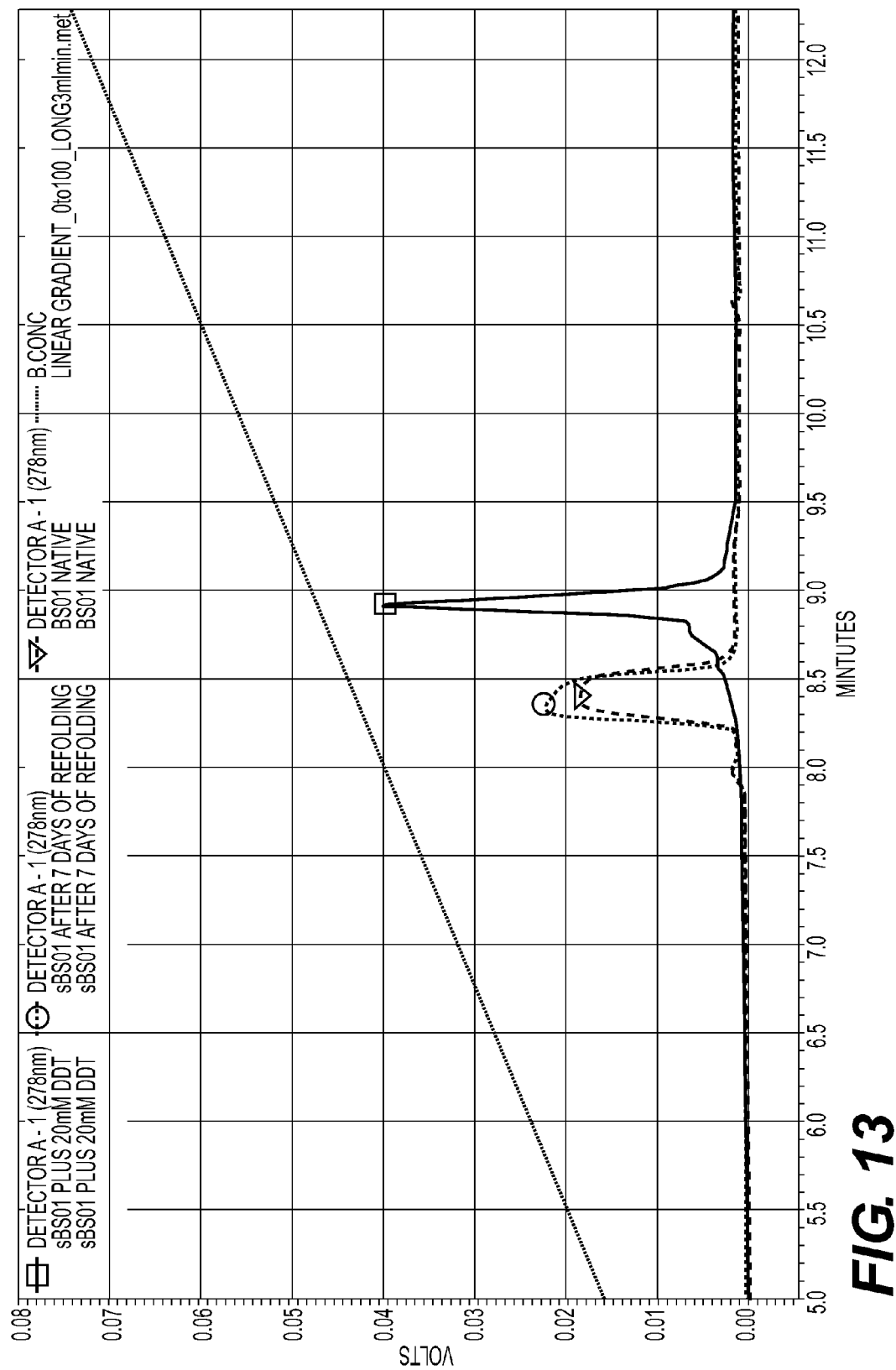
FIG. 13 is a representation of analytical reverse-phase HPLC chromatograms of native peptide A (triangle), reduced synthetic peptide A with 20 mM Dithiothreitol (DTT) for 1 hr. (square) and folded synthetic peptide A (circle).

For chromatographic comparison of synthetic peptide A with the natural peptide samples of native, folded and reduced peptides were purified by reversed-phase HPLC (Shimadzu system) using an analytical C18 column (Phenomenex Kinetex, 50×4.6 mm, 2.6 micron, 100 A). Reversed-phase-HPLC analysis was achieved with a 10 min linear gradient from 5%-60% $CH_3CN$ (2.5 ml/min) (see FIG. 13).

Refolding of Peptide B

The crude synthetic peptide was dissolved at a protein concentration of 1.1 mM in 6M GnHCl (guanidine hydrochloride) and 0.1M Tris buffer pH 9.5 and then reduced with 20 mM DTT at RT for 1.5 hr. The reduced peptide was added to the folding solution containing 0.1M Tris buffer pH 9.5 and a mixture of 0.15 mM Cysteine and 1.5 mM Cystine at a final concentration of 27.5 μM. Refolding and formation of the correct disulphide bridging pattern was achieved using a Cysteine/Cystine buffer system for 1 day at 4° C.

The refolded synthetic toxin was purified by reversed-phase HPLC on a semi-preparative C18 column (Phenomenex Jupiter, 250×10 mm, 10 micron, 300 A) using a 26.18 min gradient from 30% to 55% of 60% $CH_3CN$ in 0.1% Trifluoroacetic acid (TFA) (6 mL/min). Refolding of peptide B was confirmed by MALDI-TOF mass spectrometry and bioassay.

Figure 14:
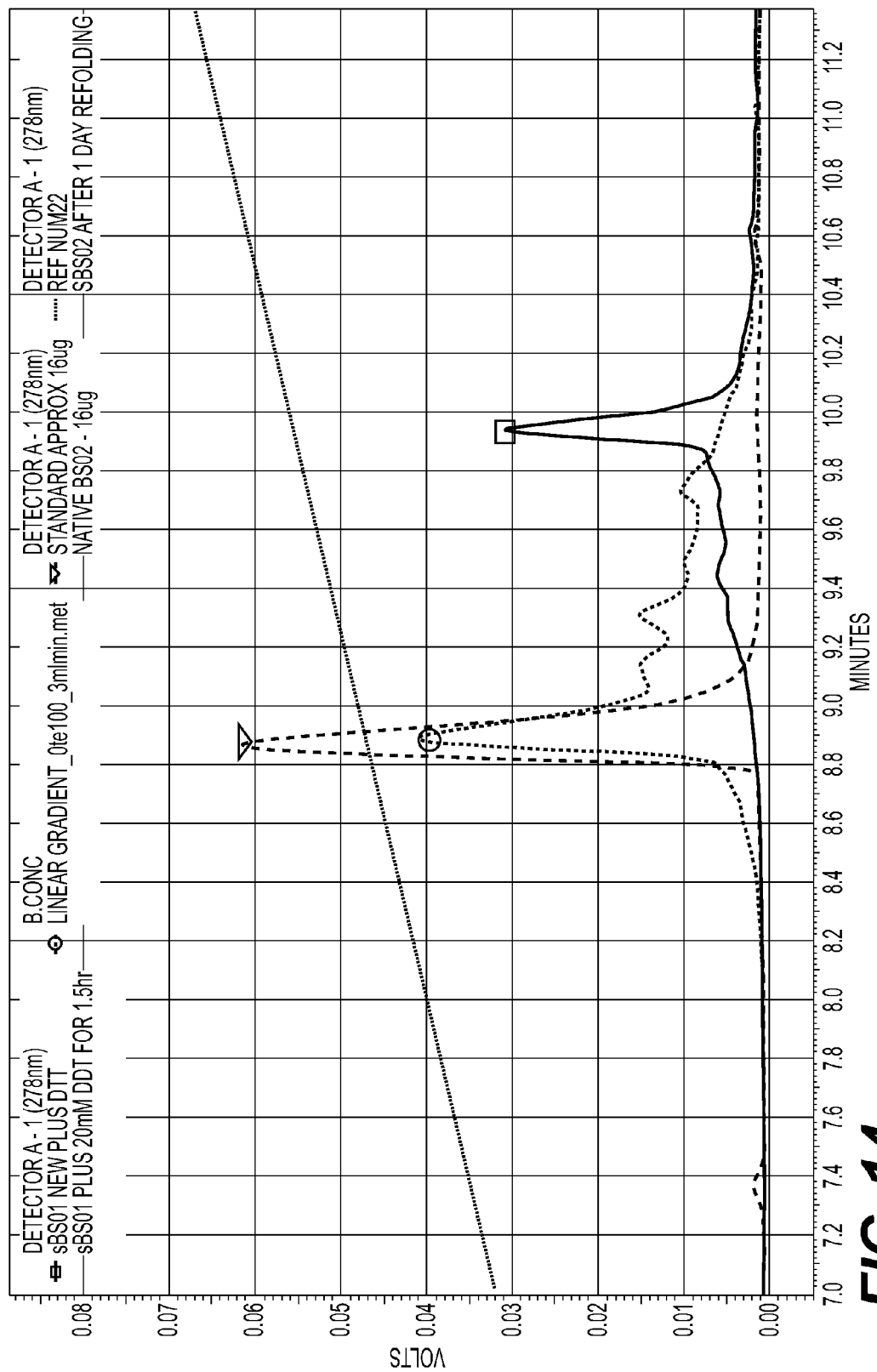
FIG. 14 is a representation of analytical reverse-phase HPLC chromatograms of native peptide B (triangle), reduced synthetic peptide B with 20 mM DTT for 1.5 hr. (square) and folded synthetic peptide B (circle).

For chromatographic comparison of synthetic peptide B with the natural peptide samples of native, folded and reduced peptides were purified by reversed-phase HPLC (Shimadzu system) using an analytical C18 column (Phenomenex Kinetex, 50×4.6 mm, 2.6 micron, 100 A). Reversed-phase HPLC analysis was achieved with a 10 min linear gradient from 5%-60% CH3CN (2.5 ml/min) (see FIG. 14).

Refolding of Peptide C

The crude synthetic peptide was dissolved at a protein concentration of 10.6 mM in 6M GnHCl and 0.1M Tris buffer pH 7.5 and then reduced with 20 mM DTT at RT for 1 hr. The reduced peptide was added to the folding solution containing 0.1M Tris buffer pH 7.5 and a mixture of 0.15 mM Cysteine and 1.5 mM Cystine at a final concentration of 25.5 μM. Refolding and formation of the correct disulphide bridging pattern was achieved using a Cysteine/Cystine buffer system for 5 days at 4° C.

The refolded synthetic toxin was purified by reversed-phase HPLC on a semi-preparative C18 column (Phenomenex Jupiter, 250×10 mm, 10 micron, 300 A) using a 26.18 min gradient from 22% to 45% of 60% $CH_3CN$ in 0.1% TFA (6 mL/min). Refolding of peptide C was confirmed by MALDI-TOF mass spectrometry and bioassay.

Figure 15:
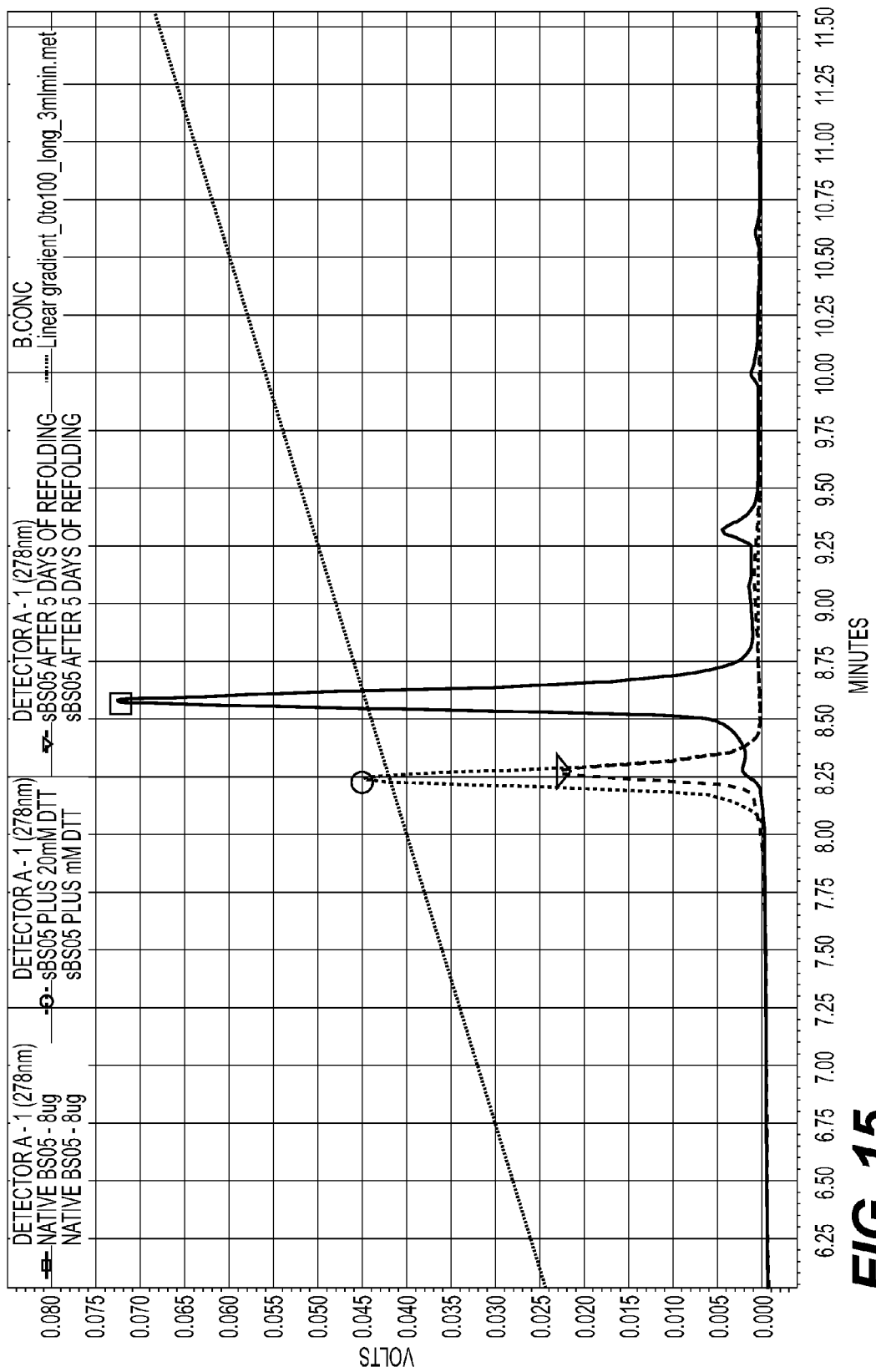
FIG. 15 is a representation of Analytical reverse-phase HPLC chromatograms of native peptide C (triangle) reduced synthetic peptide C with 20 mM DTT for 1 hr. (square) and folded synthetic peptide C (circle).

For chromatographic comparison of synthetic peptide C with the natural peptide samples of native, folded and reduced peptides were purified by reversed-phase HPLC (Shimadzu system) using an analytical C18 column (Phenomenex Kinetex, 50×4.6 mm, 2.6 micron, 100 A). RP-HPLC analysis was achieved with a 10 min linear gradient from 5%-60% CH3CN (2.5 ml/min) (see FIG. 15).

Refolding of Peptide D

The crude synthetic peptide was dissolved at a protein concentration of 24 mM in 0.1M Tris buffer pH 7.5 and then reduced with 20 mM DTT at RT for 1 hr. The reduced peptide was added to the folding solution containing 0.1M Tris buffer pH 7.5 and a mixture of 1.5 mM Cysteine and 0.15 mM Cystine at a final concentration of 13.5 µM. Refolding and formation of the correct disulphide bridging pattern was achieved using a Cysteine/Cystine buffer system for 4 days at 4° C.

The refolded synthetic toxin was purified by reversed-phase HPLC on a semi-preparative C18 column (Phenomenex Jupiter, 250×10 mm, 10 micron, 300 A) using a 35 min gradient from 25% to 55% of 60% CH3CN in 0.1% TFA (4.5 mL/min). Refolding of peptide D was confirmed by MALDI-TOF mass spectrometry and bioassay.

Figure 16:
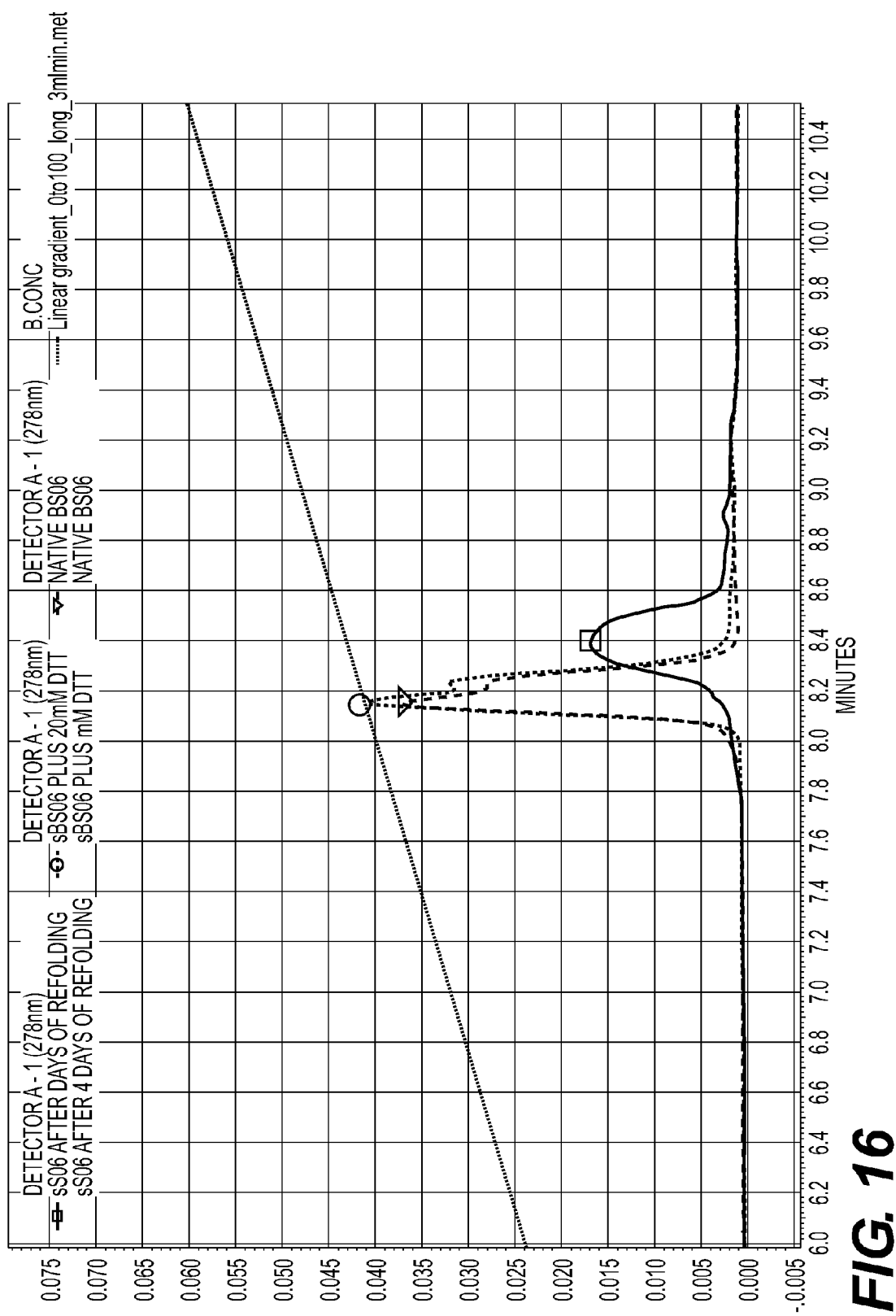
FIG. 16 is a representation of analytical reversed-phase HPLC chromatograms of native peptide D (triangle), reduced synthetic peptide D with 20 mM DTT for 1 hr. (square) and folded synthetic peptide D (circle).

For chromatographic comparison of synthetic peptide D with the natural peptide samples of native, folded and reduced peptides were purified by reversed-phase HPLC (Shimadzu system) using an analytical C18 column (Phenomenex Kinetex, 50×4.6 mm, 2.6 micron, 100 A). RP-HPLC analysis was achieved with a 10 min linear gradient from 5%-60% $CH_3CN$ (2.5 ml/min) (see FIG. 16).

Refolding of Peptide E

The crude synthetic peptide was dissolved at a protein concentration of 6 mM in 0.1M Tris buffer pH 7.5 and then reduced with 20 mM DTT at RT for 1 hr. The reduced peptide was added to the folding solution containing 0.1M Tris buffer pH 7.5 and a mixture of 0.15 mM Cysteine and 1.5 mM Cystine at a final concentration of 24.5 µM. Refolding and formation of the correct disulphide bridging pattern was achieved using a Cysteine/Cystine buffer system for 2 days at 4° C.

The refolded synthetic toxin was purified by reversed-phase HPLC on a semi-preparative C18 column (Phenomenex Jupiter, 250×10 mm, 10 micron, 300 A) using a 35 min gradient from 23% to 45% of 60% CH3CN in 0.1% TFA (6 mL/min). Refolding of peptide E was confirmed by MALDI-TOF mass spectrometry and bioassay.

Figure 17:
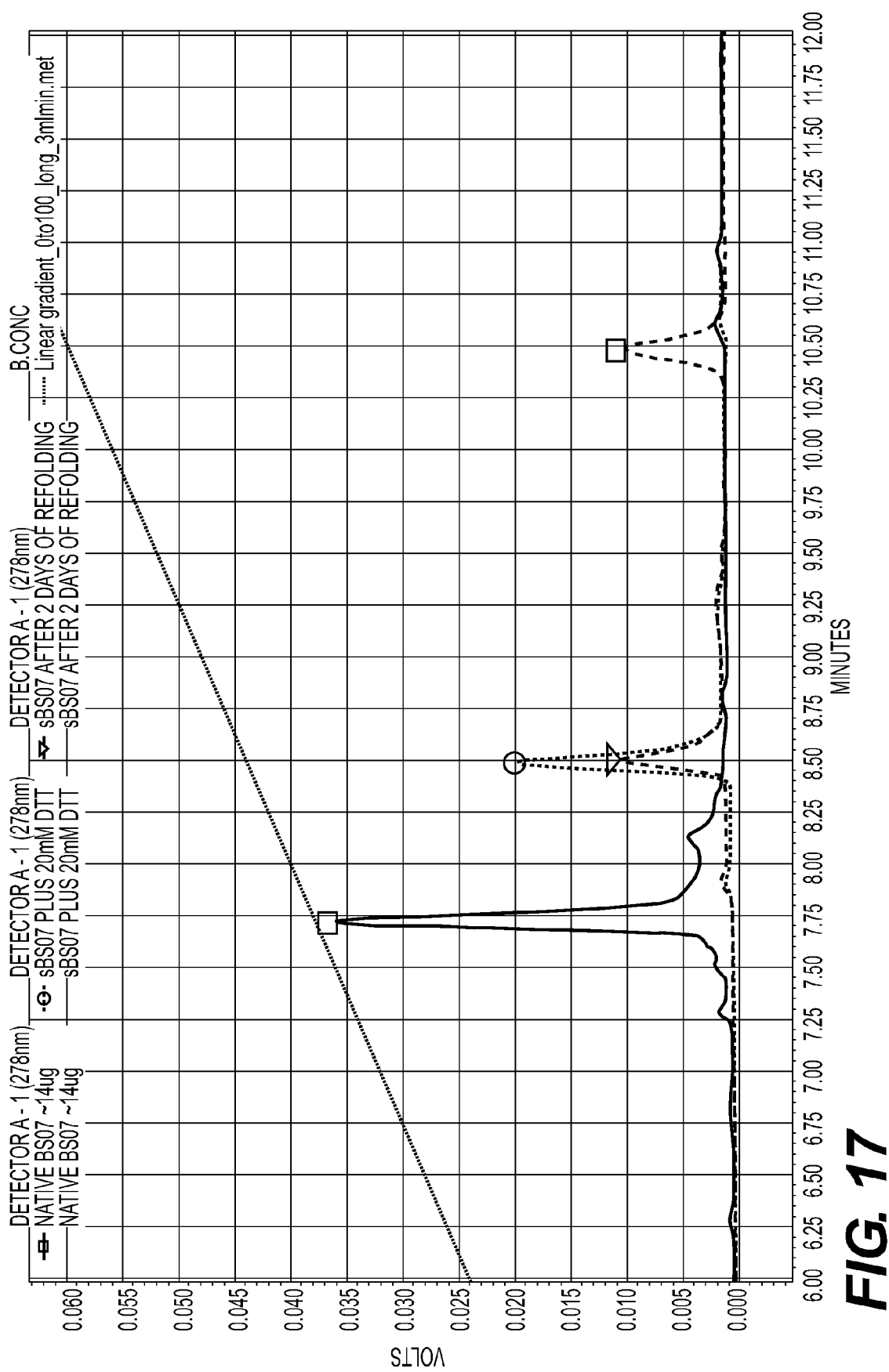
FIG. 17 is a representation of analytical reversed-phase HPLC chromatograms of native peptide E (triangle), reduced synthetic peptide E with 20 mM DTT for 1 hr. (square) and folded synthetic peptide E (circle).

For chromatographic comparison of synthetic BS-07 with the natural peptide samples of native, folded and reduced peptides were purified by reversed-phase HPLC (Shimadzu system) using an analytical C18 column (Phenomenex Kinetex, 50×4.6 mm, 2.6 micron, 100 A). Reversed-phase HPLC analysis was achieved with a 10 min linear gradient from 5%-60% $CH_3CN$ (2.5 ml/min) (see FIG. 17). Refolding of peptide F:

Crude peptide was weighed, dissolved in water and measured at 280 nm.

The reducing of the peptide was carried out by DTT which was added to a final concentration of 20 mM and incubated at RT for 1 hr.

The reduced peptide F was subjected to oxidative folding reaction in a 2M $NH_4OAc$ buffer (pH=7.0) containing 1 mM Glutathione (GSH), 0.1 mM oxidized glutathione (GSSG) and 1 mM EDTA. The reduced peptide was added to the solution drop wise in 6 portions to a final concentration of 10 µM. The solution was stirred at 24° C. for 120 hr.

The refolded material was purified by a three-step purification procedure, including reversed-phase HPLC and further ion-exchange chromatography.

Figure 18:
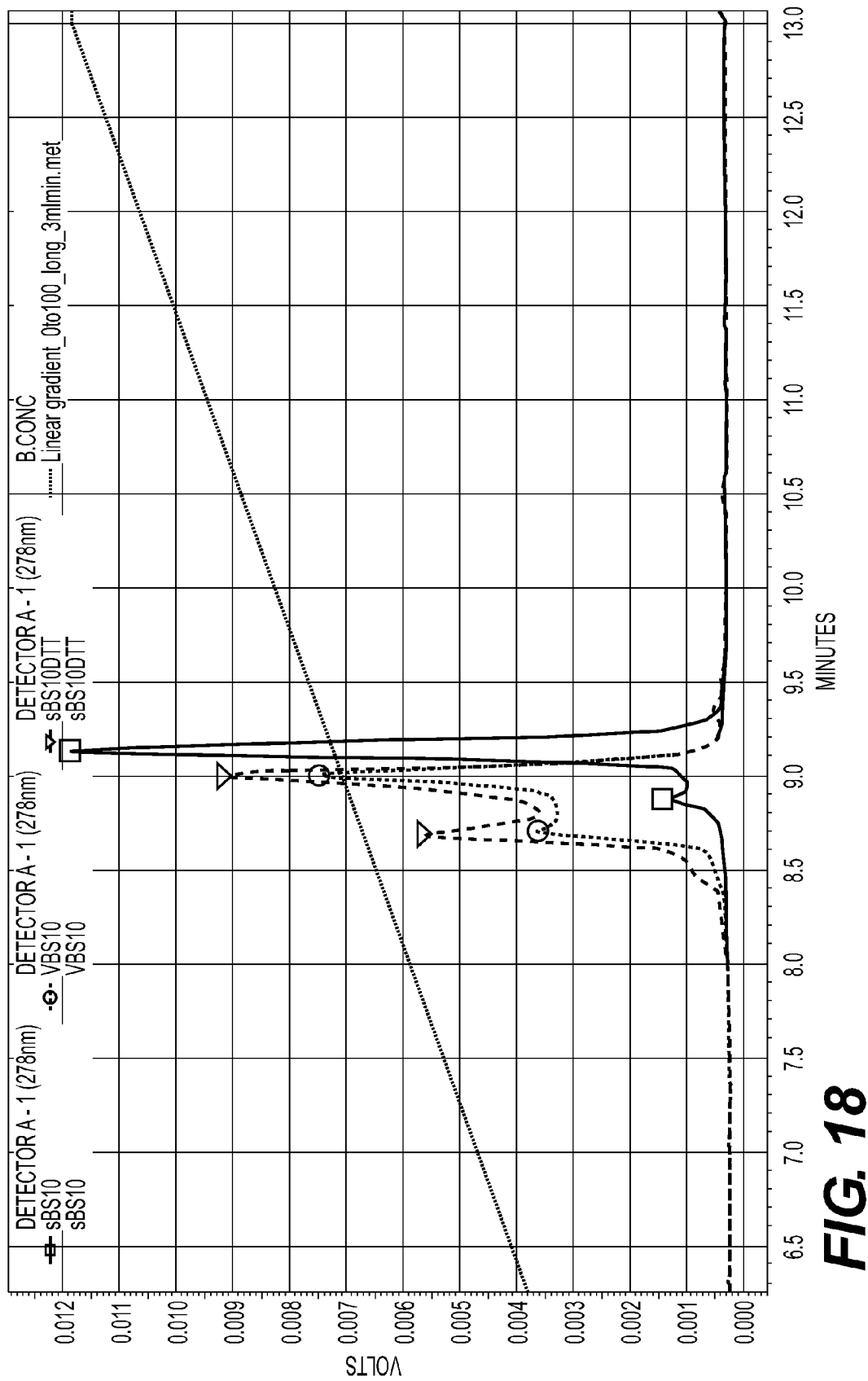
FIG. 18 is a representation of analytical reversed-phase HPLC chromatograms of native peptide F (triangle), reduced synthetic peptide F with 20 mM DTT for 1 hr. (square) and folded synthetic peptide F (circle).
Figure 19:
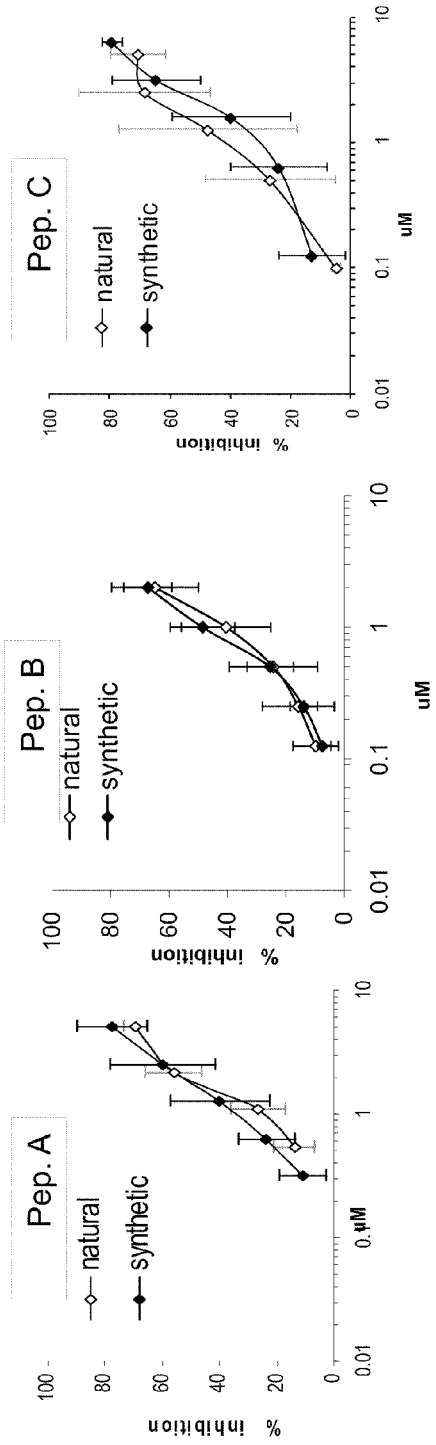
FIGS. 19A-F are representations of a comparison of native and synthetic peptides blocking activities represented as % inhibition of $rNa_V1.3$ channels current versus peptide concentration (dose response) for peptides A-F.

The reversed-phase HPLC purification was carried out using Jupiter C-18 column by liner gradient of 40 min of (29-38%) using 60% aqueous $CH_3CN$ containing 0.1% trifluoroacetic acid (TFA) as eluent. The peak fractions were pooled and lyophilized. Excess contamination was removed by ion-exchange chromatography using Luna SCX column by 25 min liner gradient of (50-70%) 700 mM potassium chloride in potassium phosphate buffer (pH=2.5) containing 25% $CH_3CN$. The peak fractions were once again loaded on a Jupiter C-18 column for desalting using a 20 min liner gradient of 30-50% of 60% $CH_3CN$. The peak fractions were lyophilized and characterized by M.S, analytic HPLC and bioassay analysis (see FIG. 18).

Example 3

Isolated Pure Peptides In Vitro Biological Activity

Blocking activity was tested towards the TTX sensitive $Na_V1.3$ and the TTX resistant $Na_V1.8$ channels. Each of these was stably expressed in a mammalian cell line and channel currents were elicited by suitable voltage stimulation. Activity of the toxin was examined by measuring these currents before, during (often in increasing doses) and after bath perfusion of the toxin. The fraction of inhibited current at each toxin dose was measured in at least three separated cells and the mean±SD is plotted.

Peptide A inhibited both $Na_V1.3$ and $Na_V1.8$ channels with apparent $IC_{50}$ of 1.75 and 2.5 μM, respectively.

Peptide B inhibited $Na_V1.3$ channels with apparent $IC_{50}$ of 230 nM.

Peptide C inhibited $Na_V1.3$ channels with apparent $IC_{50}$ of 1.2 μM.

Peptide D inhibited $Na_V1.3$ channels with apparent $IC_{50}$ of 160 nM.

Peptide E inhibited $Na_V1.3$ channels with apparent $IC_{50}$ of 310 nM.

Peptide F inhibited both $Na_V1.3$ and $Na_V1.8$ channels with apparent $IC_{50}$ of 130 and 170 nM, respectively.

Peripheral pain stimuli are sensed by dorsal root ganglion (DRG) neurons which transmit it in the form of action potentials (which is generated by opening of $Na_V$ channels, in DRG neurons membrane) to the spinal cord. In peripheral neuropathy the pain signal is generated by intrinsic action potentials firing of damaged DRG neurons, probably due to a different repertoire of $Na_V$ channels expressed on their membrane. It is assumed that blocking $Na_V$ channels on DRG neurons will inhibit action potential genesis and the transmission of the pain signal. Therefore, we recorded action potentials in rat DRG neurons and examined whether the toxin inhibits it, as a one step further target confirmation. Peptides A (5 μM), B (0.7 μM), C (5 μM), D (0.75 μM), E (0.83 μM) and F (1 μM) inhibited DRG action potentials at a dose higher than the $IC_{50}$ seen for $Na_V1.3$ channels (FIGS. 7-12). The effects of the peptides were compared to the effect of 600 nM TTX, in all cell examined (see FIGS. 7-12, panels F, G).

Two additional in vitro systems were used to examine specificity of the toxin activity as well as a measure for in vitro safety tests.

The first being measurement of $K^+$ currents in cells heterologously expressing the cardiac human $K_V11.1$ (hERG) channel. Three doses of each peptide being the $IC_{50}$ measured for $Na_V1.3$, three and ten times this $IC_{50}$, were used. Peptides A, C, E and F had no effect even in the highest dose examined. Both peptides B and D had an effect of 25% inhibition and only at the highest dose examined.

The second system was spontaneous action potential firing in mouse embryonic stem (ES) cells derived cardiomyocytes. There action potentials are generated spontaneously by the ensemble activity of many ion channels. The effect of the toxin in such a system indicates both its specificity (as the cardiac action potential generation is dependent on the cardiac $Na_V1.5$ channel isoform) as well as its putative in vivo safety at least in regard to cardiac side effects. As a positive control, TTX was perfused at low (300-600 nM) and high (3 µM) concentration, in all the cells examined. Generally, only the higher dose inhibited action potential generation in these cells (see for example FIGS. 9H and 11H). Peptides A (3.8 µM), B (9 µM), C (5 µM), D (0.75 µM), E (0.83 µM) and F (1 µM) had no (or very minor of about 20% inhibition, for peptides B and F) effect on the frequency or the amplitude of action potentials in these cells (FIGS. 7-12, panels H, I).

For each peptide the results of all tests are summarized in Table 3 and in FIGS. 7-12.

Figure 1B:
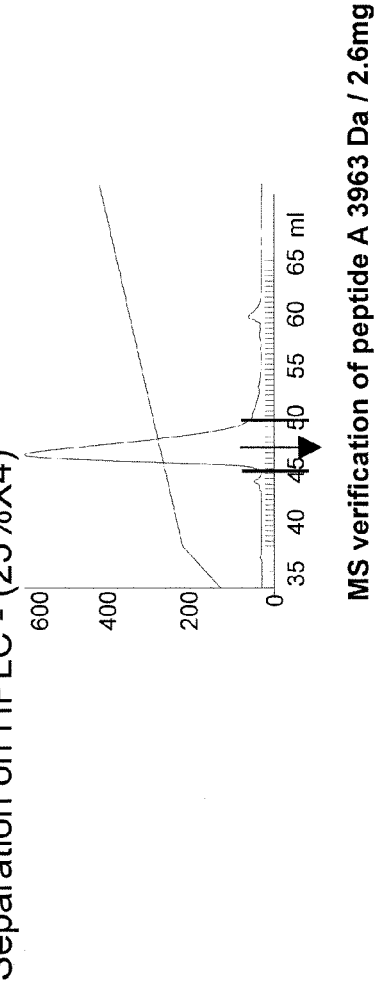
FIG. 1B is an additional graphical representation of a chromatographic purification of peptide A from *Pterinochilus* spp. *Usambara* venom (Psp).

As shown in FIGS. 1A and 1B, peptide A can be obtained by a chromatographic purification from *Pterinochilus* spp. *Usambara* venom (Psp).

Shown in FIGS. 2A, 2B and 2C, peptide B can be obtained by a chromatographic purification from Psp venom.

As shown in FIGS. 3A, 3B and 3C, peptide C can be obtained by a chromatographic purification from *Haplopelma lividum* venom (Hv).

Shown in FIGS. 4A, 4B and 4C, peptide D can be obtained by a chromatographic purification from Hv.

As shown in FIGS. 5A, 5B, 5C and 5D, peptide E can be obtained by a chromatographic purification E from Red Morph *Grammostola* (RMG) venom.

Shown in FIGS. 6A, 6B and 6C, peptide F can be obtained by a chromatographic purification from RMG venom.

FIGS. 7A-I show the In vitro activity of peptide A.

FIG. 7A shows an example of superimposed traces of $rNa_V1.3$ channels response to voltage ramp stimulation (see methods), before and during bath perfusion of 2 µM pure peptide A. As shown in each of FIGS. 7A-7D, the control concentration is represented by the black line and is measured before bath perfusion. In contrast, the grey line represents the voltage measured during bath perfusion.

FIG. 7B shows an example of superimposed traces of $hNa_V1.3$ channels (expressed in *Xenopus* oocytes) response to voltage ramp stimulation (see methods), before and during bath perfusion of 3.4 µM pure peptide A.

FIG. 7C shows an example of superimposed traces of $rNa_V1.8$ channels response to voltage ramp stimulation (see methods), before and during bath perfusion of 2 µM pure peptide A.

FIG. 7D shows an example of superimposed traces of $hK_V11.1$ (hERG) channels response to voltage steps stimulation (see methods), before and during bath perfusion of 5.25 µM pure peptide A. FIG. 7D also shows the response to bath perfusion of an established hERG blocker (200 nM BeKM-1). The response is represented by the thin black line.

FIG. 7E shows dose response curve, summarizing at least 3 experiments for each channel (symbols in inset). Apparent $IC_{50}$s are given in Table 3.

FIG. 7F shows an example of superimposed traces of voltage responses to current stimulation in acutely dissociated rat DRG neurons. Traces are under control conditions, during bath perfusion of 600 nM TTX and during bath perfusion of 5 µM peptide A. As shown in FIG. 7F, the thicker black line represents response under control conditions, the thin black line represents response during bath perfusion of 600 nM TTX and the grey line represents response during bath perfusion of 5 µM peptide A.

FIG. 7G shows a bar chart summarizing several experiments as in the conditions described in FIG. 7F.

FIG. 7H shows an example of a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration.

FIG. 7I shows a bar chart summarizing several experiments in which the effect of 3.75 µM peptide A and 3 µM TTX affected AP frequency.

FIGS. 8A-I show the In vitro activity of peptide B.

Figure 8B:
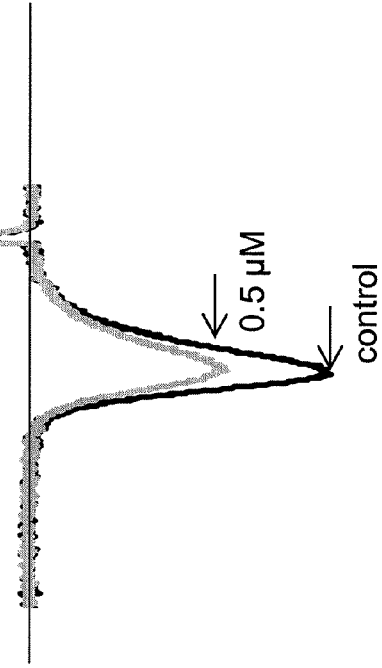
FIG. 8B is a representation of $hNa_V1.3$ channels response to voltage ramp stimulation, before and during bath perfusion of 0.5 µM pure peptide B.
Figure 8C:
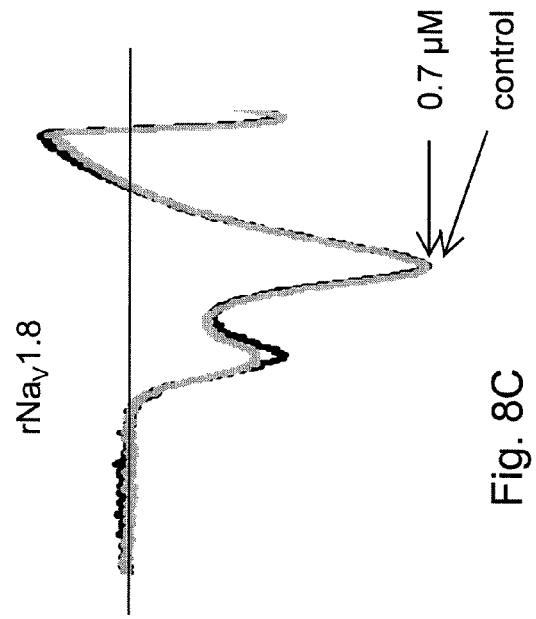
FIG. 8C is a representation of $rNa_V1.8$ channels response to voltage ramp stimulation, before and during bath perfusion of 0.7 µM pure peptide B.
Figure 8A:
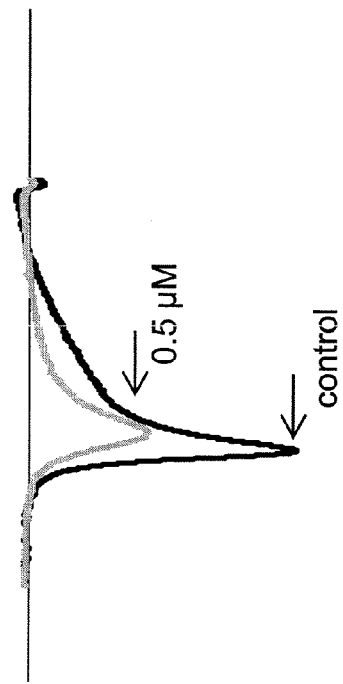
FIG. 8A is a representation of $rNa_V1.3$ channels response to voltage ramp stimulation, before and during bath perfusion of 0.5 µM pure peptide B.

FIG. 8A shows an example of superimposed traces of $rNa_V1.3$ channels response to voltage ramp stimulation (see methods), before and during bath perfusion of 0.5 µM pure peptide B. As shown in each of FIGS. 8A-8D, the control concentration is represented by the black line and is measured before bath perfusion. In contrast, the grey line represents the voltage measured during bath perfusion.

FIG. 8B shows an example of superimposed traces of $hNa_V1.3$ channels (expressed in *Xenopus* oocytes) response to voltage ramp stimulation (see methods), before and during bath perfusion of 0.5 µM pure peptide B.

FIG. 8C shows an example superimposed traces of $rNa_V1.8$ channels response to voltage ramp stimulation (see methods), before and during bath perfusion of 0.7 µM pure peptide B.

Figure 8E:
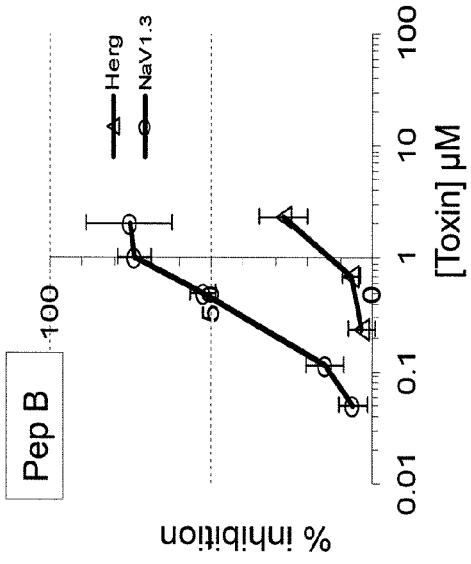
FIG. 8E is a representation of a dose response curve, summarizing at least 3 experiments for each channel represented in FIGS. 8A-8D.
Figure 8D:
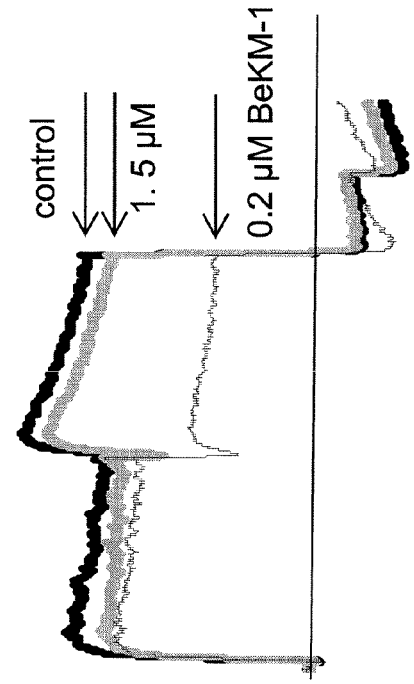
FIG. 8D is a representation of $hK_V11.1$ (hERG) channels response to voltage steps stimulation, before and during bath perfusion of 1.5 µM pure peptide B, and during bath perfusion of an established hERG blocker.

FIG. 8D shows an example superimposed traces of $hK_V11.1$ (hERG) channels response to voltage steps stimulation (see methods), before and during bath perfusion of 1.5 µM pure peptide B. FIG. 8D also shows the response during bath perfusion of an established hERG blocker (200 nM BeKM-1), as represented by the thin black line.

FIG. 8E shows a dose response curve, summarizing at least 3 experiments for each channel (symbols in inset). Apparent $IC_{50}$s are given in Table 3.

Figure 8F:
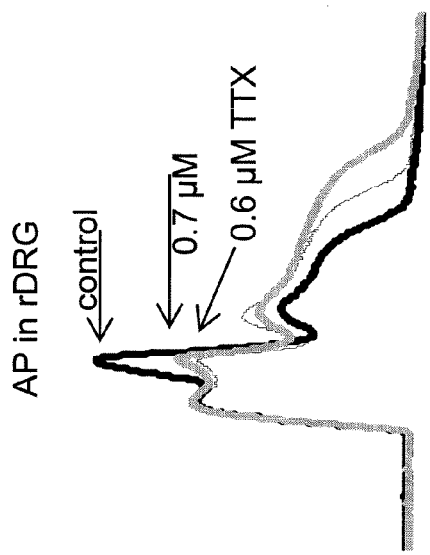
FIG. 8F is a representation of voltage responses to current stimulation in acutely dissociated rat DRG neurons.

FIG. 8F shows an example of superimposed traces of voltage responses to current stimulation in acutely dissociated rat DRG neurons. Traces are under control conditions, during bath perfusion of 600 nM TTX and during bath perfusion of 0.7 µM peptide B. As shown in FIG. 8F, the thicker black line represents response under control conditions, the thin black line represents response during bath perfusion of 600 nM TTX and the grey line represents response during bath perfusion of 0.7 µM peptide B.

FIG. 8G shows a bar chart summarizing several experiments as in the conditions described in FIG. 8F.

FIG. 8H shows a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration.

FIG. 8I shows a bar chart summarizing several experiments in which the effect of 9 µM peptide B and 3 µM TTX affected AP frequency.

FIG. 9A-I shows the In vitro activity of peptide C.

Figure 9B:
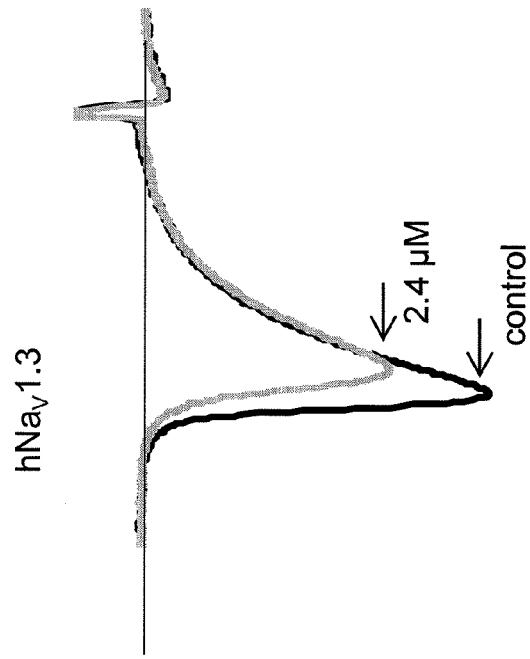
FIG. 9B is a representation of $hNa_V1.3$ channels response to voltage ramp stimulation, before and during bath perfusion of 2.4 µM (Hv3920) pure peptide C.
Figure 9A:
FIG. 9A is a representation of $rNa_V1.3$ channels response to voltage ramp stimulation, before and during bath perfusion of 1.25 µM (Hv3920) pure peptide C.

FIG. 9A shows an example of superimposed traces of $rNa_V1.3$ channels response to voltage ramp stimulation (see methods), before and during bath perfusion of 1.25 µM pure peptide C. As shown in each of FIGS. 9A-9D, the control concentration of is represented by the black line and is measured before bath perfusion. In contrast, the grey line represents the voltage measured during bath perfusion.

FIG. 9B shows an example of superimposed traces of hNa$_V$1.3 channels (expressed in *Xenopus* oocytes) response to voltage ramp stimulation (see methods), before and during bath perfusion of 2.4 µM pure peptide C.

Figure 9C:
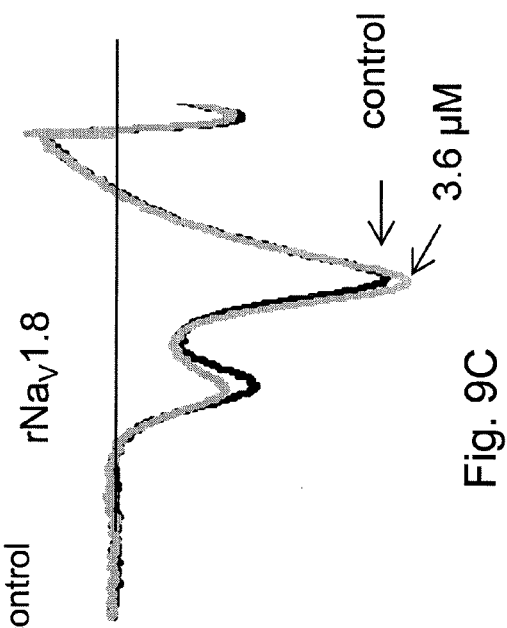
FIG. 9C is a representation of $rNa_V1.8$ channels response to voltage ramp stimulation, before and during bath perfusion of 3.6 µM (Hv3920) pure peptide C.

FIG. 9C shows an example of superimposed traces of rNa$_V$1.8 channels response to voltage ramp stimulation (see methods), before and during bath perfusion of 3.6 µM pure peptide C.

FIG. 9D shows an example of superimposed traces of hK$_V$11.1 (hERG) channels response to voltage steps stimulation (see methods), before and during bath perfusion of 4 µM pure peptide C. FIG. 9D also shows response during bath perfusion of an established hERG blocker (200 nM BeKM-1), as represented by the thin black line.

FIG. 9E is a representation of a dose response curve, summarizing at least 3 experiments for each channel (symbols in inset). Apparent IC$_{50}$s are given in Table 3.

FIG. 9F shows an example superimposed traces of voltage responses to current stimulation in acutely dissociated rat DRG neurons. Traces are under control conditions, during bath perfusion of 300 nM TTX and during bath perfusion of 5 µM peptide C. As shown in FIG. 9F, the thicker black line represents response under control conditions, the thin black line represents response during bath perfusion of 300 nM TTX and the grey line represents response during bath perfusion of 5 µM peptide C.

FIG. 9G shows a bar chart summarizing several experiments as in the conditions described in FIG. 9F.

FIG. 9H shows a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration. As shown, the effects of both low, i.e., 300 nM and high, i.e., 3 µM, concentrations of TTX in this preparation are quite evident.

FIG. 9I shows a bar chart summarizing several experiments in which the effect of 5 µM peptide C and 3 µM TTX affected AP frequency.

FIGS. 10A-I show the In vitro activity of peptide D.

FIG. 10A shows an example of superimposed traces of rNa$_V$1.3 channels response to voltage ramp stimulation (see methods), before and during bath perfusion of 0.15 µM pure peptide D. As shown in each of FIGS. 10A-10D, the control concentration is represented by the black line and is measured before bath perfusion. In contrast, the grey line represents the voltage measured during bath perfusion.

FIG. 10B shows an example of superimposed traces of hNa$_V$1.3 channels (expressed in *Xenopus* oocytes) response to voltage ramp stimulation (see methods), before (black, control) and during bath perfusion of 0.5 µM pure peptide D.

FIG. 10C shows an example of superimposed traces of rNa$_V$1.8 channels response to voltage ramp stimulation (see methods), before and during bath perfusion of 0.48 µM pure peptide D.

FIG. 10D shows an example of superimposed traces of hK$_V$11.1 (hERG) channels response to voltage steps stimulation (see methods), before and during bath perfusion of 1 µM pure peptide D. FIG. 10D also shows response during bath perfusion of an established hERG blocker (200 nM BeKM-1), which is represented by the thin black line.

FIG. 10E shows a dose response curve, summarizing at least 3 experiments for each channel (symbols in inset). Apparent IC$_{50}$s are given in Table 3.

FIG. 10F shows an example of superimposed traces of voltage responses to current stimulation in acutely dissociated rat DRG neurons. Traces are under control conditions, during bath perfusion of 600 nM TTX and during bath perfusion of 0.75 µM peptide D. As shown in FIG. 10F, the thicker black line represents response under control conditions, the thin black line represents response during bath perfusion of 600 nM TTX and the grey line represents response during bath perfusion of 0.75 µM peptide D.

FIG. 10G shows a bar chart summarizing several experiments as in the conditions described in FIG. 10F.

FIG. 10H shows a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration.

FIG. 10I shows a bar chart summarizing several experiments in which the effect of 0.75 µM peptide D and 3 µM TTX affected AP frequency.

FIGS. 11A-I show the In vitro activity of peptide E.

FIG. 11A shows an example of superimposed traces of rNa$_V$1.3 channels response to voltage ramp stimulation (see methods), before and during bath perfusion of 0.3 µM pure peptide E. As shown in each of FIGS. 11A-11D, the control concentration of is represented by the black line and is measured before bath perfusion. In contrast, the grey line represents the voltage measured during bath perfusion.

FIG. 11B shows an example of superimposed traces of hNa$_V$1.3 channels (expressed in *Xenopus* oocytes) response to voltage ramp stimulation (see methods), before and during bath perfusion of 0.93 µM pure peptide E.

FIG. 11C shows an example of superimposed traces of rNa$_V$1.8 channels response to voltage ramp stimulation (see methods), before and during bath perfusion of 0.93 µM pure peptide E.

FIG. 11D shows an example of superimposed traces of hK$_V$11.1 (hERG) channels response to voltage steps stimulation (see methods), before and during bath perfusion of 0.93 µM pure peptide E. FIG. 11D also shows the response during bath perfusion of an established hERG blocker (200 nM BeKM-1), which is represented by a thin black line.

FIG. 11E shows a dose response curve, summarizing at least 3 experiments for each channel (symbols in inset). Apparent IC$_{50}$s are given in Table 3.

FIG. 11F shows an example of superimposed traces of voltage responses to current stimulation in acutely dissociated rat DRG neurons. Traces are under control conditions, during bath perfusion of 600 nM TTX and during bath perfusion of 0.83 µM peptide E (grey, concentration indicated). As shown in FIG. 11F, the thicker black line represents response under control conditions, the thin black line represents response during bath perfusion of 600 nM TTX and the grey line represents response during bath perfusion of 0.83 µM peptide E.

FIG. 11G shows a bar chart summarizing several experiments as in the conditions described in FIG. 11F.

FIG. 11H shows an example of a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration.

FIG. 11I shows a bar chart summarizing several experiments in which the effect of 0.83 µM peptide E and 3 µM TTX affected AP frequency.

FIGS. 12A-I show the In vitro activity of peptide F.

Figure 12A:
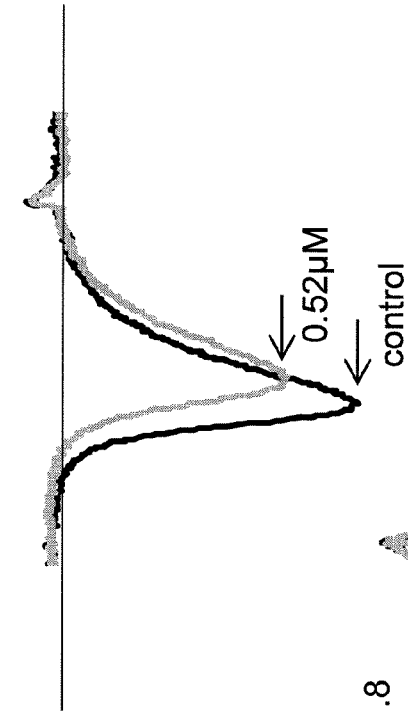
FIG. 12A is a representation of $rNa_V1.3$ channels response to voltage ramp stimulation, before and during bath perfusion of 0.1 µM pure peptide F.

FIG. 12A shows an example of superimposed traces of rNa$_v$1.3 channels response to voltage ramp stimulation (see methods), before and during bath perfusion of 0.1 µM pure peptide F. As shown in each of FIGS. 12A-12D, the control concentration is represented by the black line and is measured before bath perfusion. In contrast, the grey line represents the voltage measured during bath perfusion.

Figure 12B:
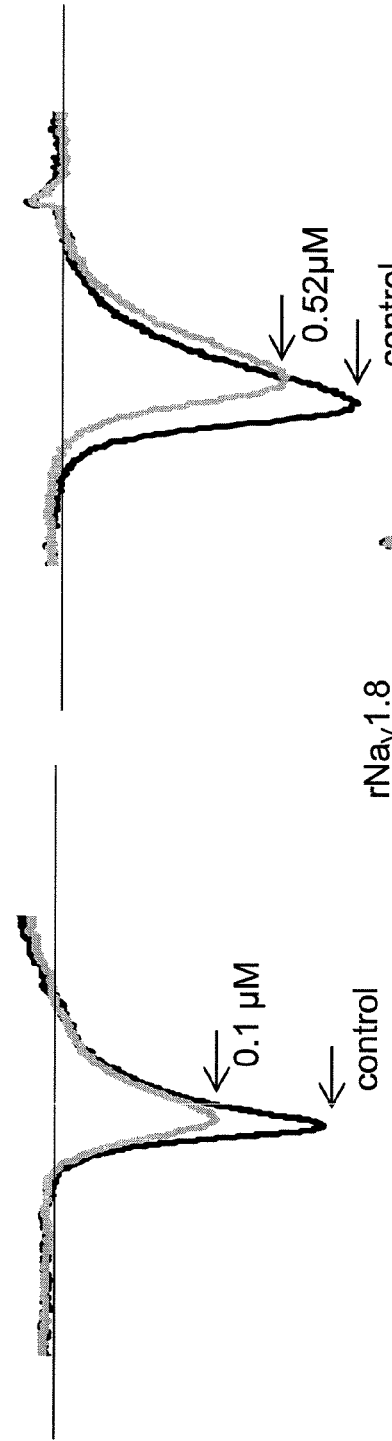
FIG. 12B is a representation of $hNa_V1.3$ channels response to voltage ramp stimulation, before and during bath perfusion of 0.52 µM pure peptide F.

FIG. 12B shows an example superimposed traces of hNa$_v$1.3 channels (expressed in *Xenopus* oocytes) response to voltage ramp stimulation (see methods), before and during bath perfusion of 0.52 µM pure peptide F.

Figure 12C:
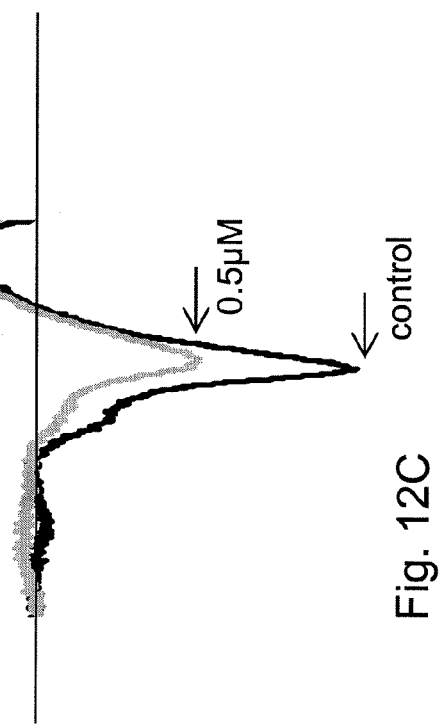
FIG. 12C is a representation of $rNa_V1.8$ channels response to voltage ramp stimulation, before and during bath perfusion of 0.5 µM pure peptide F.

FIG. 12C shows an example superimposed traces of rNa$_v$1.8 channels response to voltage ramp stimulation (see methods), before and during bath perfusion of 0.5 µM pure peptide F.

FIG. 12D shows an example of superimposed traces of hK$_v$11.1 (hERG) channels response to voltage steps stimulation (see methods), before and during bath perfusion of 0.92 µM pure peptide F. FIG. 12D also shows the response during bath perfusion of an established hERG blocker (200 nM BeKM-1), which is shown by a thin black line.

FIG. 12E shows a dose response curve, summarizing at least 3 experiments for each channel (symbols in inset). Apparent IC$_{50}$s are given in Table 3.

FIG. 12F shows an example of superimposed traces of voltage responses to current stimulation in acutely dissociated rat DRG neurons. Traces are under control conditions (black), during bath perfusion of 600 nM TTX and during bath perfusion of 1 µM peptide F. As shown in FIG. 12F, the thicker black line represents response under control conditions, the thin black line represents response during bath perfusion of 600 nM TTX and the grey line represents response during bath perfusion of 1 µM peptide F.

FIG. 12G shows a bar chart summarizing several experiments as in the conditions described in FIG. 12F.

FIG. 12H shows a continuous trace of membrane voltage recorded in a mouse embryonic stem cells derived cardiomyocytes (mES-CM). Action potentials are spontaneously and regularly fired and their frequency and amplitude are plotted in the following charts. The bar represents the period of bath perfusion of compounds at the indicated concentration.

FIG. 12I shows a bar chart summarizing several experiments in which the effect of 1 µM peptide F and 3 µM TTX affected AP frequency.

The in vitro biological activity of six tarantula venom peptides as presented above indicates both the peptide's efficacy for neuropathic pain treatment and their putative cardiac safety.

The target in this indication is inhibition of electrical activity transmission within DRG sensory neurons (in the form of action potentials). Action potential genesis and propagation within DRG neurons depends both on activation of TTX-sensitive (Na$_v$1.3 among others) and TTX-resistance (mainly Na$_v$1.8) channels (Devor, 2006; Cummins et al. 2007). Therefore, efficacy stems from inhibitory actions towards one or two of the target channels Na$_v$1.3 (FIGS. 7A, B, E-12A, B, E) and Na$_v$1.8 (see FIGS. 7C-12C) currents, and towards evoked action potentials in DRG neurons (see FIGS. 7F-12F).

Peptides A and F are inhibitors of both Na$_v$1.3 and Na$_v$1.8 channels (FIGS. 7E and 12E). This may be an advantage in vivo as the exact identity of the best Na$_v$1 channel to target, for neuropathic pain treatment is not fully resolved (Devor, 2006; Cummins et al. 2007). In addition, the most potent peptide in inhibiting the target channels is F followed by D, B and E in the sub-nanomolar range and then by C and A in the micromolar range (see Table 3). All six peptides inhibited action potential generation in DRG neurons. This was measured for each toxin in a concentration about tree times higher than its apparent IC$_{50}$ for the target channel and against the action of TTX in each cell. However, the inhibitory action of peptide A was significantly lower than the effect of 600 nM TTX (see FIGS. 7F, G-12F, G).

The approach was targeting Na$_v$1 channels in the periphery, by peptides that probably do not cross the blood brain barrier (BBB) into the CNS. Therefore, the major concern regarding putative safety is avoidance of modulatory effects on the function of the heart. In line with this notion, indications regarding these peptides putative safety are given by their modulatory action towards the human cardiac potassium hERG (K$_v$11.1) channels currents (Redfern et al. 2003) (FIGS. 7D, E-1D, E) and towards the spontaneous action potential pattern in a model of cardiomyocytes (see FIGS. 7H, I-12H, I).

In the hERG assay, each toxin was measured in a concentration about ten times it's IC$_{50}$ for the target channel and against the action of BeKM-1 (see FIGS. 7D, E-12D, E). Only peptide B and D, exhibited a minor inhibitory action towards this channel at these high concentrations (see FIGS. 8E and 10E). In an integrated model of cardiac activity (Mouse ES-CM), although peptides B and F affected action potential frequency, none of the peptides exhibited significant inhibitory action towards the action potential amplitude and frequency, especially compared to the significant action of 3 µM

TABLE 3

| venom | name | M.W. | IC$_{50}$ Na$_v$1.3 (µM) | IC$_{50}$ Na$_v$1.8 (µM) | % inhibition (mean ± S.D) of hERG at concentration × 10 IC$_{50}$ for Na$_v$1.3 | % inhibition (mean ± S.D) of AP in rDRG & [concentration (µM)] | % inhibition (mean ± S.D) of AP frequency in mES-CM & [concentration (µM)] |
|---|---|---|---|---|---|---|---|
| Psp | A | 3966.7 | 1.75 | 2.50 | 2 ± 2 | 17 ± 10 [5.00] | 1 ± 11 [3.75] |
| Psp | B | 3636.6 | 0.23 | — | 25 ± 7.5 | 28 ± 25 [0.70] | 35 ± 36 [9.00] |
| Hv | C | 3917.8 | 1.20 | — | 2 ± 14 | 38 ± 14 [5.00] | 16 ± 8 [5.00] |
| Hv | D | 3705.6 | 0.16 | — | 25 ± 25 | 48 ± 37 [0.75] | 11 ± 7 [0.75] |
| RMG | E | 4070.8 | 0.31 | — | 2 ± 2 | 44 ± 16 [0.83] | −4 ± 5 [0.83] |
| RMG | F | 4168.8 | 0.13 | 0.17 | 6 ± 7 | 46 ± 24 [1.00] | 25 ± 23 [1.00] |

TTX (see FIGS. 7H, I-12H, I). Therefore, none of the peptides seemed to block assumed normal cardiac activity in a significant manner in their effective concentrations for inhibition of target channels activity.

Example 4

Comparison of Native and Synthetic Peptide Activities

Comparison between the blocking activities of the synthetic and the native peptides was tested according to the procedure in Example 3 and the methods section.

Similar dose response curves were obtained with native and synthetic peptides for inhibiting $rNa_v1.3$ channels expressed in HEK cells, each data point is the average of 3-5 experiments.

The dose response curves of peptide A, B, C, D, E and F overlap completely and therefore the activity is identical for the native and synthetic peptides. The responses of channels to synthetic peptide D and E seem greater than to the native peptide, but this difference is within the range of responses recorded. As the synthetic and native peptides look identical by Mass-spec and HPLC analyses and their activities as $Na_v1.3$ channel blockers are very similar, we conclude that the synthesis procedure was successful in providing peptides identical to those purified from venom.

Example 5

Evaluation of Compound C for Analgesic Indication in Rat Model

This study aimed to evaluate the analgesic indications of compound C using the Chung model of neuropathic pain in rats. This study was performed at PsychoGenics, Inc., headquartered at 765 Old Saw Mill River Road, Tarrytown, N.Y.

Material and Methods

Animals

Male Sprague Dawley rats (100-125 g) from Harlan (Indianapolis, Ind.) were used in the study. Upon receipt, rats were assigned unique identification numbers and were group housed with 3 rats per cage in polycarbonate cages with micro-isolator filter tops. All rats were examined, handled, and weighed prior to initiation of the study to assure adequate health and suitability. During the course of the study, 12/12 light/dark cycles were maintained, with lights on at 7:00 am EST. The room temperature was maintained between 20 and 23° C. with a relative humidity maintained around 50%. Chow and water were provided ad libitum for the duration of the study.

Drugs

All compounds were administered at a dose volume of 5 ml/kg, q.d. for 5 days (Days 17-21 post-surgery). Reference compound: Gabapentin (100 mg/kg; TRC, Lot No. 1-SWM-154-1) was dissolved in 0.5% carboxy-methylcellulose (CMC) in water and administered orally. Test Compound: Compound C (0.25, 0.625, and 1.25 mg/kg; Lot n/a) was dissolved in distilled $H_2O$ to a stock concentration (20×), divided into single-use aliquots, and frozen. On each test day, one aliquot was thawed and diluted 20-fold with PBS (pH 7.2), and used as stock for formulation of test doses. Compound C was administered subcutaneously.

Methods

Chung Model for Neuropathic Pain (Spinal Nerve Ligation)

Under general anesthesia with continuous inhalation of isoflurane, surgery was performed with aseptic procedures in surgery unit. The skin at the area of the lower lumber and sacral level of the rat was shaved and disinfected with betadine and alcohol. Sterile ophthalmic ointment was used to lubricate the eyes. Animals were observed continuously for the level of anesthesia, testing for the animal's reflex response to tail or paw pinch and closely monitoring the animal's breathing. A heating pad was used to maintain body temperature at 37° C. while the animals recovered from anesthesia. A left longitudinal incision at the level next to the vertebral column was made and the left paraspinal muscles were separated. The transverse process of L6 was removed and nearby connective tissue cleaned to expose L5 and L6 spinal nerves. After the nerves were isolated and clearly visualized, 4-0 silk threads were used to ligate the left L5. The muscles were sutured with 4-0 silk threads and the wound closed by staples. All rats received an analgesic (buprenorphine, 0.05 mg/kg, s.c.) immediately before and 6 hours after surgery. Each rat was monitored until awake and moving freely around the recovery chamber. Animals were then single-housed for the duration of the study. Rats were allowed to recover for 2 weeks after surgery prior to testing.

Evaluation of Plantar Hypersensitivity to Tactile Stimuli (Von Frey Test)

Withdrawal from a mechanical stimulus was measured by applying von Frey (VF) filaments of ascending bending force to the plantar surface of the hind paws (ipsilateral and contralateral). A positive response was defined as withdrawal from the von Frey filament. Confirmation of the paw withdrawal threshold (PWT) is tested by assessing the response to the filament above and below the withdrawal response.

Rats were brought to the experimental room and allowed to habituate in the room for one hour prior to testing, and acclimated to the observation chambers for 15 minutes prior to taking PWT measurements.

Pre-operative baseline testing: Prior to surgery, all rats were tested using the VF test. Rats that had an ipsilateral PWT of less than 12 g were excluded from the study (1 rat excluded).

Post-operative baseline testing: On Day 14 following surgery, baseline responses were taken from all surgically-operated rats, and an ipsilateral PWT greater than 4.5 g was used as an exclusion criterion (13 rats excluded). Rats were subsequently balanced and assigned to treatment groups (n=10 per group) based on their post-op PWT values.

Acute and chronic testing: On Day 17 post-surgery, rats were injected with vehicle, gabapentin, or test compound and tested 1 and 3 hours following administration. Test compounds were administered for 5 days, and rats were tested again on day 5 (Day 21 post-op).

Statistical Analysis

Von Frey data were analyzed by repeated measures or one-way analysis of variance (ANOVA) followed by Fisher PLSD post-hoc comparisons. An effect was considered significant if $p<0.05$. Data is presented as the mean±standard error of the mean (S.E.M.).

Results

Baseline von Frey Test (VF)—Pre and Post-Ligation

Figure 20:
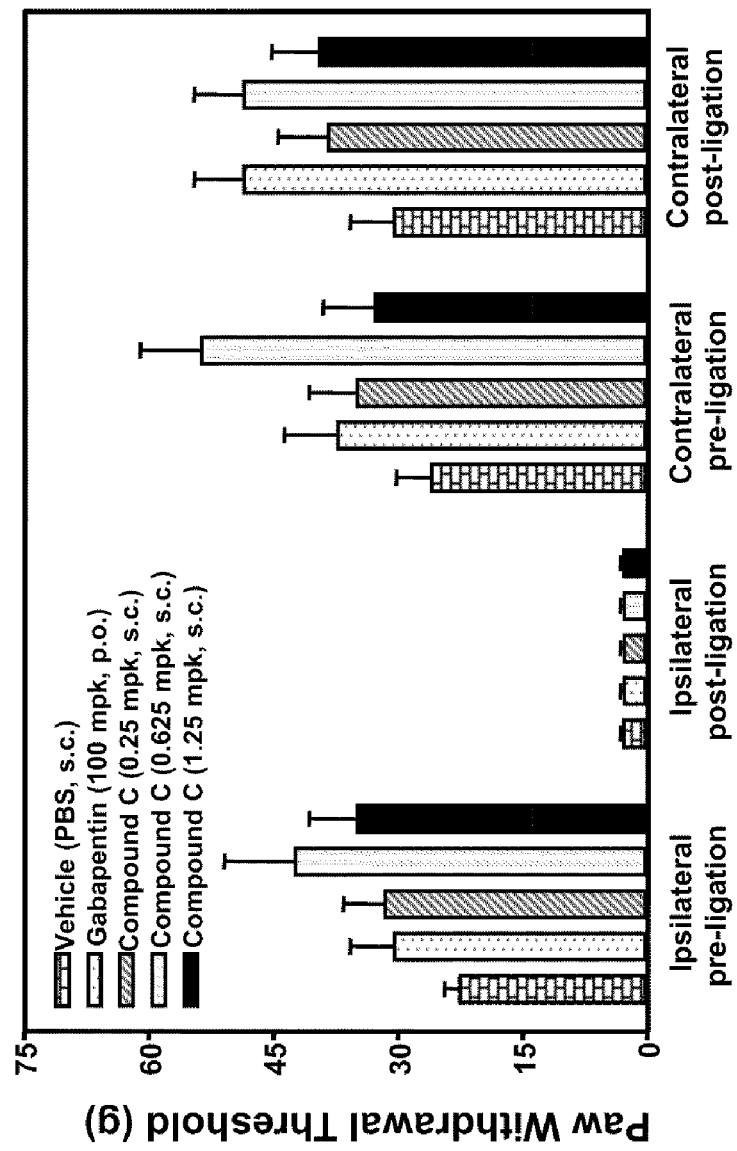
FIG. 20 is a representation of paw withdrawal thresholds pre- and post-ligation for ipsilateral and contralateral hindpaws.

Spinal nerve ligation resulted in a significantly decreased paw withdrawal threshold in the hind paw ipsilateral, but not contralateral, to the lesion, as indicated by a significant Ligation X Paw interaction effect (see FIG. 20).

Acute and Chronic VF Testing

Table 4 shows the ipsilateral and contralateral paw withdrawal threshold values (mean±SEM) prior to drug administration.

TABLE 4

| Treatment | Ipsilateral | Contralateral |
| --- | --- | --- |
| Vehicle | 2.99 ± 0.26 | 30.60 ± 5.10 |
| Gabapentin 100 mg/kg | 2.94 ± 0.29 | 48.70 ± 5.83 |
| Compound C 0.25 mg/kg | 2.94 ± 0.29 | 38.50 ± 5.95 |
| Compound C 0.625 mg/kg | 2.94 ± 0.29 | 48.70 ± 5.83 |
| Compound C 1.25 mg/kg | 2.99 ± 0.26 | 39.60 ± 5.55 |

Figure 21:
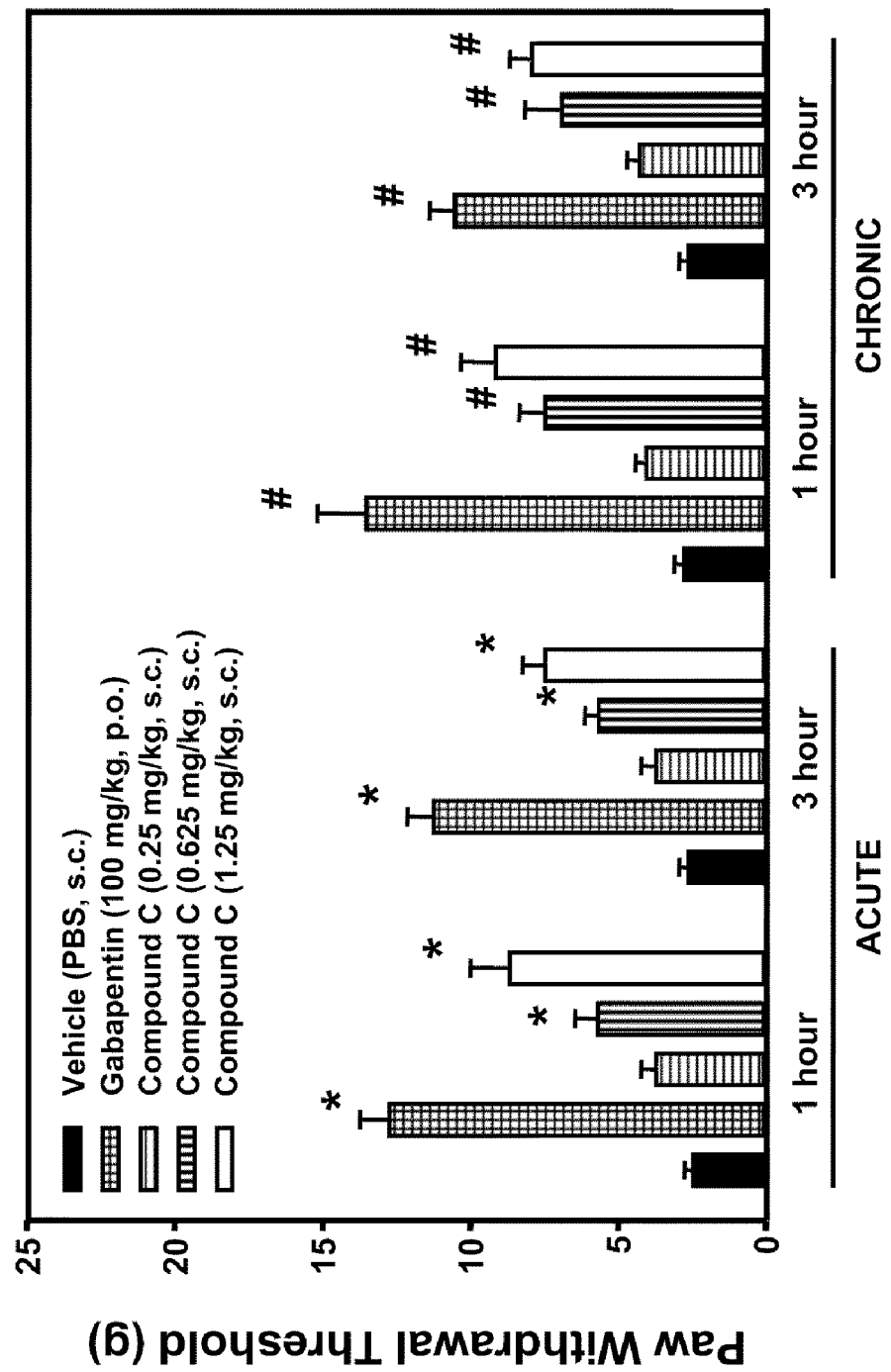
FIG. 21 is a representation of ipsilateral paw withdrawal thresholds for 1 and 3 hour time points following acute and chronic administration of test compound.

The effects of acute and chronic administration of gabapentin and compound C on tactile stimulus response in spinal-ligated rats are shown in FIG. 21. Signs of sedation or toxicity were not observed during pretreatment or testing.

Acute—Ipsilateral

A two-way repeated measures ANOVA yielded a significant main effect of treatment, and a non-significant trend towards a main effect of time (p=0.09) on Day 17. Post hoc tests indicated that acute administration of gabapentin and compound C (0.625 and 1.25 mg/kg) significantly increased ipsilateral paw withdrawal threshold compared to vehicle for data collapsed across both time points.

Chronic—Ipsilateral

On Day 21, two-way repeated measures ANOVA yielded a significant treatment X time interaction effect, and significant main effects of treatment and time. Post hoc tests indicated that gabapentin and compound C (0.625 and 1.25 mg/kg) significantly increased ipsilateral paw withdrawal threshold compared to vehicle at all time points following chronic treatment regimen. The effects of gabapentin were significantly greater at 1 hr. compared to 3 hr. post-administration.

Contralateral

Figure 22:
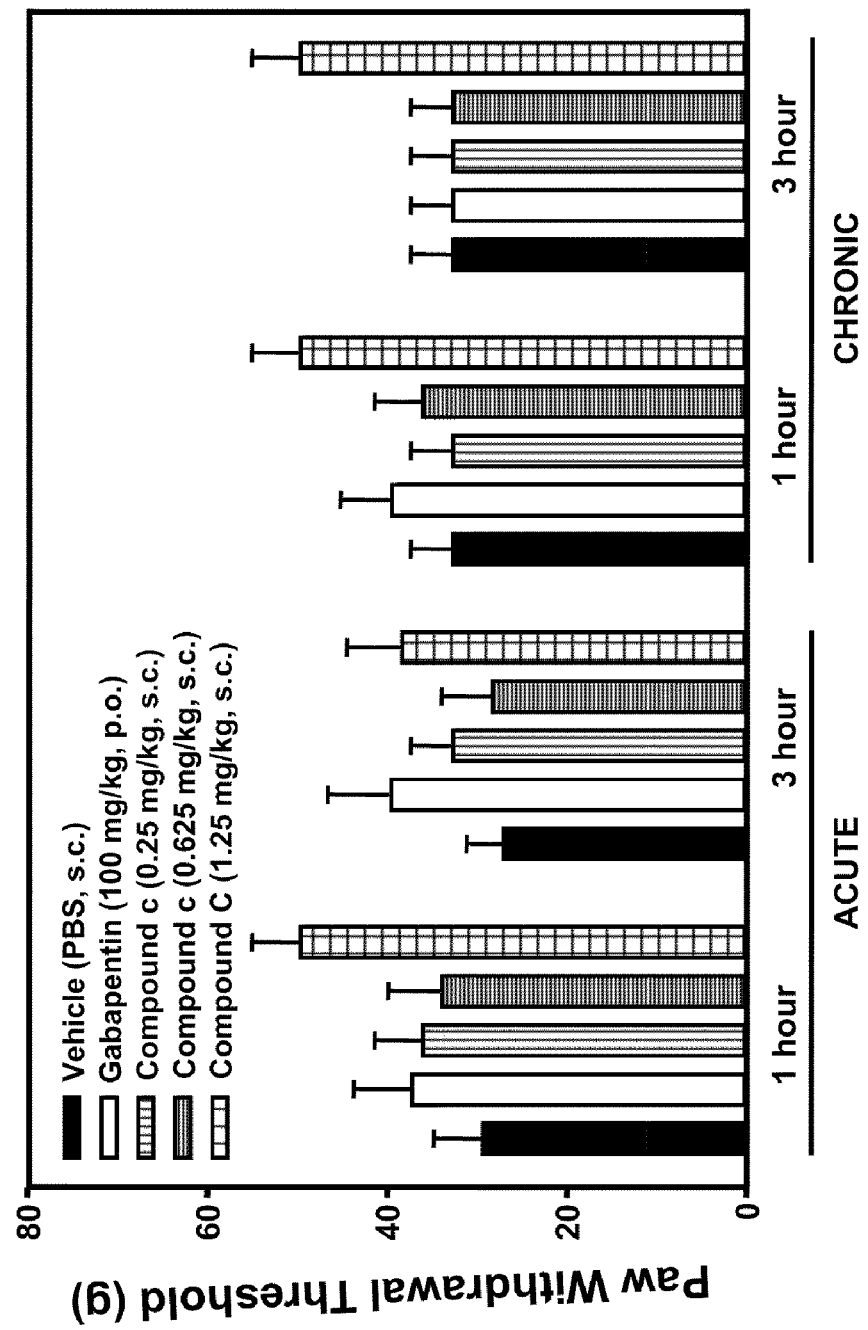
FIG. 22 is a representation of contralateral paw withdrawal thresholds for 1 and 3 hour time points following acute and chronic administration of test compounds.

The effects of all treatments on contralateral paw withdrawal threshold are shown in FIG. 22. Two way repeated measures ANOVA found no significant treatment X time interaction effect or a significant main effect of treatment on either day 17 (acute) or on day 21 (chronic).

Summary

Acute or 5-day administration of gabapentin (100 mg/kg) and compound C (0.625 and 1.25 mg/kg) significantly increased ipsilateral paw withdrawal threshold (PWT) at both time points (1 and 3 hours following administration). There were no significant compounds of any test compounds on contralateral paw withdrawal threshold values.

Example 6

A patient is suffering from neuropathic pain. A pharmaceutical composition as described herein is systemically administered to the patient. It would be expected that the patient would improve his/her condition or recover.

Example 7

Prophetic clinical trial evaluating the administration of pharmaceutical compositions comprising any of the peptides as described herein to assess efficacy in neuropathic pain and safety in a double-blind multicenter placebo-controlled trial Study Design A 12-week study using a randomised, double-blind, multicenter, placebo-controlled, parallel-group design to evaluate the efficacy and safety of twice-weekly flexible- (50-200 μg of any of the peptides described herein/week) or fixed-dose (200 μg of any of the peptides described herein/week) in patients with chronic neuropathic pain. The study is conducted in multiple centers in several countries.

The study adheres to the ethical principles originating from the Declaration of Helsinki Subjects Eligible patients are men and non-pregnant, non-lactating women ≧18 years of age with a primary diagnosis of painful diabetic peripheral neuropathy (DPN) (type 1 or 2 diabetes mellitus with glycosylated haemoglobin [HbA1c]% 11% and painful, distal, symmetrical, sensorimotor polyneuropathy for ≧6 months) or postherpetic neuralgia (PHN) (pain present for ≧3 months after healing of the herpes zoster skin rash). Patients are also required to have a score ≧40 mm (0 mm='no pain' and 100 mm='worst possible pain') on the Visual Analogue Scale (VAS) of the Short-Form McGill Pain Questionnaire (SF-MPQ) at baseline and randomisation.

Patients are excluded if they had any clinically significant or unstable medical or psychiatric condition. Patients who had a malignancy within the past 2 years or an anticipated need for surgery during the study are also excluded, as are patients with an abnormal electrocardiogram (ECG), creatinine clearance !60 ml/min, or abnormal haematology. Patients who had abused illicit drugs or alcohol within the last 2 years are excluded. Those who had participated in a previous clinical trial for pregabalin or had taken any investigational drug or agent within 30 days prior to screening are also excluded. Medications prohibited for use during the study, and which are required to be washed out at least 7 days prior to baseline visit, included the following: drugs commonly used to treat neuropathic pain (e.g. benzodiazepines, skeletal muscle relaxants, capsaicin, local anaesthetics, opioids, memantine), antiepileptic drugs (e.g. carbamazepine, clonazepam, phenytoin, valproic acid, lamotrigine, topiramate, gabapentin), non-SSRI antidepressants (e.g. tricyclics, venlafaxine), and potential retinotoxins (e.g. hydroxychloroquine, deferoxamine, thioridazine, vigabatrin).

Patients with DPN are also prohibited from taking NSAIDS (including COX-2 inhibitors) and dextromethorphan without a washout of at least 1 day. Patients who had been exposed previously to gabapentin, regardless of dose and treatment duration, are permitted to enter the study. SSRIs for treatment of depression, aspirin for myocardial infarction and stroke prophylaxis, short-acting benzodiazepines for insomnia, and paracetamol or the like as rescue medication are allowable medications during the study period. Patients are also excluded if they had a history of hepatitis B or C or HIV infection, neurologic disorders, severe pain unrelated to their primary diagnosis of DPN or PHN, or any potentially sensation-altering skin conditions in the affected dermatome or area of neuropathic involvement that could confound their assessment of neuropathic pain. Finally, patients with DPN and a history of pernicious anaemia, untreated hypothyroidism, or amputations other than toes are also excluded, as were patients with PHN who had undergone neurolytic or neurosurgical therapy for their condition.

Treatments

The study has two phases: a 1-week observation phase to establish baseline pain scores and a 12-week double-blind treatment phase in which a blinded adaptation in response to patients' needs was applied in one of the treatment arms. Patients are randomised in 1:2:2 ratio to placebo (n=65), flexible-dose composition (50-200 μg of any of the peptides described herein/week) (n=135), or fixed-dose composition (200 μg of any of the peptides described herein/week) (n=140).

Patients randomised to the composition flexible-dose group receive escalating doses (50, 100, 150 and 200 μg of any of the peptides described herein/week) titrated at weekly intervals based on response and tolerability. A single downward dose titration, after Week 1 or at or after Week 2, 3, or 4, is allowed. If this occurs, the patient will remain on this dosage for the rest of the study. The advantage of this new study design is that it more closely approximates the treatment routine in which doctors tailor the dosage of prescribed drugs based on individual patients' responses. Patients randomised to the composition comprising 200 µg of any of the peptides described herein/week fixed-dose group start with a composition comprising 100 µg of any of the peptides described herein/week for 1 week and then follow with a composition comprising 200 µg of any of the peptides described herein/week for the remaining 11 weeks of double-blind treatment. All patients receive active medication or matching placebo capsules and follow the same twice weekly sub-cutaneous injection schedule (weekly dosages are split into two equivalent doses, administered within 3-4 day intervals). Adherence is assessed by medication inventory control and review of dosing procedure at each study visit. At any time during the double-blind trial, patients are free to discontinue it and enter the open-label extension.

Evaluations and Endpoints

During the baseline phase (no active treatment), patients make daily diary entries of pain and pain-related sleep interference using 11-point numerical (0='no pain' to 10='worst possible pain'; 0='pain does not interfere with sleep' to 10='pain completely interferes with sleep') rating scales (NRS). Patients who continue to meet all inclusion/exclusion criteria at the end of this phase are randomised to double-blind study medication and evaluated at six post-randomisation visits. The primary efficacy parameter is an endpoint mean pain score based on patients' NRS scores as recorded in their daily pain diaries. On awakening each morning, patients record their neuropathic pain intensity during the previous 24 h in their diaries, using the NRS. Secondary efficacy parameters included the Daily Sleep Interference Diary (similar to the pain diary) and the Medical Outcomes Study (MOS)-Sleep Scale (Hays and Stewart, 1992), and the Patient Global Impression of Change (PGIC). The MOSSleep Scale is a validated, 12-item, patient-completed questionnaire used to measure the influence of sleep on health-related quality of life.

Safety

Safety assessments included summary of adverse events (AEs, occurrence, nature, intensity, and relationship to study drug), clinical laboratory test results, and the results of physical and neurologic examinations and 12-lead ECGs.

It would be expected that the patients receiving compositions comprising any of the peptides described herein would have reduced pain, inflammation and other symptoms related to the chronic neuropathic pain.

It will be appreciated by those skilled in the art to which the present subject matter pertains that various modifications can be made without departing from the essential nature thereof. It is intended to encompass all such modification within the scope of the appended claims.

What is claimed:

1. An isolated peptide, comprising: the amino acid sequence as set forth in SEQ ID NO: 3, or a C-terminally amidated form thereof.

2. A pharmaceutical composition, comprising the isolated peptide of claim 1; and a pharmaceutically acceptable carrier or diluent.

3. A method of treating pain, comprising: administering to a subject in need of such treatment an effective analgesic amount of the isolated peptide of claim 1.

4. The method of claim 3, wherein the pain is neurogenic and/or neuropathic pain.

5. The method of claim 3, wherein the pain is cancer pain, post-surgical pain, oral or dental pain, pain from referred trigeminal neuralgia, pain from post-herpetic neuralgia, or pain due to reflex sympathetic dystrophy.

6. The method of claim 3, wherein the pain is associated with an inflammatory condition.

7. The method of claim 3, wherein the pain is associated with one or more conditions selected from the group consisting of acute pain, migraine, headache pain, migraine headache, traumatic nerve injury, nerve compression, nerve entrapment, postherpetic neuralgia, trigeminal neuralgia, diabetic neuropathy, chronic lower back pain, phantom limb pain, chronic pelvic pain, neuroma pain, complex regional pain syndrome, chronic arthritic pain, and pain associated with cancer, chemotherapy, HIV and HIV treatment-induced neuropathy, irritable bowel syndrome and related disorders and Crohns disease.

8. A method of treating pain in a subject, comprising administering to the subject in need thereof, a therapeutically effective amount of the pharmaceutical composition of claim 2.

9. The isolated peptide of claim 1, wherein the peptide is isolated from spider venom.

10. The isolated peptide of claim 1, wherein the peptide is an isolated synthetic peptide.

11. The isolated peptide of claim 9, wherein the spider is a species of tarantula.

12. A method for refolding the peptide of claim 1, comprising: collecting crude peptides of spider venom to produce collected peptides; solubilizing the collected peptides to produce solubilized peptides; reducing the solubilized peptides to produce reduced peptides; folding the reduced peptides in redox mixture comprising reduced and/or oxidized cysteine or glutathione to produce folded peptide; and purifying the folded peptide to produce refolded peptide.

* * * * *